US012758614B2

(12) United States Patent
Turtle et al.

(10) Patent No.: US 12,758,614 B2
(45) Date of Patent: Oct. 13, 2026

(54) AUGMENTING ANTIGEN-NEGATIVE CELL DEATH IN ANTIGEN-TARGETED IMMUNOTHERAPIES

(71) Applicant: Fred Hutchinson Cancer Center, Seattle, WA (US)

(72) Inventors: Cameron J. Turtle, Seattle, WA (US); Salvatore Fiorenza, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 827 days.

(21) Appl. No.: 17/907,657

(22) PCT Filed: Mar. 31, 2021

(86) PCT No.: PCT/US2021/025260

§ 371 (c)(1),
(2) Date: Sep. 28, 2022

(87) PCT Pub. No.: WO2021/202801

PCT Pub. Date: Oct. 7, 2021

(65) Prior Publication Data

US 2023/0218669 A1 Jul. 13, 2023

Related U.S. Application Data

(60) Provisional application No. 63/003,209, filed on Mar. 31, 2020.

(51) Int. Cl.

| | |
|---|---|
| ***A61K 35/17*** | (2025.01) |
| ***A61K 38/19*** | (2006.01) |
| ***A61K 40/10*** | (2025.01) |
| ***A61K 40/31*** | (2025.01) |
| ***A61K 40/42*** | (2025.01) |
| ***C07K 14/525*** | (2006.01) |
| ***C07K 14/705*** | (2006.01) |
| ***C07K 14/725*** | (2006.01) |
| ***C12N 5/0783*** | (2010.01) |
| ***C12N 15/11*** | (2006.01) |

(52) U.S. Cl.

CPC ............ *A61K 38/191* (2013.01); *A61K 40/10* (2025.01); *A61K 40/31* (2025.01); *A61K 40/4232* (2025.01); *C07K 14/525* (2013.01); *C07K 14/7051* (2013.01); *C12N 5/0636* (2013.01); *C12N 15/11* (2013.01); *A61K 2239/46* (2023.05)

(58) Field of Classification Search

CPC .. A61K 38/191; A61K 40/31; A61K 40/4232; A61K 2239/46; A61K 31/343; A61K 31/427; A61K 31/436; A61K 38/177; C07K 14/525; C07K 14/7051; C07K 14/70578; C12N 5/0636; C12N 15/11

See application file for complete search history.

(56) References Cited

U.S. PATENT DOCUMENTS

| | | | |
|---|---|---|---|
| 8,202,902 B2 | 6/2012 | Wang | |
| 8,278,293 B2 | 10/2012 | Wang | |
| 8,283,372 B2 | 10/2012 | Condon | |
| 8,664,212 B2 | 3/2014 | Wang | |
| 8,716,236 B2 | 5/2014 | Cohen | |
| 8,883,771 B2 | 11/2014 | Wang | |
| 8,980,837 B2 | 3/2015 | Cohen | |
| 8,986,993 B2 | 3/2015 | Condon | |
| 9,783,538 B2 | 10/2017 | Chessar | |
| 2005/0163747 A1 | 7/2005 | Hilbert | |
| 2010/0098770 A1 | 4/2010 | Ramalingam | |
| 2010/0317593 A1 | 12/2010 | Aquila | |
| 2012/0238766 A1 | 9/2012 | Porco, Jr. | |
| 2015/0158908 A1 | 6/2015 | Condon | |
| 2016/0184383 A1 | 6/2016 | Lalaou | |
| 2017/0037004 A1 | 2/2017 | Crew | |
| 2017/0319592 A1 | 11/2017 | Cho | |
| 2018/0065959 A1 | 3/2018 | Chessari | |
| 2018/0155322 A1 | 6/2018 | Crew | |
| 2018/0179183 A1 | 6/2018 | Crew | |
| 2018/0186882 A1 | 7/2018 | Freeman | |
| 2018/0193470 A1 | 7/2018 | Crew | |
| 2019/0031766 A1 | 1/2019 | Prinz | |
| 2019/0135794 A1 | 5/2019 | Sun | |
| 2019/0151295 A1 | 5/2019 | Crew | |
| 2019/0185511 A1 | 6/2019 | Kanne | |
| 2019/0328787 A1 * | 10/2019 | Maus | C07K 14/70575 |
| 2020/0054673 A1 | 2/2020 | Ports et al. | |

FOREIGN PATENT DOCUMENTS

| | | |
|---|---|---|
| AU | 2017223233 | 8/2018 |
| CN | 110267973 A | 9/2019 |

(Continued)

OTHER PUBLICATIONS

Wikipedia contributors. “His-tag.” Wikipedia, The Free Encyclopedia. Wikipedia, The Free Encyclopedia, Oct. 16, 2024. Web. Jun. 27, 2025. (Year: 2024).*

Lemke, J.V., von Karstedt, S., Zinngrebe, J. and Walczak, H., 2014. Getting TRAIL back on track for cancer therapy. Cell Death & Differentiation, 21(9), pp. 1350-1364. (Year: 2014).*

Chyuan, I.T., Tsai, H.F., Wu, C.S., Sung, C.C. and Hsu, P.N., 2018. TRAIL-mediated suppression of T cell receptor signaling inhibits T cell activation and inflammation in experimental autoimmune encephalomyelitis. Frontiers in immunology, 9, p. 15. (Year: 2018).*

(Continued)

*Primary Examiner* — Christopher M Babic
*Assistant Examiner* — Masudur Rahman
(74) *Attorney, Agent, or Firm* — Lee & Hayes, P.C.

(57) ABSTRACT

Combination therapies that include (i) an immune cell that expresses a chimeric antigen receptor (CAR) or similar molecule and (ii) a compound that preserves or potentiates the in vivo actions of tumor necrosis factor alpha (TNFα) against cancer cells are described. The combination therapies result in the killing of antigen-negative cells in the vicinity of immunotherapy targeted-antigen-positive cells reducing the survivability of escape variants and providing other benefits.

20 Claims, 22 Drawing Sheets

Specification includes a Sequence Listing.

(56) References Cited

FOREIGN PATENT DOCUMENTS

| | | | |
|---|---|---|---|
| CN | 110381963 | A | 10/2019 |
| EP | 1693059 | A1 | 8/2006 |
| EP | 3105317 | B1 | 9/2018 |
| JP | 2017521499 | A | 8/2017 |
| JP | 2019533676 | A | 11/2019 |
| KR | 20190084053 | A | 7/2019 |
| WO | WO2006116727 | A2 | 11/2006 |
| WO | WO2011084714 | A2 | 7/2011 |
| WO | WO2015109391 | A1 | 7/2015 |
| WO | WO2017117684 | A1 | 7/2017 |
| WO | WO2018017426 | A1 | 1/2018 |
| WO | WO2018132513 | A1 | 7/2018 |
| WO | WO2019060174 | A1 | 3/2019 |
| WO | WO2019122337 | A1 | 6/2019 |
| WO | WO2019122941 | A1 | 6/2019 |
| WO | WO2019152660 | A1 | 8/2019 |
| WO | WO2019165215 | A1 | 8/2019 |
| WO | WO2019234220 | A1 | 12/2019 |
| WO | 2020002579 | A1 | 1/2020 |
| WO | WO2020024932 | A1 | 2/2020 |
| WO | WO2020028572 | A2 | 2/2020 |

OTHER PUBLICATIONS

Brudno, J.N., et al., 2018. T cells genetically modified to express an anti-B-cell maturation antigen chimeric antigen receptor cause remissions of poor-prognosis relapsed multiple myeloma. Journal of Clinical Oncology, 36(22), pp. 2267-2280. (Year: 2018).*

Search Report for European Patent Application No. 21780314.7, Dated Jun. 5, 2024, 20 pages.

Search Report and Written Opinion Dated Aug. 5, 2021 in International Application No. PCT/US2021/025260, 13 pages.

Webber, et al., "Highly efficient multiplex human T cell engineering without double-strand breaks using Cas9 base editors," Nature Communications, vol. 10, No. 5222, 2019, 10 pages.

Zhang, et al., "Sequential allogeneic and autologous CAR-T-cell therapy to treat an immune-compromised leukemic patient," Blood Advances, vol. 2, No. 14, 2018, pp. 1691-1695.

Ding, et al., "WX20120108, a novel IAP antagonist, induces tumor cell autophagy via activating ROS-FOXO pathway," Acta. Pharmacol. Sin., vol. 40, No. 11, 2019, pp. 1466-1479.

Neelapu, et al., "Axicabtagene Ciloleucel CAR T-Cell Therapy in Refractory Large B-Cell Lymphoma," N. Engl. J. Med., vol. 377, No. 26, 2017, pp. 2531-2544.

Scratchard, G. "The Attractions of Proteins for Small Molecules and Ions," Annals of the New York Academy of Sciences, vol. 51, 1949, pp. 660-672.

Tracey and Cerami, "Tumor necrosis factor: a pleiotropic cytokine and therapeutic target," Annu. Rev. Med., vol. 45, 1994, pp. 491-503.

Wiley and Winkles, "TWEAK, a member of the TNF superfamily, is a multifunctional cytokine that binds the TweakR/Fn14 receptor," Cytokine Growth Factor Rev., vol. 14, No. 3-4, 2003, pp. 241-249.

Benmebarek, et al, "Killing Mechanisms of Chimeric Antigen Receptor (CAR) T Cells", International Journal of Molecular Sciences, vol. 20, No. 6, Mar. 14, 2019, pp. 1-21.

Han, et al, "Effects of Rapamycin Combined with Cisplatin on Tumor Necrosis Factor TNF-[alpha] in MG-63 Cells", Cell Transplantation, vol. 29, Jan. 1, 2020, pp. 1-7.

Hu, et al, "Chimeric antigen receptor (CAR)-transduced natural killer cells in tumor immunotherapy", ACTA Pharmacologica Sinica, vol. 39, No. 2, Sep. 7, 2017, pp. 167-176.

Huye, et al, "Combining mTor Inhibitors With Rapamycin-resistant T Cells: A Two-pronged Approach to Tumor Elimination", Molecular Therapy, vol. 19, No. 12, Aug. 30, 2011.

Maecker, "TWEAK Attenuates the Transition from Innate to Adaptive Immunity", Cell, vol. 123, No. 5, Sep. 22, 2022, pp. 931-944.

Partial European Search Report mailed Mar. 14, 2024 for European Application No. 21780314.7, a foreign counterpart to U.S. Appl. No. 17/907,657, 23 pages.

Smith et al, "In situ programming of leukaemia-specific T cells using synthetic DNA nanocarriers", Nature Nanotechnology, vol. 12, No. 8. Apr. 17, 2017, pp. 813-820.

Watanabe, "Pancreatic cancer therapy with combined mesothelin-redirected chimeric antigen receptor T cells and cytokine-armed oncolytic adenoviruses", JCI Insight, vol. 3, No. 7, Apr. 5, 2018, pp. 1-17.

Wu, et al, "CD19 chimeric anitgen receptor-redirected T cells combined with epidermal growth factor receptor pathway substrate 8 peptide-derived dendritic cell vaccine in leukemia", Cytotherapy, vol. 21, No. 6, Jun. 1, 2019, pp. 659-670.

Moroz, "Imaging the efficacy of TRAIL-enhanced CAR T-cell immunotherapy", Molecular Imaging and Biology, vol. 18, No. 2, 2016, pp. S750-S751.

* cited by examiner

★ $CD33^{pos}$ + $chromium^{51}$ w/$CD33^{neg}$ ● $CD33^{neg}$ + $chromium^{51}$ w/$CD33^{pos}$ ■ $CD33^{pos}$ + $chromium^{51}$ w/$CD33^{pos}$ ◆ $CD33^{neg}$ + $chromium^{51}$ w/$CD33^{neg}$ % Cytotoxicity
Effector :Target Ratio
100:1
30:1
10:1
3:1
150
100
50
0
CD33pos + chromium51 w/CD33neg
CD33neg + chromium51 w/CD33pos
CD33pos + chromium51 w/CD33pos
CD33neg + chromium51 w/CD33neg ★ CD33pos + chromium51 w/CD33neg ● CD33neg + chromium51 w/CD33pos ■ CD33pos + chromium51 w/CD33pos ◆ CD33neg + chromium51 w/CD33neg

FIG. 6

| TNFRSF Members | Gene | Protein | Ligand | Potentiates or inhibits TNFα-induced cell death | Ligand to potentiate cell death |
|---|---|---|---|---|---|
| **1A** | *TNFRSF1A* | Tumor necrosis factor receptor 1 | TNFα | Potentiates | Membrane-bound TNFα |
| **1B** | *TNFRSF1B* | Tumor necrosis factor receptor 2 | TNFα | Potentiates | Membrane-bound TNFα |
| **3** | *LTBR* | CD18 | TNF-C | Potentiates | Membrane-bound TNF-C |
| **6** | *FAS* | CD95 | FasL, | Potentiates | FasL |
| **6B** | TNFRSF6B | Decoy receptor 3 | LIGHT, TL1A | Inhibits | Secreted antagonist antibody |
| **8** | TNFRSF8 | CD30 | CD153 | Potentiates | CD153 |
| **10A** | TNFRSF10A | Death receptor 4 | TRAIL | Potentiates | Membrane-bound TRAIL |
| **10B** | TNFRSF10B | Death receptor 5 | TRAIL | Potentiates | Membrane-bound TRAIL |
| **10C** | TNFRSF10C | Decoy receptor 1 | TRAIL | Inhibits | Secreted antagonist antibody |
| **10D** | TNFRSF10D | Decoy receptor 2 | TRAIL | Inhibits | Secreted antagonist antibody |
| **12A** | TNFRSF12A | TWEAK Receptor | TWEAK | Potentiates | Membrane-bound TWEAK or secreted Enavatuzuma b |
| **19** | TNFRSF19 | TROY | *Unknown* | Potentiates | Secreted agonist antibody |
| **21** | TNFRSF21 | Death receptor 6 | *Unknown* | Potentiates | Secreted agonist antibody |

FIG. 7
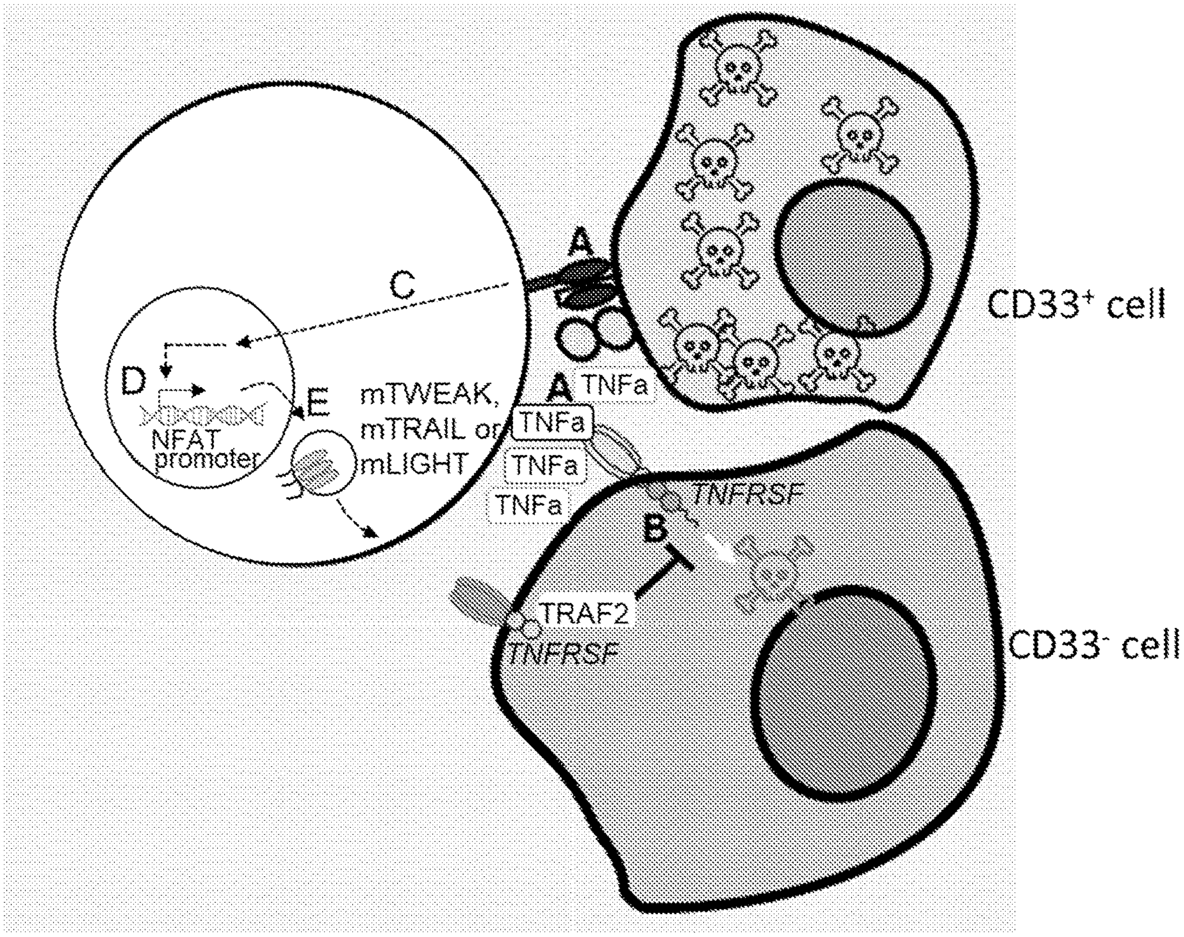
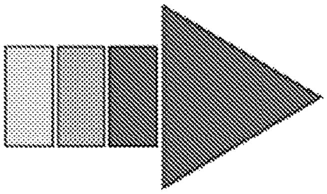

FIG. 9A

| Compound | Mechanism | Molecular weight (Da) | Solvent | Stock solution (µM) | Concentration in assay (µm) | Doi reference |
|---|---|---|---|---|---|---|
| **ASTX660 (Astex)** | XIAP/CIAP inhibitor | **539.68** | **DMSO** | **5000** | **10** | https://doi.org/10.1002/2211-5463.13096 |
| **AZD5582** | CIAP1,2 and XIAP inhibitor | **1015.29** | **DMSO** | **5000** | **0.2** | https://doi.org/10.1016/j.cellsig.2020.109654 |
| **Birinapant** (Medivir) | XIAP/CIAP1 inhibitor | **806.94** | **DMSO** | **10000** | **5** | https://doi.org/10.1158/2326-6066.CIR-18-0428 |
| **BV-6** | CIAP1,2 and XIAP inhibitor | **1205.57** | **DMSO** | **5000** | **5** | https://doi.org/10.1016/j.icms.2020.05.007 |
| **CUDC-427** (Curis) | pan-BIRC inhibitor | **564.7** | **DMSO** | **5000** | **1** | https://doi.org/10.1016/j.icms.2020.05.007 |
| **GDC-0152** | CIAP1,2 and XIAP inhibitor | **498.64** | **DMSO** | **5000** | **1** | https://doi.org/10.1016/j.icms.2020.05.007 |
| **KillerTRAIL** | TRAIL agonist | **24000** | **Water** | **0.5 mg/ml** | **8 ng/ml** | https://doi.org/10.1002/2211-5463.13096 |
| **LCL161 (Novartis)** | CIAP1 inhibitor | **500.63** | **DMSO** | **10000** | **5** | https://doi.org/10.1016/j.icms.2020.05.007 |

FIG. 9B
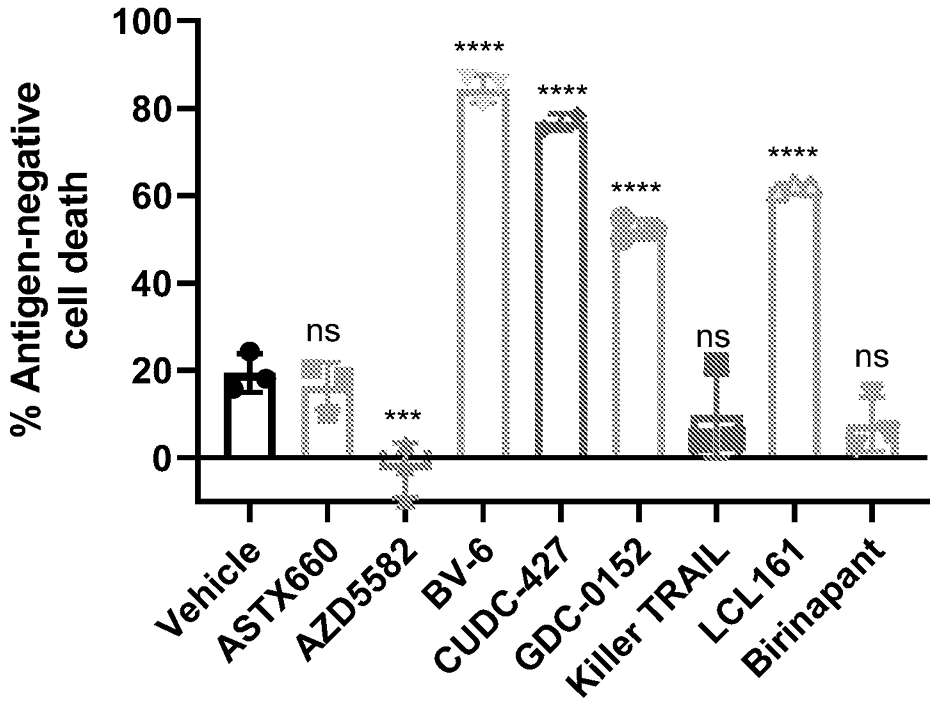
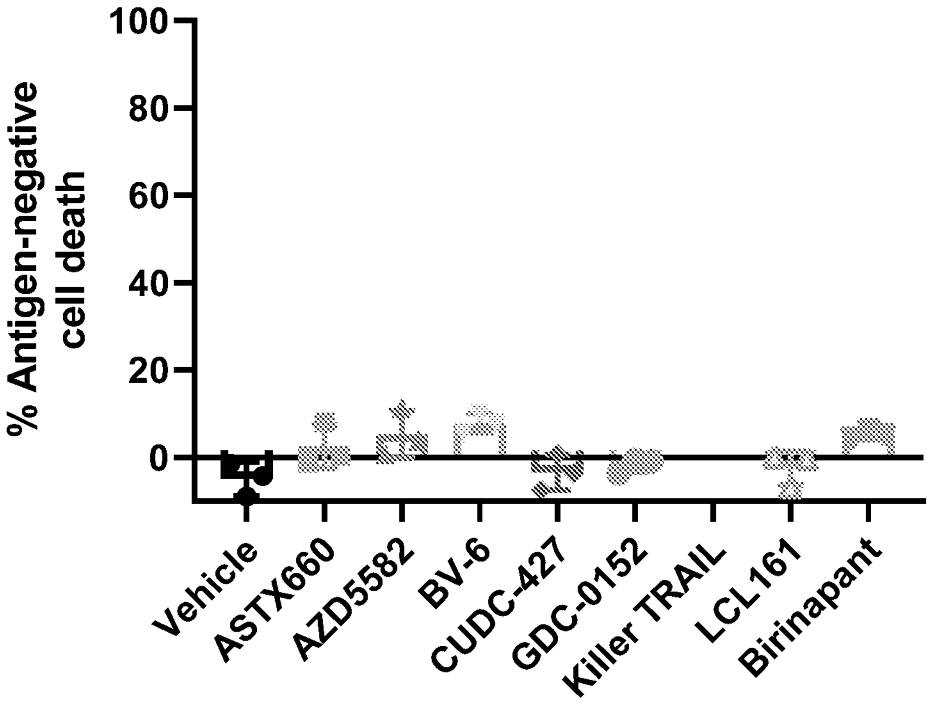

FIG. 10

| Small Molecule | Source | Inhibited Protein |
|---|---|---|
| Rocaglamide | (Traditional Chinese herbal medicine) | cFLIP |
| Sirolimus | Pfizer | |
| Emricasan | Novartis | Capsase 8 |
| BI 891065 | Boehringer Ingelheim | |
| DEBIO 1143 | Debiopharm | |
| APG-1387 | Ascentage Pharma Group Inc. | |
| HGS1029 | GlaxoSmithKline | |
| AEG35156 | Pharmascience Inc. | XIAP |

FIG. 11

IgG4 Hinge
ESKYGPPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAKGQPR
EPQVYTLPPSQEEMTKNQVSLTCLVKGFYPSDIAVEWESNGQPENNYKTTPPVLDSDGSFFLY
SRLTVDKSRWQEGNVFSCSVMHEALHNHYTQKSLSLSLGKM (SEQ ID NO: 125)

IgG4 Hinge coding sequence
GAGAGCAAGTACGGCCCTCCCTGCCCCCCTTGCCCTGCCCCCGAGTTCCTGGGCGGACC
CAGCGTGTTCCTGTTCCCCCCCAAGCCCAAGGACACCCTGATGATCAGCCGGACCCCCGA
GGTGACCTGTGTGGTGGTGGACGTGTCCCAGGAGGACCCCGAGGTCCAGTTCAACTGGT
ACGTGGACGGCGTGGAGGTGCACAACGCCAAGACCAAGCCCCGGGAGGAGCAGTTCAAT
AGCACCTACCGGGTGGTGTCCGTGCTGACCGTGCTGCACCAGGACTGGCTGAACGGCAA
GGAATACAAGTGTAAGGTGTCCAACAAGGGCCTGCCCAGCAGCATCGAGAAAACCATCAG
CAAGGCCAAGGGCCAGCCTCGGGAGCCCCAGGTGTACACCCTGCCCCCTAGCCAAGAGG
AGATGACCAAGAACCAGGTGTCCCTGACCTGCCTGGTGAAGGGCTTCTACCCCAGCGACA
TCGCCGTGGAGTGGGAGAGCAACGGCCAGCCCGAGAACAACTACAAGACCACCCCCCCT
GTGCTGGACAGCGACGGCAGCTTCTTCCTGTACAGCCGGCTGACCGTGGACAAGAGCCG
GTGGCAGGAGGGCAACGTCTTTAGCTGCTCCGTGATGCACGAGGCCCTGCACAACCACTA
CACCCAGAAGAGCCTGAGCCTGTCCCTGGGCAAGATG (SEQ ID NO: 126)

IgD Hinge
RWPESPKAQASSVPTAQPQAEGSLAKATTAPATTRNTGRGGEEKKKEKEKEEQEERETKTPE
CPSHTQPLGVYLLTPAVQDLWLRDKATFTCFVVGSDLKDAHLTWEVAGKVPTGGVEEGLLER
HSNGSQSQHSRLTLPRSLWNAGTSVTCTLNHPSLPPQRLMALREPAAQAPVKLSLNLLASSDP
PEAASWLLCEVSGFSPPNILLMWLEDQREVNTSGFAPARPPPQPGSTTFWAWSVLRVPAPPS
PQPATYTCVVSHEDSRTLLNASRSLEVSYVTDH (SEQ ID NO: 127)

IgD Hinge coding sequence
AGGTGGCCCGAAAGTCCCAAGGCCCAGGCATCTAGTGTTCCTACTGCACAGCCCCAGGCA
GAAGGCAGCCTAGCCAAAGCTACTACTGCACCTGCCACTACGCGCAATACTGGCCGTGGC
GGGGAGGAGAAGAAAAAGGAGAAAGAGAAAGAAGAACAGGAAGAGAGGGAGACCAAGAC
CCCTGAATGTCCATCCCATACCCAGCCGCTGGGCGTCTATCTCTTGACTCCCGCAGTACA
GGACTTGTGGCTTAGAGATAAGGCCACCTTTACATGTTTCGTCGTGGGCTCTGACCTGAAG
GATGCCCATTTGACTTGGGAGGTTGCCGGAAAGGTACCCACAGGGGGGGTTGAGGAAGG
GTTGCTGGAGCGCCATTCCAATGGCTCTCAGAGCCAGCACTCAAGACTCACCCTTCCGAG
ATCCCTGTGGAACGCCGGGACCTCTGTCACATGTACTCTAAATCATCCTAGCCTGCCCCCA
CAGCGTCTGATGGCCCTTAGAGAGCCAGCCGCCCAGGCACCAGTTAAGCTTAGCCTGAAT
CTGCTCGCCAGTAGTGATCCCCCAGAGGCCGCCAGCTGGCTCTTATGCGAAGTGTCCGGC
TTTAGCCCGCCCAACATCTTGCTCATGTGGCTGGAGGACCAGCGAGAAGTGAACACCAGC
GGCTTCGCTCCAGCCCGGCCCCCACCCCAGCCGGGTTCTACCACATTCTGGGCCTGGAG
TGTCTTAAGGGTCCCAGCACCACCTAGCCCCCAGCCAGCCACATACACCTGTGTTGTGTC
CCATGAAGATAGCAGGACCCTGCTAAATGCTTCTAGGAGTCTGGAGGTTTCCTACGTGACT
GACCATT (SEQ ID NO: 128)

IgG4 linker
ESKYGPPCPPCP (SEQ ID NO: 129)

Short Spacer
AATCTAAGTACGGACCGCCCTGCCCCCCTTGCCCT (SEQ ID NO: 130)

FIG. 11 cont'd

Intermediate Spacer
ESKYGPPCPPCPGQPREPQVYTLPPSQEEMTKNQVSLTCLVKGFYPSDIAVEWESNGQPENN
YKTTPPVLDSDGSFFLYSRLTVDKSRWQEGNVFSCSVMHEALHNHYTQKSLSLSLGK (SEQ ID NO: 131)

IgG4 hinge region, CH2 region, and CH3 region
ESKYGPPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAKGQPR
EPQVYTLPPSQEEMTKNQVSLTCLVKGFYPSDIAVEWESNGQPENNYKTTPPVLDSDGSFFLY
SRLTVDKSRWQEGNVFSCSVMHEALHNHYTQKSLSLSLGK (SEQ ID NO: 132)

C-type lectin
HKDSCYFLSDDVQTWQESKMACAAQNASLLKINNKNALEFIKSQSRSYDYWLGLSPEEDSTRG
MRVDNIINSSAWVIRNAPDLNNMYCGYINRLYVQYYHCTYKKRMIC (SEQ ID NO: 172)

CD28 transmembrane domain encoding sequences
ATGTTCTGGGTGCTGGTGGTGGTGGGCGGGGTGCTGGCCTGCTACAGCCTGCTGGTGAC
AGTGGCCTTCATCATCTTTTGG (SEQ ID NO: 133)

ATGTTCTGGGTGCTGGTGGTGGTCGGAGGCGTGCTGGCCTGCTACAGCCTGCTGGTCAC
CGTGGCCTTCATCATCTTTTGG (SEQ ID NO: 134)

ATGTTTTGGGTGCTGGTGGTGGTGGGCGGCGTGCTGGCGTGCTATAGCCTGCTGGTGAC
CGTGGCGTTTATTATTTTTTGG (SEQ ID NO: 135)

TTTTGGGTGCTGGTGGTGGTGGGCGGCGTGCTGGCGTGCTATAGCCTGCTGGTGACCGT
GGCGTTTATTATTTTT (SEQ ID NO: 136)

CD28 transmembrane domain sequences
MFWVLVVVGGVLACYSLLVTVAFIIFW (SEQ ID NO: 137)

FWVLVVVGGVLACYSLLVTVAFIIFW (SEQ ID NO: 138)

CD3z encoding sequences
CGGGTGAAGTTCAGCAGAAGCGCCGACGCCCCTGCCTACCAGCAGGGCCAGAATCAGCT
GTACAACGAGCTGAACCTGGGCAGAAGGGAAGAGTACGACGTCCTGGATAAGCGGAGAG
GCCGGGACCCTGAGATGGGCGGCAAGCCTCGGCGGAAGAACCCCCAGGAAGGCCTGTAT
AACGAACTGCAGAAAGACAAGATGGCCGAGGCCTACAGCGAGATCGGCATGAAGGGCGA
GCGGAGGCGGGGCAAGGGCCACGACGGCCTGTATCAGGGCCTGTCCACCGCCACCAAG
GATACCTACGACGCCCTGCACATGCAGGCCCTGCCCCCAAGG (SEQ ID NO: 139)

CGCGTGAAATTTAGCCGCAGCGCGGATGCGCCGGCGTATCAGCAGGGCCAGAACCAGCT
GTATAACGAACTGAACCTGGGCCGCCGCGAAGAATATGATGTGCTGGATAAACGCCGCGG
CCGCGATCCGGAAATGGGCGGCAAACCGCGCCGCAAAAACCCGCAGGAAGGCCTGTATA
ACGAACTGCAGAAAGATAAAATGGCGGAAGCGTATAGCGAAATTGGCATGAAAGGCGAAC
GCCGCCGCGGCAAAGGCCATGATGGCCTGTATCAGGGCCTGAGCACCGCGACCAAAGAT
ACCTATGATGCGCTGCATATGCAGGCGCTGCCGCCGCGC (SEQ ID NO: 140)

FIG. 11 cont'd

GAACTGCGCGTGAAATTTAGCCGCAGCGCGGATGCGCCGGCGTATCAGCAGGGCCAGAA
CCAGCTGTATAACGAACTGAACCTGGGCCGCCGCGAAGAATATGATGTGCTGGATAAACG
CCGCGGCCGCGATCCGGAAATGGGCGGCAAACCGCGCCGCAAAAACCCGCAGGAAGGC
CTGTATAACGAACTGCAGAAAGATAAAATGGCGGAAGCGTATAGCGAAATTGGCATGAAAG
GCGAACGCCGCCGCGGCAAAGGCCATGATGGCCTGTATCAGGGCCTGAGCACCGCGACC
AAAGATACCTATGATGCGCTGCATATGCAGGCGCTGCCGCCGCGC (SEQ ID NO: 141)

CD3z sequences
RVKFSRSADAPAYQQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR (SEQ ID NO: 142)

ELRVKFSRSADAPAYQQGQNQLYNELNLGRREEYDVLDKRRGRDPEMGGKPRRKNPQEGLY
NELQKDKMAEAYSEIGMKGERRRGKGHDGLYQGLSTATKDTYDALHMQALPPR (SEQ ID NO: 143)

4-1BB encoding sequences
GTGAAACGGGGCAGAAAGAAACTCCTGTATATATTCAAACAACCATTTATGAGACCAGTAC
AAACTACTCAAGAGGAAGATGGCTGTAGCTGCCGATTTCCAGAAGAAGAAGAAGGAGGAT
GTGAACTG (SEQ ID NO: 144)

GTGAAACGCGGCCGCAAAAAACTGCTGTATATTTTTAAACAGCCGTTTATGCGCCCGGTGC
AGACCACCCAGGAAGAAGATGGCTGCAGCTGCCGCTTTCCGGAAGAAGAAGAAGGCGGC
TGCGAACTG (SEQ ID NO: 145)

GTGAAACGCGGCCGCAAAAAACTGCTGTATATTTTTAAACAGCCGTTTATGCGCCCGGTGC
AGACCACCCAGGAAGAAGATGGCTGCAGCTGCCGCTTTCCGGAAGAAGAAGAAGGCGGC
TGC (SEQ ID NO: 146)

4-1BB
VKRGRKKLLYIFKQPFMRPVQTTQEEDGCSCRFPEEEEGGCEL (SEQ ID NO: 147)

4-1BB_CPD
VKRGRKKLLYIFKQPFMRPVQTTQEEDGCSCRFPEEEEGGC (SEQ ID NO: 148)

Linker coding sequence
GGAGGAGGAGGCAGCGGCGGAGGAGGCTCCGGAGGCGGCGGCTCTGGCGGCGGCGGC
AGC (SEQ ID NO: 173)

Thosea asigna virus 2A (T2A) peptide
GSGEGRGSLLTCGDVEENPGP (SEQ ID NO: 149)

Porcine teschovirus-1 2A (P2A) peptide
GSGATNFSLLKQAGDVEENPGP (SEQ ID NO: 150)

FIG. 11 cont'd

Equine rhinitis A virus (ERAV) 2A (E2A) peptide
GSGQCTNYALLKLAGDVESNPGP (SEQ ID NO: 151)

Foot-and-mouth disease virus 2A (F2A) peptide
GSGVKQTLNFDLLKLAGDVESNPGP (SEQ ID NO: 152)

Variants of T2A
GEGRGSLLTCGDVEENPGP (SEQ ID NO: 153)

GGGEGRGSLLTCGDVEENPGP (SEQ ID NO: 154)

EGFRt
RKVCNGIGIGEFKDSLSINATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGLRSLKEISDGDVIISGNK
NLCYANTINWKKLFGTSGQKTKIISNRGENSCKATGQVCHALCSPEGCWGPEPRDCVSCRNV
SRGRECVDKCNLLEGEPREFVENSECIQCHPECLPQAMNITCTGRGPDNCIQCAHYIDGPHCV
KTCPAGVMGENNTLVWKYADAGHVCHLCHPNCTYGCTGPGLEGCPTNGPKIPSIATGMVGAL
LLLLVVALGIGLFM (SEQ ID NO: 155)

EGFR
RKVCNGIGIGEFKDSLSINATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGLRSLKEISDGDVIISGNK
NLCYANTINWKKLFGTSGQKTKIISNRGENSCKATGQVCHALCSPEGCWGPEPRDCVSCRNV
SRGRECVDKCNLLEGEPREFVENSECIQCHPECLPQAMNITCTGRGPDNCIQCAHYIDGPHCV
KTCPAGVMGENNTLVWKYADAGHVCHLCHPNCTYGCTGPGLEGCPTNGPKIPS (SEQ ID NO: 156)

TM_EGFR
IATGMVGALLLLLVVALGIGLFM (SEQ ID NO: 157)

1H7 scFv coding sequence:
ATGCTGCTGCTCGTGACCAGCCTGCTGCTGTGCGAACTGCCCCACCCTGCCTTTCTGCTG
ATCCCCCAAGTACAACTTCAACAAAGTGGAGCCGAACTGGTAAAACCCGGAGCGTCTGTG
AAGATTAGTTGCAAGGCATCCGGTTACGCCTTCTCAAATTATTGGATGAACTGGGTAAAGC
AGCGGCCCGGAAAGGGTCTCGAGTGGATTGGGCAAATCAACCCAGGGGACGGGGATACG
AACTACAACGGTAAGTTCAAAGGCAAGGCTACGTTGACGGCTGATAAGAGCTCAAGCACC
GCTTACATGCAGTTGTCTTCTTTGACAAGTGAGGATAGTGCCGTTTACTTCTGCGCCCGAG
AGGACCGAGATTATTTTGATTATTGGGGCCAGGGAACAACTCTCACCGTCAGCTCCGGAG
GCGGAGGATCTGGCGGAGGGGGCTCTGGAGGAGGAGGATCTGATATTCAGATGACCCAA
ACTACGAGTTCCCTGTCTGCCAGCCTTGGCGACCGGGTCACAATTAGTTGCAGGGCTTCT
CAGGATATCAACTACTATTTGAACTGGTACCAGCAGAAACCTGATGGGACGGTCAAACTTC
TCATCTACTATTCATCCAGACTGCACAGTGGCGTACCGTCTAGATTCTCAGGAAGCGGCAG
TGGTACGGATTTTAGTCTTACCATTAGTAATCTGGAACAGGAGGACATCGCCACGTATTTTT
GCCAGCAGGATGACGCACTGCCCTATACCTTCGGCGGAGGCACTAAGTTGGAGATAAAA
(SEQ ID NO: 158)

FIG. 11 cont'd

Anti-CD19 scFv
DIQMTQTTSSLSASLGDRVTISCRASQDISKYLNWYQQKPDGTVKLLIYHTSRLHSGVPSRFSG
SGSGTDYSLTISNLEQEDIATYFCQQGNTLPYTFGGGTKLEITGSTSGSGKPGSGEGSTKGEVK
LQESGPGLVAPSQSLSVTCTVSGVSLPDYGVSWIRQPPRKGLEWLGVIWGSETTYYNSALKSR
LTIIKDNSKSQVFLKMNSLQTDDTAIYYCAKHYYYGGSYAMDYWGQGTSVTVSS (SEQ ID NO: 174)

Anti-CD19 scFv coding sequence
GACATCCAGATGACCCAGACCACCTCCAGCCTGAGCGCCAGCCTGGGCGACCGGGTGAC
CATCAGCTGCCGGGCCAGCCAGGACATCAGCAAGTACCTGAACTGGTATCAGCAGAAGCC
CGACGGCACCGTCAAGCTGCTGATCTACCACACCAGCCGGCTGCACAGCGGCGTGCCCA
GCCGGTTTAGCGGCAGCGGCTCCGGCACCGACTACAGCCTGACCATCTCCAACCTGGAA
CAGGAAGATATCGCCACCTACTTTTGCCAGCAGGGCAACACACTGCCCTACACCTTTGGC
GGCGGAACAAAGCTGGAAATCACCGGCAGCACCTCCGGCAGCGGCAAGCCTGGCAGCGG
CGAGGGCAGCACCAAGGGCGAGGTGAAGCTGCAGGAAAGCGGCCCTGGCCTGGTGGCC
CCCAGCCAGAGCCTGAGCGTGACCTGCACCGTGAGCGGCGTGAGCCTGCCCGACTACGG
CGTGAGCTGGATCCGGCAGCCCCCCAGGAAGGGCCTGGAATGGCTGGGCGTGATCTGGG
GCAGCGAGACCACCTACTACAACAGCGCCCTGAAGAGCCGGCTGACCATCATCAAGGACA
ACAGCAAGAGCCAGGTGTTCCTGAAGATGAACAGCCTGCAGACCGACGACACCGCCATCT
ACTACTGCGCCAAGCACTACTACTACGGCGGCAGCTACGCCATGGACTACTGGGGCCAGG
GCACCAGCGTGACCGTGAGCAGC (SEQ ID NO: 159)

TWEAK [Homo sapiens], GenBank: BAE16557.1
MAARRSQRRRGRRGEPGTALLVPLALGLGLALACLGLLLAVVSLGSRASLSAQEPAQEELVAE
EDQDPSELNPQTEESQDPAPFLNRLVRPRRSAPKGRKTRARRAIAAHYEVHPRPGQDGAQAG
VDGTVSGWEEARINSSSPLRYNRQIGEFIVTRAGLYYLYCQVHFDEGKAVYLKLDLLVDGVLAL
RCLEEFSATAASSLGPQLRLCQVSGLLALRPGSSLRIRTLPWAHLKAAPFLTYFGLFQVH (SEQ ID NO: 160)

LAMP [Homo sapiens], GenBank: CAA06691.1
MPRQLSAAAALFASLAVILHDGSQMRAKAFPETRDYSQPTAAATVQDIKKPVQQPAKQAPHQT
LAARFMDGHITFQTAATVKIPTTTPATTKNTATTSPITYTLVTTQATPNNSHTAPPVTEVTVGPSL
APYSLPPTITPPAHTTGTSSSTVSHTTGNTTQPSNQTTLPATLSIALHKSTTGQKPVQPTHAPGT
TAAAHNTTRTAAPASTVPGPTLAPQPSSVKTGIYQVLNGSRLCIKAEMGIQLIVQDKESVFSPRR
YFNIDPNATQASGNCGTRKSNLLLNFQGGFVNLTFTKDEESYYISEVGAYLTVSDPETIYQGIKH
AVVMFQTAVGHSFKCVSEQSLQLSAHLQVKTTDVQLQAFDFEDDHFGNVDECSSDYTIVLPVI
GAIVVGLCLMGMGVYKIRLRCQSSGYQRI (SEQ ID NO: 161)

TRAIL [Homo sapiens], UniProtKB/Swiss-Prot: P50591.1
MAMMEVQGGPSLGQTCVLIVIFTVLLQSLCVAVTYVYFTNELKQMQDKYSKSGIACFLKEDDSY
WDPNDEESMNSPCWQVKWQLRQLVRKMILRTSEETISTVQEKQQNISPLVRERGPQRVAAHI
TGTRGRSNTLSSPNSKNEKALGRKINSWESSRSGHSFLSNLHLRNGELVIHEKGFYYIYSQTYF
RFQEEIKENTKNDKQMVQYIYKYTSYPDPILLMKSARNSCWSKDAEYGLYSIYQGGIFELKEND
RIFVSVTNEHLIDMDHEASFFGAFLVG (SEQ ID NO: 162)

FIG. 11 cont'd

Tumor necrosis factor ligand superfamily member 14, soluble form (LIGHT) [Homo sapiens], UniProtKB/Swiss-Prot: O43557.2
MEESVVRPSVFVVDGQTDIPFTRLGRSHRRQSCSVARVGLGLLLLLMGAGLAVQGWFLLQLH
WRLGEMVTRLPDGPAGSWEQLIQERRSHEVNPAAHLTGANSSLTGSGGPLLWETQLGLAFLR
GLSYHDGALVVTKAGYYYIYSKVQLGGVGCPLGLASTITHGLYKRTPRYPEELELLVSQQSPCG
RATSSSRVWWDSSFLGGVVHLEAGEKVVVRVLDERLVRLRDGTRSYFGAFMV (SEQ ID NO: 175)

1H7-long-41bb-3z-T-CD19t Top Strand
GGATCTGCGATCGCTCCGGTGCCCGTCAGTGGGCAGAGCGCACATCGCCCACAGTCCC
CGAGAAGTTGGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGGAG
AACCGTATATAAGTGCAGTAGTCGCCGTGAACGTTCTTTTTCGCAACGGGTTTGCCGCCA
GAACACAGCTGAAGCTTCGAGGGGCTCGCATCTCTCCTTCACGCGCCCGCCGCCCTACC
TGAGGCCGCCATCCACGCCGGTTGAGTCGCGTTCTGCCGCCTCCCGCCTGTGGTGCCTC
CTGAACTGCGTCCGCCGTCTAGGTAAGTTTAAAGCTCAGGTCGAGACCGGGCCTTTGTC
CGGCGCTCCCTTGGAGCCTACCTAGACTCAGCCGGCTCTCCACGCTTTGCCTGACCCTG
CTTGCTCAACTCTACGTCTTTGTTTCGTTTTCTGTTCTGCGCCGTTACAGATCCAAGCTGT
GACCGGCGCCTACGGCTAGCCACCATGCTGCTGCTCGTGACCAGCCTGCTGCTGTGCGA
ACTGCCCCACCCTGCCTTTCTGCTGATCCCC*CAAGTACAACTTCAACAAAGTGGAGCCGAA*
*CTGGTAAAACCCGGAGCGTCTGTGAAGATTAGTTGCAAGGCATCCGGTTACGCCTTCTCAA*
*ATTATTGGATGAACTGGGTAAAGCAGCGGCCCGGAAAGGGTCTCGAGTGGATTGGGCAAA*
*TCAACCCAGGGGACGGGGATACGAACTACAACGGTAAGTTCAAAGGCAAGGCTACGTTGA*
*CGGCTGATAAGAGCTCAAGCACCGCTTACATGCAGTTGTCTTCTTTGACAAGTGAGGATAG*
*TGCCGTTTACTTCTGCGCCCGAGAGGACCGAGATTATTTTGATTATTGGGGCCAGGGAACA*
*ACTCTCACCGTCAGCTCCGGAGGCGGAGGATCTGGCGGAGGGGGCTCTGGAGGAGGAG*
*GATCTGATATTCAGATGACCCAAACTACGAGTTCCCTGTCTGCCAGCCTTGGCGACCGGGT*
*CACAATTAGTTGCAGGGCTTCTCAGGATATCAACTACTATTTGAACTGGTACCAGCAGAAA*
*CCTGATGGGACGGTCAAACTTCTCATCTACTATTCATCCAGACTGCACAGTGGCGTACCGT*
*CTAGATTCTCAGGAAGCGGCAGTGGTACGGATTTTAGTCTTACCATTAGTAATCTGGAACA*
*GGAGGACATCGCCACGTATTTTTGCCAGCAGGATGACGCACTGCCCTATACCTTCGGCGG*
*AGGCACTAAGTTGGAGATAAAA*GAGTCTAAGTACGGACCGCCTTGCCCACCGTGCCCAG
CACCACCTGTGGCAGGACCGTCAGTCTTCCTCTTCCCACCAAAACCCAAGGACACCCTGA
TGATCAGCCGGACCCCCGAGGTGACCTGCGTGGTGGTGGACGTGAGCCAGGAAGATCCC
GAGGTCCAGTTCAATTGGTACGTGGACGGCGTGGAAGTGCACAACGCCAAGACCAAGCCC
AGAGAGGAACAGTTCCAAAGCACCTACCGGGTGGTGTCTGTGCTGACCGTGCTGCACCAG
GACTGGCTGAACGGCAAAGAATACAAGTGCAAGGTGTCCAACAAGGGCCTGCCCAGCAGC
ATCGAAAAGACCATCAGCAAGGCCAAGGGCCAGCCTCGCGAGCCCCAGGTGTACACCCT
GCCTCCCTCCCAGGAAGAGATGACCAAGAACCAGGTGTCCCTGACCTGCCTGGTGAAGG
GCTTCTACCCCAGCGACATCGCCGTGGAGTGGGAGAGCAACGGCCAGCCTGAGAACAAC
TACAAGACCACCCCTCCCGTGCTGGACAGCGACGGCAGCTTCTTCCTGTACAGCCGGCTG
ACCGTGGACAAGAGCCGGTGGCAGGAAGGCAACGTCTTTAGCTGCAGCGTGATGCACGA
GGCCCTGCACAACCACTACACCCAGAAGAGCCTGAGCCTGTCCCTGGGCAAG*ATG*TTCTG
GGTGCTGGTGGTGGTGGGCGGGGTGCTGGCCTGCTACAGCCTGCTGGTGACAGTGGCC
TTCATCATCTTTTGGGTGAAACGGGGCAGAAAGAAACTCCTGTATATATTCAAACAACCATT
TATGAGACCAGTACAAACTACTCAAGAGGAAGATGGCTGTAGCTGCCGATTTCCAGAAGAA
GAAGAAGGAGGATGTGAACTG*CGGGTGAAGTTCAGCAGAAGCGCCGACGCCCCTGCCTA*
*CCAGCAGGGCCAGAATCAGCTGTACAACGAGCTGAACCTGGGCAGAAGGGAAGAGTACG*

FIG. 11 cont'd

*ACGTCCTGGATAAGCGGAGAGGCCGGGACCCTGAGATGGGCGGCAAGCCTCGGCGGAA*
*GAACCCCCAGGAAGGCCTGTATAACGAACTGCAGAAAGACAAGATGGCCGAGGCCTACAG*
*CGAGATCGGCATGAAGGGCGAGCGGAGGCGGGGCAAGGGCCACGACGGCCTGTATCAG*
*GGCCTGTCCACCGCCACCAAGGATACCTACGACGCCCTGCACATGCAGGCCCTGCCCCC*
*AAGG*CTCGAGGGCGGCGGAGAGGGCAGAGGAAGTCTTCTAACATGCGGTGACGTGGAG
GAGAATCCAGGCCCTAGGATGCCACCTCCAAGACTCCTCTTCTTCCTCCTCTTCCTGACAC
CAATGGAAGTCAGGCCTGAGGAACCTCTAGTGGTGAAGGTGGAAGAGGGAGATAACGCTG
TGTTACAGTGCCTCAAGGGAACCTCAGATGGACCCACTCAGCAGCTGACCTGGTCTCGGG
AGTCTCCGCTTAAACCCTTCCTGAAACTCAGCCTTGGACTGCCAGGTCTGGGAATCCACAT
GAGGCCACTGGCTATCTGGCTGTTCATCTTCAACGTCTCTCAACAGATGGGAGGCTTCTAC
CTGTGTCAGCCTGGACCACCTTCTGAGAAGGCATGGCAGCCTGGTTGGACAGTCAATGTG
GAGGGTTCTGGTGAGCTGTTCCGGTGGAATGTTTCGGACCTAGGTGGACTGGGATGTGGT
CTGAAGAACAGGTCCTCAGAGGGACCTAGCTCTCCTTCCGGGAAGCTCATGAGCCCCAAG
CTGTATGTGTGGGCCAAAGACCGCCCTGAGATCTGGGAGGGAGAGCCTCCGTGTGTCCC
ACCGAGGGACAGCCTGAACCAGAGCCTCAGCCAGGACCTCACCATGGCCCCTGGCTCCA
CACTCTGGCTGTCCTGTGGGGTACCCCCTGACTCTGTGTCCAGGGGCCCCCTCTCCTGGA
CCCATGTGCACCCCAAGGGGCCTAAGTCATTGCTGAGCCTAGAGCTGAAGGACGATCGCC
CTGCCAGAGATATGTGGGTAATGGAGACGGGTCTGTTGTTGCCCCGGGCCACAGCTCAAG
ACGCTGGAAAGTATTATTGTCACCGTGGCAACCTGACCATGTCATTCCACCTGGAGATCAC
TGCTCGGCCAGTACTATGGCACTGGCTGCTGAGGACTGGTGGCTGGAAGGTCTCAGCTGT
GACTTTGGCTTATCTGATCTTCTGCCTGTGTTCCCTTGTGGGCATTCTTCATCTTCAAAGAG
CCCTGGTCCTGAGGAGGAAAAGATGA (SEQ ID NO: 176)

Within the above sequence, EF1p is the first bold sequence; the sequence encoding GM-CSFR signal peptide is the first underlined sequence; the sequence encoding 1H7_HvLv is the first italicized sequence; the sequence encoding IgG4hinge S10P is the second bold sequence; the sequence encoding IgG4-long (2NQ) is the second underlined sequence; the sequence encoding a glycosylation site is the second italicized sequence; the sequence encoding CD28TM the third bold sequence; the sequence encoding 4-1BB is the third underlined sequence; the sequences encoding CD3z is the third italicized sequence; the sequence encoding T2A is the fourth bold sequence; and tCD19-Fully sequenced is the fourth underlined sequence section of the sequence above.

1H7-sh-41bb-3z-T-CD19t Top Strand
GGATCTGCGATCGCTCCGGTGCCCGTCAGTGGGCAGAGCGCACATCGCCCACAGTCCC
CGAGAAGTTGGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGGAG
AACCGTATATAAGTGCAGTAGTCGCCGTGAACGTTCTTTTTCGCAACGGGTTTGCCGCCA
GAACACAGCTGAAGCTTCGAGGGGCTCGCATCTCTCCTTCACGCGCCCGCCGCCCTACC
TGAGGCCGCCATCCACGCCGGTTGAGTCGCGTTCTGCCGCCTCCCGCCTGTGGTGCCTC
CTGAACTGCGTCCGCCGTCTAGGTAAGTTTAAAGCTCAGGTCGAGACCGGGCCTTTGTC
CGGCGCTCCCTTGGAGCCTACCTAGACTCAGCCGGCTCTCCACGCTTTGCCTGACCCTG
CTTGCTCAACTCTACGTCTTTGTTTCGTTTTCTGTTCTGCGCCGTTACAGATCCAAGCTGT
GACCGGCGCCTACGGCTAGCCACCATGCTGCTGCTCGTGACCAGCCTGCTGCTGTGCGA
ACTGCCCCACCCTGCCTTTCTGCTGATCCCC*CAAGTACAACTTCAACAAAGTGGAGCCGAA*
*CTGGTAAAACCCGGAGCGTCTGTGAAGATTAGTTGCAAGGCATCCGGTTACGCCTTCTCAA*
*ATTATTGGATGAACTGGGTAAAGCAGCGGCCCGGAAAGGGTCTCGAGTGGATTGGGCAAA*
*TCAACCCAGGGGACGGGGATACGAACTACAACGGTAAGTTCAAAGGCAAGGCTACGTTGA*
*CGGCTGATAAGAGCTCAAGCACCGCTTACATGCAGTTGTCTTCTTTGACAAGTGAGGATAG*

FIG. 11 cont'd

*TGCCGTTTACTTCTGCGCCCGAGAGGACCGAGATTATTTTGATTATTGGGGCCAGGGAACA*
*ACTCTCACCGTCAGCTCCGGAGGCGGAGGATCTGGCGGAGGGGGCTCTGGAGGAGGAG*
*GATCTGATATTCAGATGACCCAAACTACGAGTTCCCTGTCTGCCAGCCTTGGCGACCGGGT*
*CACAATTAGTTGCAGGGCTTCTCAGGATATCAACTACTATTTGAACTGGTACCAGCAGAAA*
*CCTGATGGGACGGTCAAACTTCTCATCTACTATTCATCCAGACTGCACAGTGGCGTACCGT*
*CTAGATTCTCAGGAAGCGGCAGTGGTACGGATTTTAGTCTTACCATTAGTAATCTGGAACA*
*GGAGGACATCGCCACGTATTTTTGCCAGCAGGATGACGCACTGCCCTATACCTTCGGCGG*
*AGGCACTAAGTTGGAGATAAAA*GAGTCTAAGTACGGACCGCCCTGCCCCCCTTGCCCTAT
GTTCTGGGTGCTGGTGGTGGTCGGAGGCGTGCTGGCCTGCTACAGCCTGCTGGTCACCG
TGGCCTTCATCATCTTTTGGGTG*AAACGGGGCAGAAAGAAACTCCTGTATATATTCAAACAA*
*CCATTTATGAGACCAGTACAAACTACTCAAGAGGAAGATGGCTGTAGCTGCCGATTTCCAG*
*AAGAAGAAGAAGGAGGATGTGAACTG*CGGGTGAAGTTCAGCAGAAGCGCCGACGCCCCT
GCCTACCAGCAGGGCCAGAATCAGCTGTACAACGAGCTGAACCTGGGCAGAAGGGAAG
AGTACGACGTCCTGGATAAGCGGAGAGGCCGGGACCCTGAGATGGGCGGCAAGCCTCG
GCGGAAGAACCCCCAGGAAGGCCTGTATAACGAACTGCAGAAAGACAAGATGGCCGAG
GCCTACAGCGAGATCGGCATGAAGGGCGAGCGGAGGCGGGGCAAGGGCCACGACGGC
CTGTATCAGGGCCTGTCCACCGCCACCAAGGATACCTACGACGCCCTGCACATGCAGGC
CCTGCCCCCAAGGCTCGAGGGCGGCGGAGAGGGCAGAGGAAGTCTTCTAACATGCGGTG
ACGTGGAGGAGAATCCAGGCCCTAGG*ATGCCACCTCCAAGACTCCTCTTCTTCCTCCTCTT*
*CCTGACACCAATGGAAGTCAGGCCTGAGGAACCTCTAGTGGTGAAGGTGGAAGAGGGAG*
*ATAACGCTGTGTTACAGTGCCTCAAGGGAACCTCAGATGGACCCACTCAGCAGCTGACCT*
*GGTCTCGGGAGTCTCCGCTTAAACCCTTCCTGAAACTCAGCCTTGGACTGCCAGGTCTGG*
*GAATCCACATGAGGCCACTGGCTATCTGGCTGTTCATCTTCAACGTCTCTCAACAGATGGG*
*AGGCTTCTACCTGTGTCAGCCTGGACCACCTTCTGAGAAGGCATGGCAGCCTGGTTGGAC*
*AGTCAATGTGGAGGGTTCTGGTGAGCTGTTCCGGTGGAATGTTTCGGACCTAGGTGGACT*
*GGGATGTGGTCTGAAGAACAGGTCCTCAGAGGGACCTAGCTCTCCTTCCGGGAAGCTCAT*
*GAGCCCCAAGCTGTATGTGTGGGCCAAAGACCGCCCTGAGATCTGGGAGGGAGAGCCTC*
*CGTGTGTCCCACCGAGGGACAGCCTGAACCAGAGCCTCAGCCAGGACCTCACCATGGCC*
*CCTGGCTCCACACTCTGGCTGTCCTGTGGGGTACCCCCTGACTCTGTGTCCAGGGGCCCC*
*CTCTCCTGGACCCATGTGCACCCCAAGGGGCCTAAGTCATTGCTGAGCCTAGAGCTGAAG*
*GACGATCGCCCTGCCAGAGATATGTGGGTAATGGAGACGGGTCTGTTGTTGCCCCGGGC*
*CACAGCTCAAGACGCTGGAAAGTATTATTGTCACCGTGGCAACCTGACCATGTCATTCCAC*
*CTGGAGATCACTGCTCGGCCAGTACTATGGCACTGGCTGCTGAGGACTGGTGGCTGGAAG*
*GTCTCAGCTGTGACTTTGGCTTATCTGATCTTCTGCCTGTGTTCCCTTGTGGGCATTCTTCA*
*TCTTCAAAGAGCCCTGGTCCTGAGGAGGAAAAGATGA* (SEQ ID NO: 177)

Within the above sequence, EF1a promoter is the first bold sequence; the sequence encoding GM-CSFR signal peptide is the first underlined sequence; the sequence encoding 1H7_HvLv is the first italicized sequence; the sequence encoding IgG4hinge S10P is the second bold sequence; the sequence encoding CD28-TM is the second underlined sequence; the sequence encoding 4-1BB is the second italicized sequence; the sequences encoding CD3Z is the third bold sequence ; the sequence encoding T2A is the third underlined sequence; and tCD19-Fully sequenced is the third italicized sequence section of the sequence above.

Extracellular Domain of Human TRAIL:
SEETISTVQEKQQNISPLVRERGPQRVAAHITGTRGRSNTLSSPNSKNEKALGRKINSWESSRS GHSFLSNLHLRNGELVIHEKGFYYIYSQTYFRFQEEIKENTKNDKQMVQYIYKYTSYPDPILLMK SARNSCWSKDAEYGLYSIYQGGIFELKENDRIFVSVTNEHLIDMDHEASFFGAFLVG (SEQ ID NO: 178)

AUGMENTING ANTIGEN-NEGATIVE CELL DEATH IN ANTIGEN-TARGETED IMMUNOTHERAPIES

CROSS-REFERENCE TO RELATED APPLICATIONS

This application is a U.S. National Phase Application based on International Patent Application No. PCT/US2021/025260, filed on Mar. 31, 2021, which claims priority to U.S. Provisional Patent Application No. 63/003,209 filed Mar. 31, 2020, each of which is incorporated herein by reference in its entirety.

REFERENCE TO SEQUENCE LISTING

The Sequence Listing associated with this application is provided in text format in lieu of a paper copy, and is hereby incorporated by reference into the specification. The name of the text file containing the Sequence Listing is 2RS6758_ST25.txt. The text is 85.7 KB, was created on Sep. 27, 2022, and is being submitted electronically via Patent Center.

FIELD OF THE DISCLOSURE

The current disclosure provides combination therapies that include (i) an immune cell that expresses a chimeric antigen receptor (CAR) or similar molecule and (ii) a compound that preserves or potentiates the in vivo actions of tumor necrosis factor alpha (TNFα) against cancer cells. The compound can be a small molecule or a molecule that affects gene or protein expression by an immune cell. The combination therapies result in the killing of antigen-negative cells in the vicinity of immunotherapy targeted-antigen-positive cells reducing the survivability of escape variants and providing other benefits.

BACKGROUND OF THE DISCLOSURE

According to the World Health Organization, cancer is the second leading cause of death globally, and was responsible for an estimated 9.6 million deaths in 2018. For many years, the chosen treatments for cancer have been surgery, chemotherapy, and radiation therapy. In recent years, more targeted therapies have emerged to specifically target cancer cells by identifying and exploiting specific molecular changes seen primarily in those cells. For example, significant progress has been made in genetically engineering T cells of the immune system to target and kill unwanted cell types, such as cancer cells. Many of these T cells have been genetically engineered to express a chimeric antigen receptor (CAR). CARs are proteins including several distinct subcomponents that allow the genetically modified T cells to recognize and kill cancer cells. The subcomponents include at least an extracellular component and an intracellular component. The extracellular component includes a binding domain that specifically binds an antigen that is preferentially present on the surface of unwanted cells. When the binding domain binds such antigens, the intracellular component signals the T cell to destroy the bound cell. CARs additionally include a transmembrane domain that can link the extracellular component to the intracellular component, and other subcomponents that can increase the CAR's function. For example, the inclusion of one or more linker sequences, such as a spacer region, can allow the CAR to have additional conformational flexibility, often increasing the binding domain's ability to bind the targeted cell antigen.

Clinical trials with CAR-expressing T cells (CAR-T) have shown positive responses in patients with refractory large B-cell lymphoma when conventional treatments had failed (Neelapu, et al 2017 N Engl J Med 377:2531-2544). However, while genetically engineered CAR-T cells successfully result in cancer cell destruction, they have failed to provide prolonged anti-cancer activity in vivo for some indications. For example, antigen-negative relapse is a common cause of treatment failure following antigen-directed immunotherapy.

Tumor necrosis factor-alpha (TNFα) regulates cellular functions including apoptosis, immune responses, and cell growth and differentiation. In the vicinity of cancer cells, TNFα promoters cancer cell death. The TNFα pathway can be modulated by other members of the tumor necrosis factor receptor superfamily (TNFRSF) members to potentiate or inhibit TNFα-induced cell death. Cellular inhibitor of apoptosis proteins (cIAPs) can also be in the vicinity of cancer cells and conversely protect the cancer cells from the cell-killing effects of TNFα. As a result, therapeutic cIAP antagonists that reduce or block the actions of cIAPs have been developed.

SUMMARY OF THE DISCLOSURE

The current disclosure provides administration of an immunotherapy, such as a CAR-expressing immune cell in combination with a compound that potentiates or preserves the in vivo cell killing actions of TNFα. As shown herein, these combination therapies allow the killing of antigen-positive cells that are bound by a CAR or similar molecule. Potentiating or preserving the actions of TNFα also allows effective killing of antigen-negative cancer cells in the area of the targeted antigen-positive cells, thus reducing the survivability of escape variants among other benefits.

A compound that potentiates or preserves the in vivo cell killing actions of TNFα is referred to herein as a TNFα signal potentiator. In particular embodiments, TNFα signal potentiators include molecules that activate tumor necrosis factor receptor superfamily (TNFRSF) members that potentiate TNFα signaling pathway members. In particular embodiments, TNFα signal potentiators include molecules that inhibit TNFSRF members that inhibit TNFα signaling pathway members. In particular embodiments, the molecules can include genetic engineering molecules that knock-in TNFRSF members that potentiate TNFα signaling pathway members or genetic engineering molecules that knock-down/knock-out or otherwise disrupt the activity of TNFRSF members that inhibit TNFα signaling pathway members.

In particular embodiments, genetic engineering molecules can result in the expression of one or more of the proteins TWEAK (tumor necrosis factor-like weak inducer of apoptosis); TRAIL (Tumor necrosis factor-related apoptosis-inducing ligand); and LIGHT (homologous to lymphotoxin, exhibits inducible expression and competes with HSV glycoprotein D for binding to herpesvirus entry mediator, a receptor expressed on T lymphocytes).

In particular embodiments, immune cells genetically modified to express a CAR or similar molecule are also genetically modified to express one or more of TNFα signal potentiators. In particular embodiments, immune cells genetically modified to express a CAR or similar molecule are also genetically modified to knock-down, knock-out or otherwise disrupt one or more TNFRSF members that inhibit TNFα signaling pathway members.

In particular embodiments, the TNFα signal potentiator is a small molecule or protein selected from, for example, BV-6, CUDC-427, GDC-0152, LCL161, Rocaglamide, Sirolimus, Escin, Emricasan, Birinapant, ASTX660, AZD5582, KILLERTRAIL™ (Enzo Life Sciences, Farmingdale, NY), BI 891065, DEBIO 1143, APG-1387, HGS1029, and AEG35156.

BRIEF DESCRIPTION OF THE FIGURES

(FIG. 1A)=CD33-pos-$Cr^{51}$ labeled with CD33-neg cells, (FIG. 1B)=CD33-neg-$Cr^{51}$ labelled with CD33-pos cells, (FIG. 1C)=CD33-pos-$Cr^{51}$ labeled with CD33-pos cells, (FIG. 1D)=CD33-neg-$Cr^{51}$ labelled with CD33-neg cells. Cells are exposed to $CD33_{PROX}$ CAR-T cells for 4 hours or 24 hours. $Cr^{51}$ levels within the supernatant are then measured by scintillation counter and calculated as percent cytotoxicity relative to maximum cell lysis (from detergent) subtracted from spontaneous cell lysis (in culture media alone). Cells that are lysed by CAR-T cells are demarcated as skull and crossbones. Arrow represents $Cr^{51}$ release.

(FIG. 2A)-(FIG. 2D) Healthy Donor 04: (FIG. 2A) 4 hours; short spacer; (FIG. 2B) 24 hours; short spacer; (FIG. 2C) 4 hours; intermediate spacer; (FIG. 2D) 24 hours; intermediate spacer; (FIG. 2E)-(FIG. 2H) Healthy Donor 07: (FIG. 2E) 4 hours; short spacer; (FIG. 2F) 24 hours; short spacer; (FIG. 2G) 4 hours; intermediate spacer; (FIG. 2H) 24 hours; intermediate spacer.

(FIG. 3A) After 4 hours of culture, 1H7 $CD4^+$ CAR-T cells resulted in antigen-specific killing of CD33-pos ML1 targets (bars designated as ★ and ■) but not CD33-neg ML1 targets (bars designated ● and ♦). (FIG. 3B) In contrast, at 24 hours and only when cultured with CD33-pos ML1 targets, robust killing of chromium-labelled CD33-neg ML1 cells (bars designated as ●) were observed, indicating that antigen-negative bystander AML cell death was also promoted by $CD4^+$ CAR-T cell activation by antigen-positive target cells.

FIG. 6. Tumor necrosis factor receptor superfamily (TNFRSF) members that can be modulated to enhance antigen-negative cell death in antigen-targeted immunotherapies.

FIGS. 9A, 9B. SMAC/Diablo mimetics with purported capacity to enhance TNFα-mediated cell death and results achieved with same. (9A) SMAC/Diablo mimetics are a class of drugs that decrease the threshold to TNFα-mediated signaling and cell death. (9B) Antigen-negative killing can be enhanced by SMAC/Diablo mimetics. Fluorescently-labelled ML1 cells deficient in CD33 ($CD33_{neg}^{GFP}$) and non-fluorescent ML1 parental cells ($CD33_{pos}$, top) or ML1 CD33 KO cells ($CD33_{neg}$, bottom) were co-cultured with various SMAC/Diablo mimetics at the concentrations listed in FIG. 9A. 24 hours later ML1 cells were exposed to media or CD33-directed CAR-T cells. Cell death was then assessed by staining cells for annexin V and 7AAD. Total number of live cells was assessed as GFP-positive annexin V and 7AAD negative cells and quantitated by TrueCount bead counting. Percent antigen-negative cell death was calculated as (total cell death in media control well−total cell death in CAR-T well)/total cell death in media control well×100%. **$p<0.0001$, *$p<0.001$, ns not significant versus vehicle (DMSO) control by ordinary one-way ANOVA with post-hoc Dunnett test.

FIG. 10. Additional examples of small molecule TNFα signaling modulators that have been trialed in mice and humans and can be used within the teachings of the current disclosure.

FIG. 11. Exemplary sequences supporting the disclosure.

DETAILED DESCRIPTION

Figure 1A:
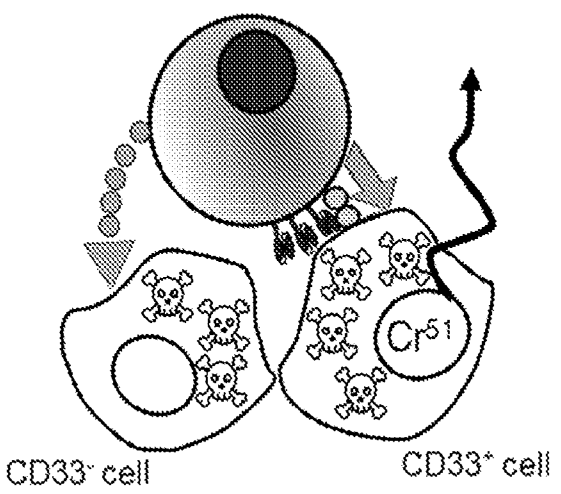
FIGS. 1A-1D. Schematic of antigen-negative killing assay. CD33-pos AML cell line, ML1, or ML1 cells deficient in CD33 from CRISPR-Cas9 targeting are labelled with chromium$^{51}$ ($Cr^{51}$) and cultured in one of the following four combinations.
Figure 1B:
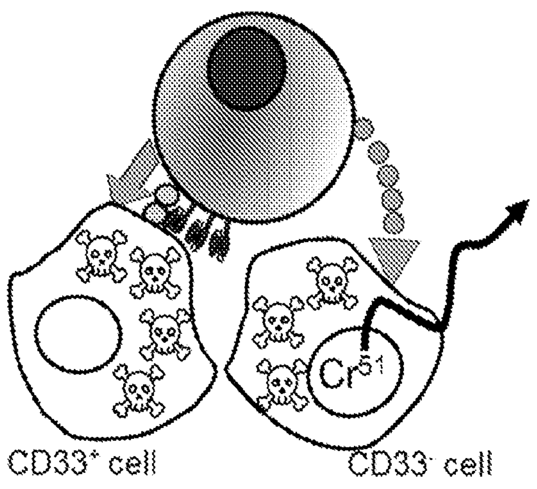
Figure 1C:
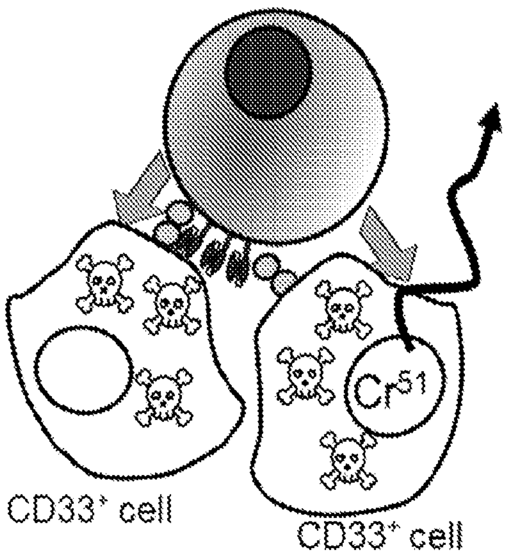
Figure 1D:
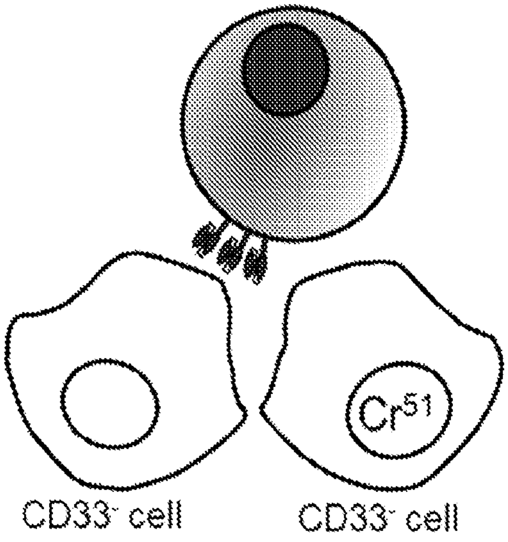
Figure 2A:
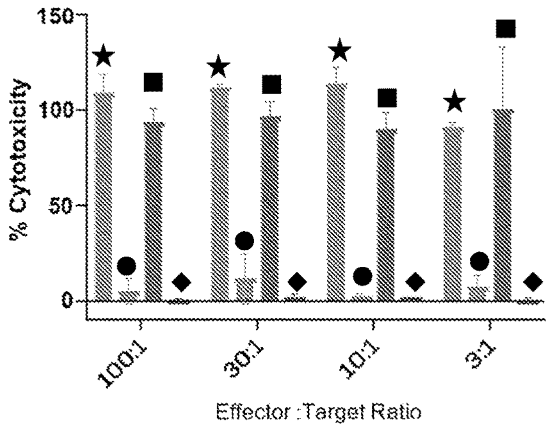
FIGS. 2A-2H. CD33-directed CD8+ CAR-T cells show robust antigen-negative bystander killing across different CAR lengths and different donors. Chromium$^{51}$-labelled CD33-positive (pos) AML cell line, ML1, or ML1 cells deficient in CD33 from CRISPR-Cas9 targeting were co-cultured with CD33-directed 1H7 CAR-T cells for 4 hours or 24 hours and cell supernatants collected and analyzed for released radiation by scintillation counter. Percent cytotoxicity calculated as scintillation minus background divided by maximum release (as elicited by detergent treatment) multiplied by 100%. After 4 hours of culture, 1H7 CAR-T cells resulted in antigen-specific killing of CD33-pos ML1 targets (bars designated as ★ and ■), but not CD33-negative (neg) ML1 targets (bars designated as ● and ♦). In contrast, at 24 hours and only when cultured with CD33-pos ML1 targets, robust killing of chromium-labelled CD33-neg ML1 cells (bars designated as ●) was observed, indicating that antigen-negative bystander AML cell death was promoted by CAR-T cell activation by antigen-positive target cells. This effect was observed in CAR constructs with a long or short spacer.
Figure 2B:
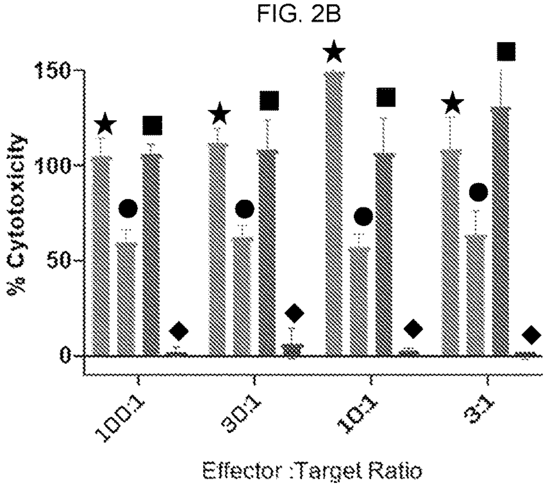
Figure 2C:
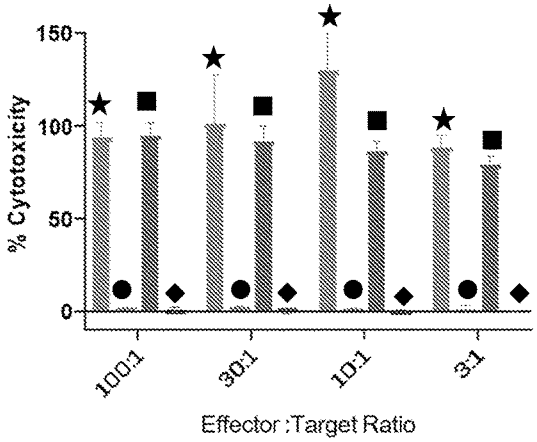
Figure 2D:
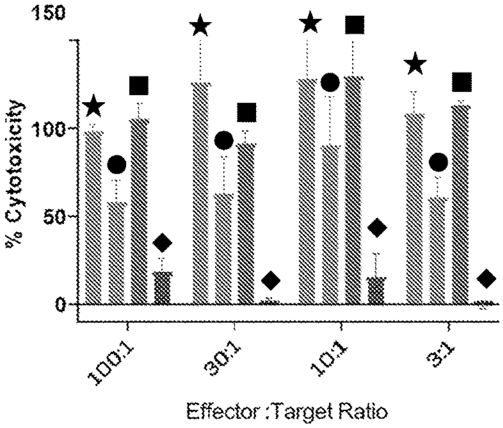
Figures 2E, 2F, 2G, 2H:
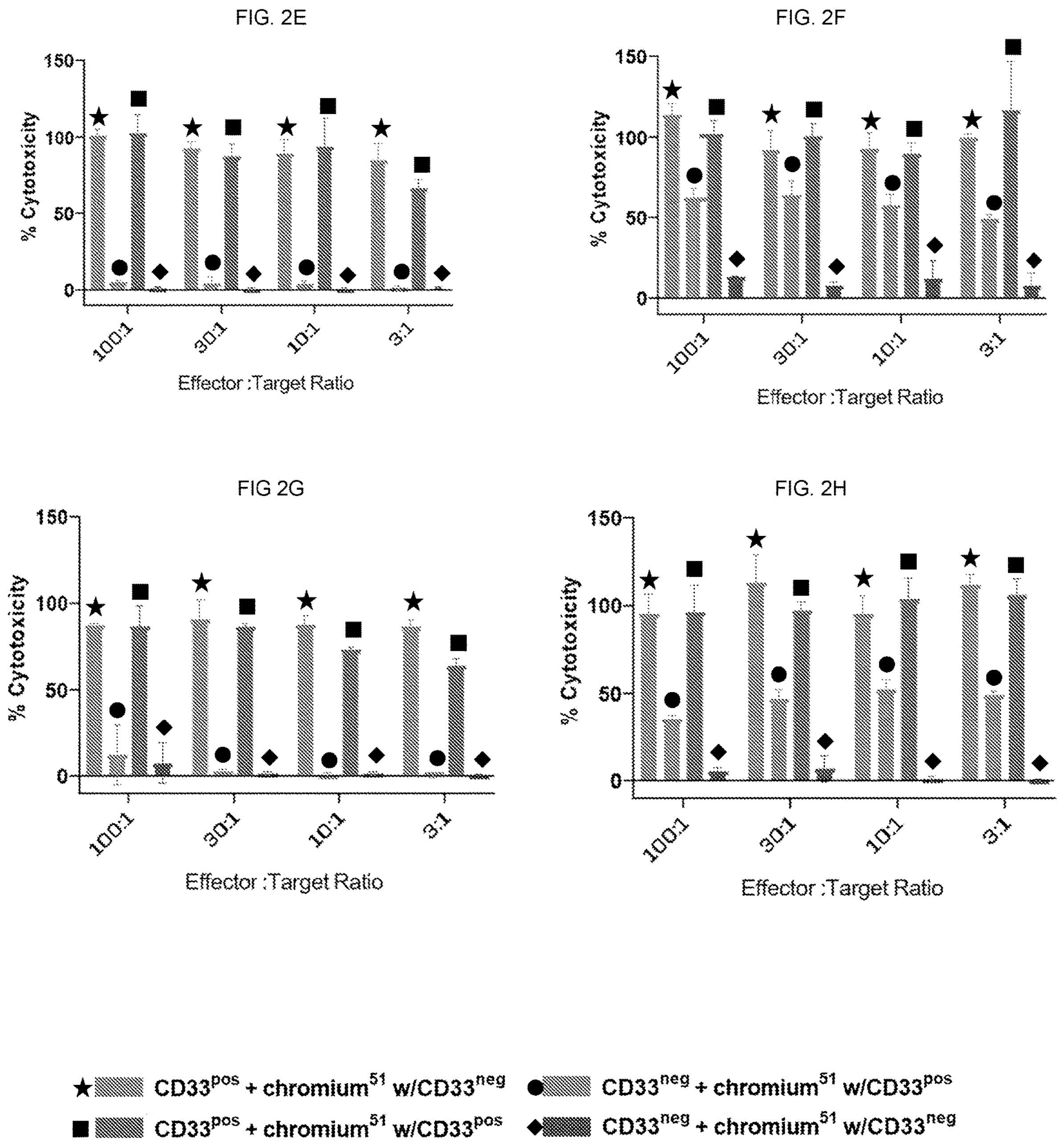
Figure 3A:
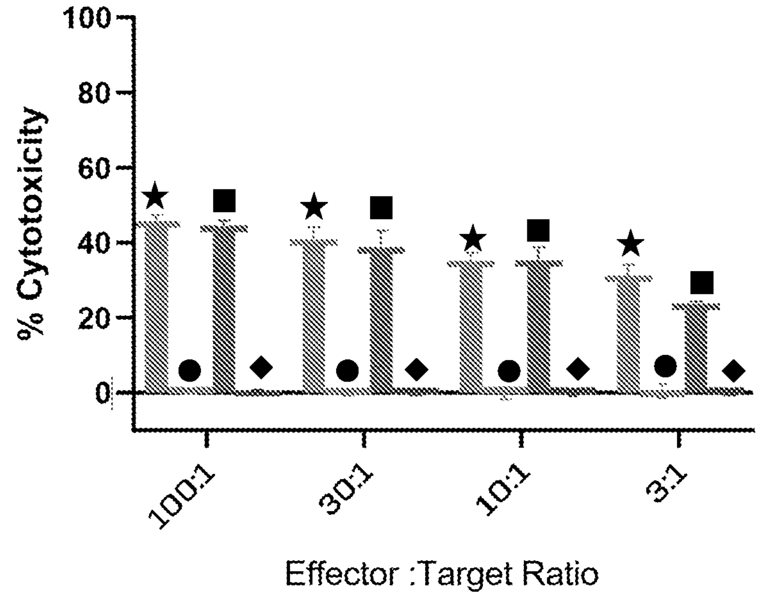
FIGS. 3A, 3B. CD33-directed $CD4^+$ CAR-T cells show robust antigen-negative bystander killing. Chromium$^{51}$-labelled CD33-pos AML cell line, ML1, or ML1 cells deficient in CD33 from CRISPR-Cas9 targeting were co-cultured with CD33-directed 1H7 $CD4^+$ CAR-T cells for 4 hours or 24 hours and cell supernatants collected and analyzed for released radiation by scintillation counter. Percent cytotoxicity calculated as scintillation minus background divided by maximum release (as elicited by detergent treatment) multiplied by 100%.
Figure 3B:
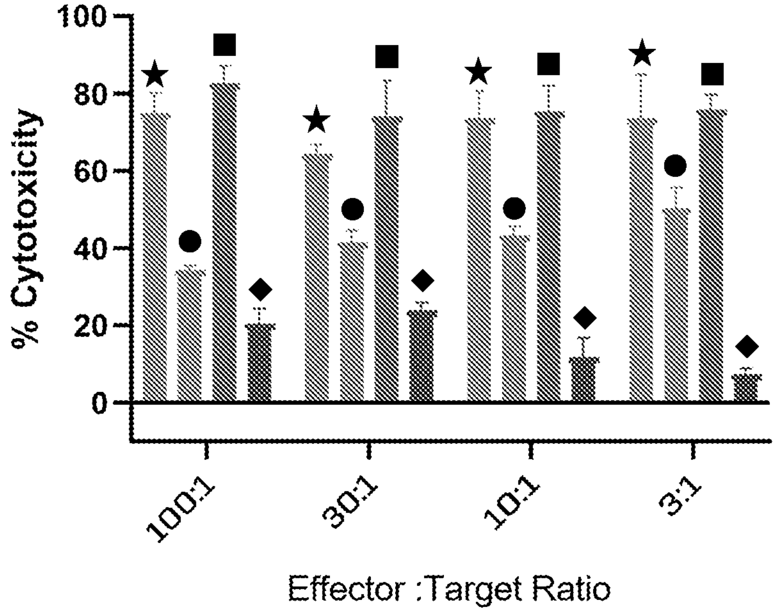
Figure 4:
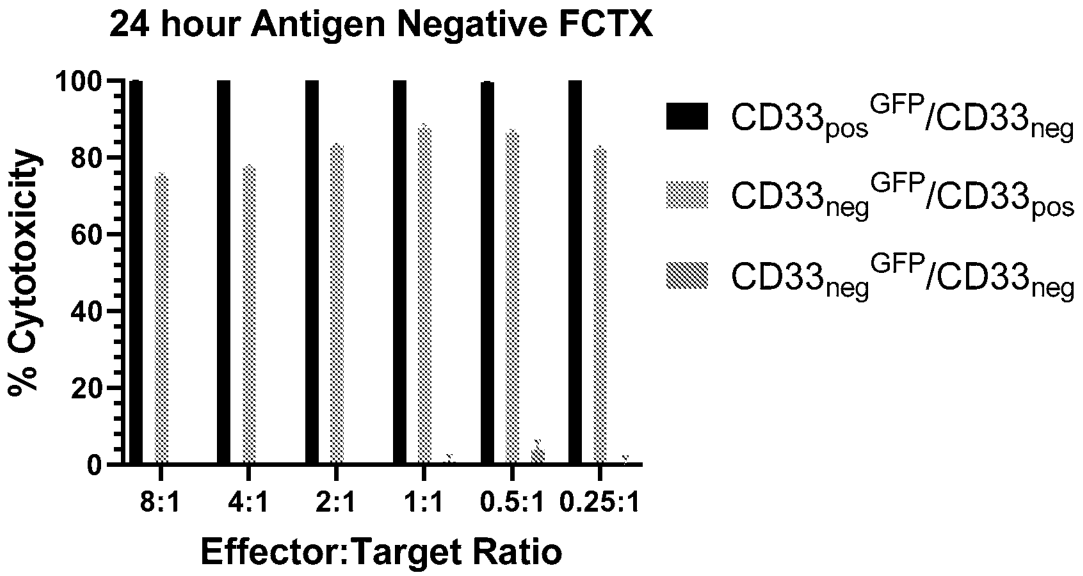
FIG. 4. Antigen-negative killing is also seen in an assay of flow cytotoxicity. 1H7 CAR-T cells directed against the membrane-proximal component of CD33 (C2-set) were expanded in IL-7 and IL-15 over ten days. CAR-T cells were then co-cultured for 24 hours in one of three conditions: 1) fluorescently-labelled ML1 cells that express endogenous levels of CD33 ($CD33_{pos}^{GFP}$) with non-fluorescent ML1 cells genetically deficient in CD33 by clustered regularly interspaced short palindromic repeats-Cas9 (CRISPR-Cas9) technology ($CD33_{neg}$); 2) $CD33_{neg}^{GFP}$ cells with non-GFP expressing $CD33_{pos}$ cells; 3) $CD33_{neg}^{GFP}$ cells with non-GFP expressing $CD33_{neg}$ cells. Cell death was then assessed by staining cells for annexin V and 7AAD. Total number of annexin V positive, annexin V and 7AAD positive or 7AAD positive cells was quantitated by TrueCount bead counting and percentage of cell death was measured relative to 100% cell death (ML1 cells microwaved at 1200 W for 15 seconds). This data shows that antigen-negative cell killing is not limited to chromium$^{51}$ release assays.
Figure 5A:
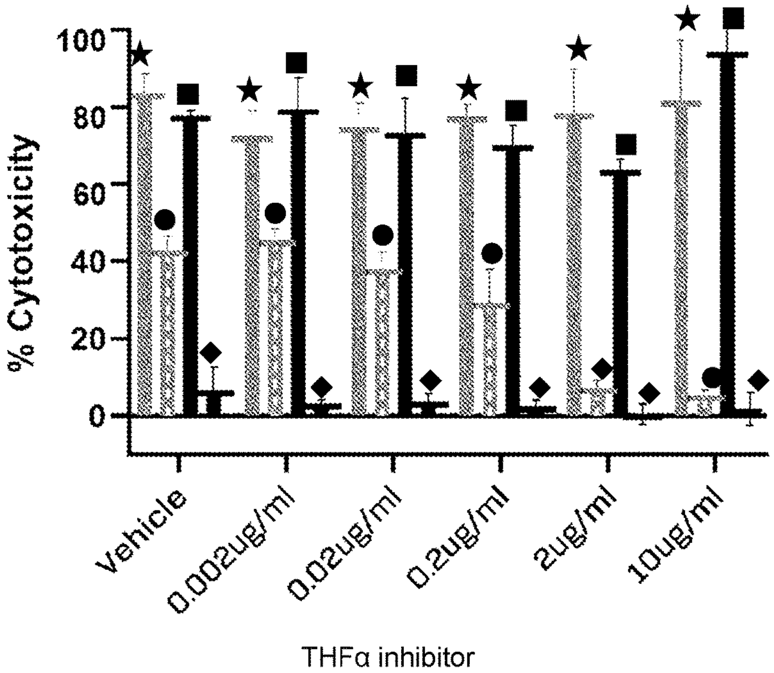
FIGS. 5A-5C. Antigen negative cell killing is dependent on TNFα and FasL. Chromium$^{51}$-labelled CD33-pos AML cell line, ML1, or ML1 cells deficient in CD33 from CRISPR-Cas9 targeting were co-cultured with CD33-directed 1H7 $CD8^+$ CAR-T cells for 24 hours with varying levels of inhibitors of TNFα (FIG. 5A), IFNγ (FIG. 5B) or FasL inhibitors (FIG. 5C) at a 10:1 effector to target ratio. Percent cytotoxicity calculated as scintillation minus background divided by maximum release (as elicited by detergent treatment) multiplied by 100%. TNFα inhibition resulted in almost no antigen-negative cell death.
Figure 5B:
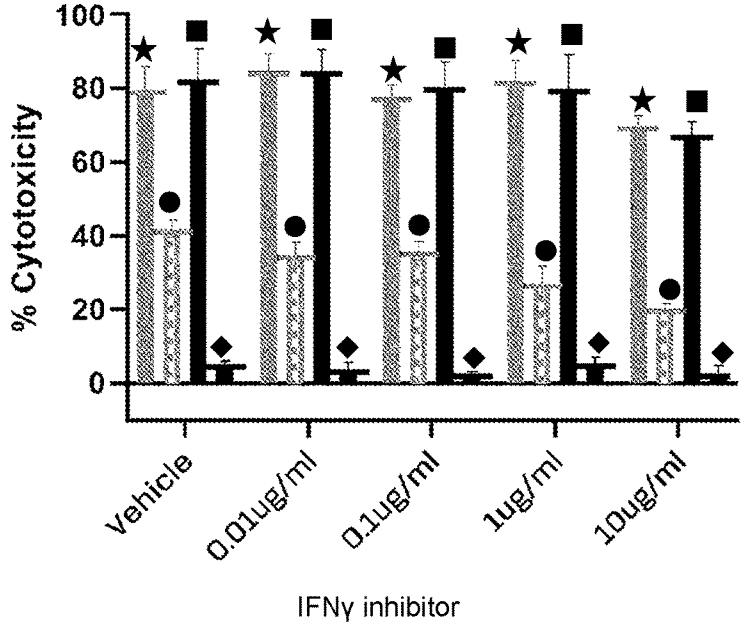
Figure 5C:
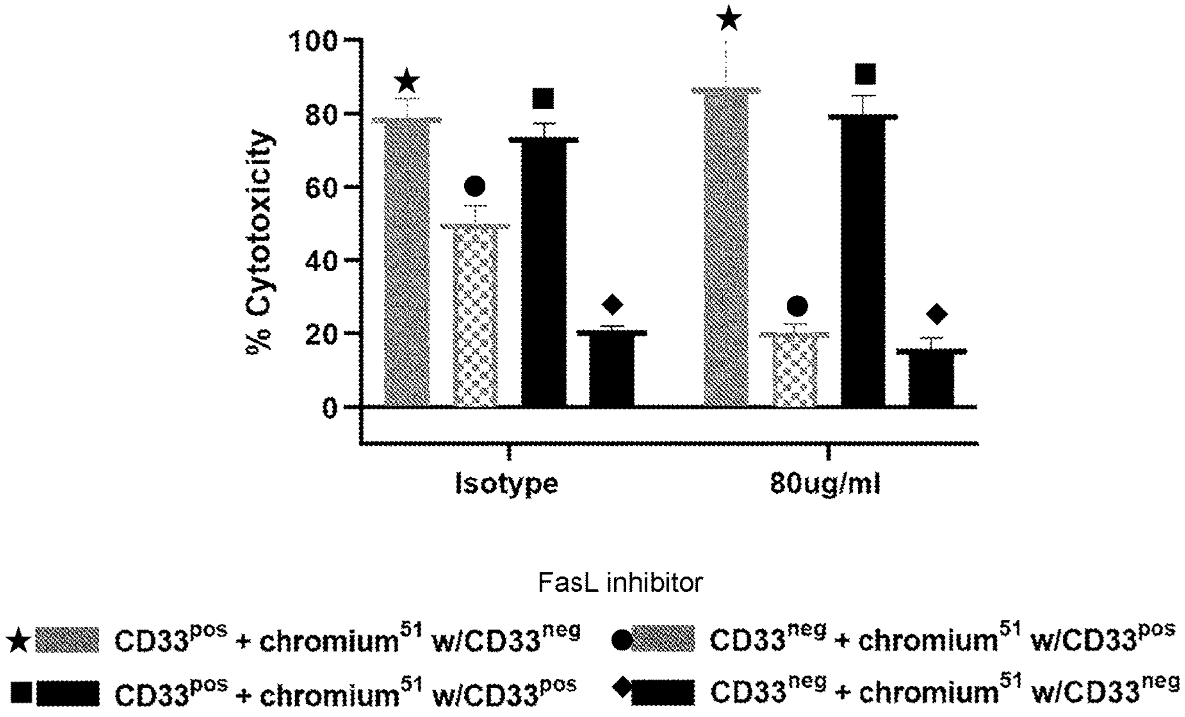
Figure 7:
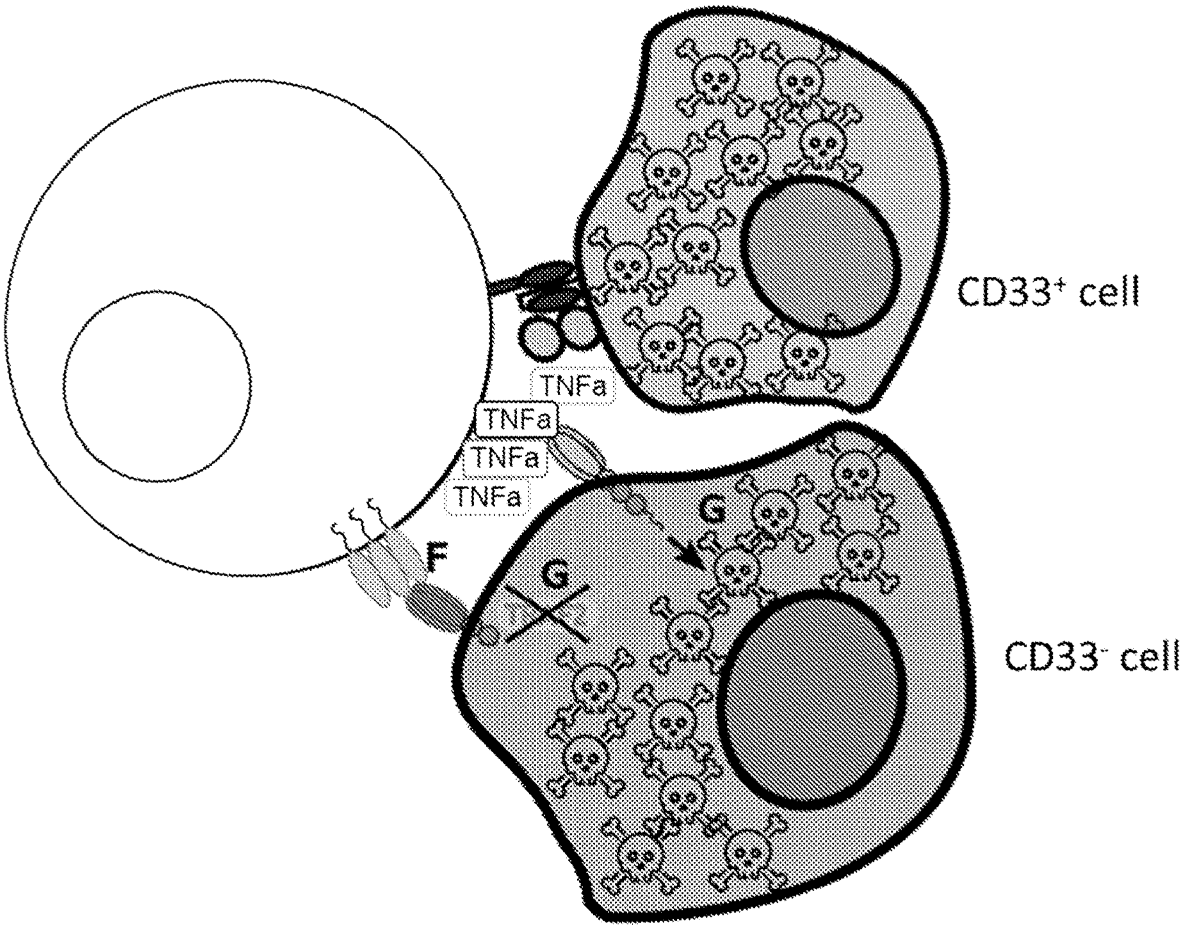
FIG. 7. Chimeric antigen receptor (CAR) induces death of antigen positive cells (A) and expression of tumor necrosis factor alpha (TNFα, A) which can signal to nearby antigen negative cells (B) through the TNF receptor super family (TNFRSF) thereby inducing "bystander killing" as demonstrated herein. However, this cell death is inhibited by proteins, over-expressed in cancer, that normally inhibit TNFα-induced cell death, such as TNF-receptor associated factor 2 (TRAF2). One disclosed augmentation of CAR-T cell therapy involves introducing a transgene in cis with the CAR gene that contains an upstream NFAT promoter. Signaling through the CAR (C) will result in transcription from the NFAT promoter (D) and subsequent expression (E) of a membrane bound form of TNF-related weak induced of apoptosis (mTWEAK), TNF-related apoptosis-inducing ligand (TRAIL), or homologous to lymphotoxin, exhibits inducible expression and competes with HSV glycoprotein D for binding to herpesvirus entry mediator, a receptor expressed on T lymphocytes (LIGHT). All three of these proteins are known to lower the threshold for TNFα-induced cell death by, for example, inducing degradation of inhibitors of TNFα-induced cell death (F-G).
Figure 8:
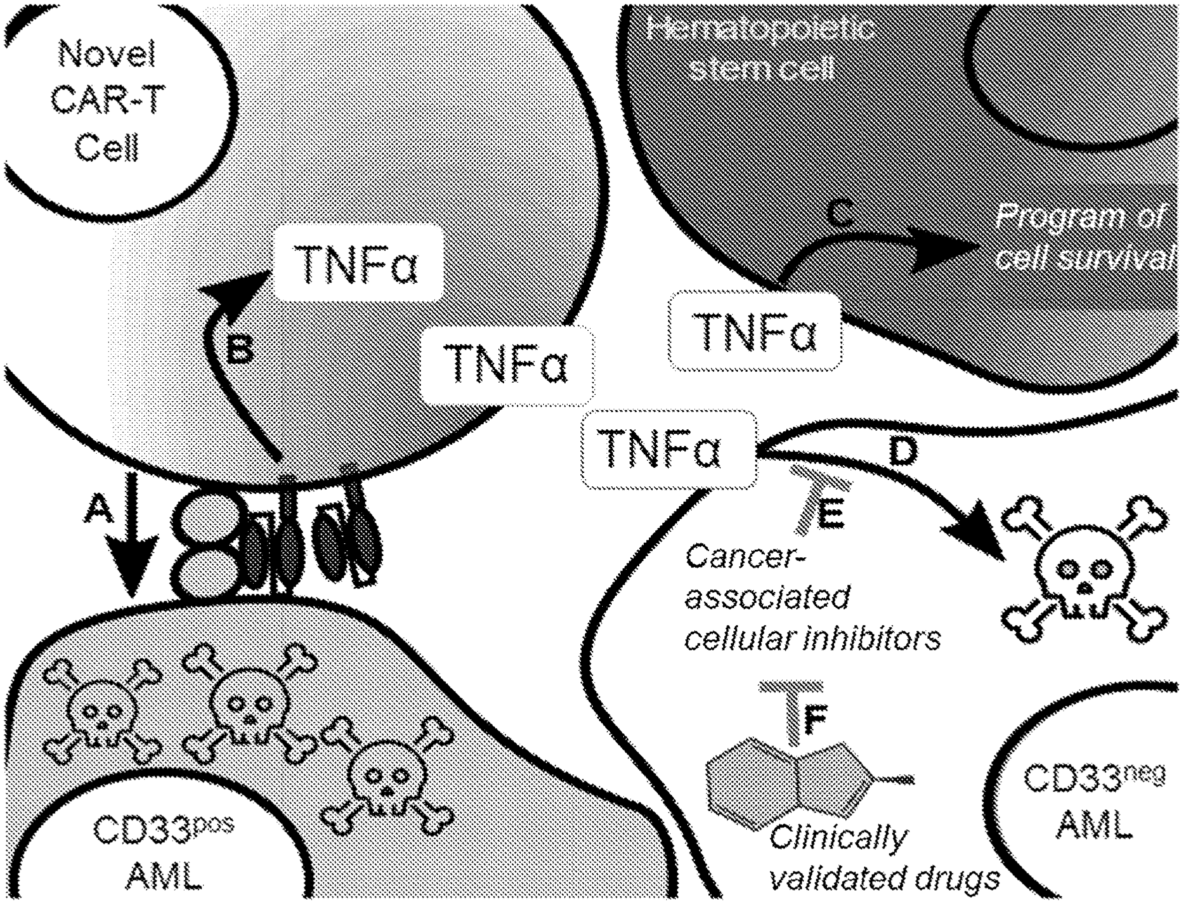
FIG. 8. Schematic of drug-augmented, TNFα-mediated antigen-negative killing whilst preserving normal hematopoiesis. CAR-T cells directed against the membrane proximal domain of CD33 deliver an efficient kill signal to CD33-pos AML cells (A) whilst precipitating the release of tumor necrosis factor α (TNFα, B). TNFα induces a state of quiescence and cell survival in hematopoietic stem cells (C). In cancer cells, however, TNFα provokes cell death (D) that is prevented by endogenous inhibitors of regulated cell death over-expressed in AML (E). These cellular inhibitors can, in turn, be inhibited by pharmacologic inhibitors (F, and e.g., FIGS. 9A and 10) that have been validated in clinical trials or are in clinical use.

According to the World Health Organization, cancer is the second leading cause of death globally, and was responsible for an estimated 9.6 million deaths in 2018. For many years, the chosen treatments for cancer have been surgery, chemotherapy, and radiation therapy. In recent years, more targeted therapies have emerged to specifically target cancer cells by identifying and exploiting specific molecular changes seen primarily in those cells. For example, significant progress has been made in genetically engineering T cells of the immune system to target and kill unwanted cell types, such as cancer cells. Many of these T cells have been genetically engineered to express chimeric antigen receptor (CAR) constructs. CARs are proteins including several distinct subcomponents that allow the genetically modified T cells to recognize and kill cancer cells. The subcomponents include at least an extracellular component and an intracellular component.

The extracellular component includes a binding domain that specifically binds an antigen that is preferentially present on the surface of unwanted cells. When the binding domain binds such antigens, the intracellular component directs the T cell to destroy the bound cancer cell. The binding domain is typically a single-chain variable fragment (scFv) derived from a monoclonal antibody (mAb), but it can be based on other formats which include, for example, an antibody-like antigen binding site or a T cell receptor (TCR).

The intracellular components provide activation signals based on the inclusion of an effector domain. First generation CARs utilized the cytoplasmic region of CD3ζ as an effector domain. Second generation CARs utilized CD3ζ in combination with cluster of differentiation 28 (CD28) or 4-1BB (CD137), while third generation CARs have utilized CD3ζ in combination with CD28 and 4-1BB within intracellular effector domains.

CAR generally also include one or more linker sequences that are used for a variety of purposes within the molecule. For example, a transmembrane domain can be used to link the extracellular component of the CAR to the intracellular component. A flexible linker sequence often referred to as a spacer region that is membrane-proximal to the binding domain can be used to create additional distance between a binding domain and the cellular membrane. This can be beneficial to reduce steric hindrance to binding based on proximity to the membrane. A common spacer region used for this purpose is the IgG4 linker. More compact spacers or longer spacers can be used, depending on the targeted cell antigen. Other potential CAR subcomponents are described in more detail elsewhere herein.

Clinical trials with CAR-expressing T cells have shown positive responses in patients with refractory large B-cell lymphoma when conventional treatments had failed (Neelapu, et al 2017 N Engl J Med 377:2531-2544). However, while CAR constructs can successfully genetically engineer T cells to result in cancer cell destruction, they have failed to provide prolonged anti-cancer activity in vivo for some indications. For example, antigen-negative relapse is a common cause of treatment failure following antigen-directed immunotherapy, such as treatment with CAR-expressing T cells (commonly referred to as CAR-T cells). The current disclosure provides that immune cells modified to express a CAR or similar molecule against a particular cellular antigen can also induce the killing of cancer cells that do no express the antigen after initial priming by the presence of the targeted cellular antigen. For example, CAR-T cells directed against the myeloid malignancy associated antigen, CD33, can induce killing of CD33-negative cells after initial priming by a CD33-expressing target (i.e. in the presence of CD33-positive cells). This allows CAR-T cells to first be activated by the target antigen and then to kill other cells in the tumor microenvironment that do not express the target antigen, providing an opportunity to increase depth of remission and reduce the risk of antigen-negative escape.

It has been determined that this observed "bystander killing" is dependent on TNFα pathway signals as evidenced by inhibition of antigen-negative cell death when TNFα or FasL are inhibited. Thus, the current disclosure provides administration of an immunotherapy, such as a CAR-expressing immune cell in combination with a compound that potentiates or preserves the in vivo cell killing actions of TNFα. As shown herein, these combination therapies allow the killing of antigen-positive cells that are bound by a CAR or similar molecule. Potentiating or preserving the actions of TNFα also allows effective killing of antigen-negative cancer cells in the area of the targeted antigen-positive cells, thus reducing the survivability of escape variants among other benefits.

A compound that potentiates or preserves the in vivo cell killing actions of TNFα is referred to herein as a TNFα signal potentiator. In particular embodiments, TNFα signal potentiators include molecules that activate, enhance, or support tumor necrosis factor receptor superfamily (TNFRSF) members that activate, enhance, or support TNFα signaling pathway members. In particular embodiments, TNFα signal potentiators include molecules that activate, enhance, or support TNFα signaling pathway members. Activate refers to changing a molecule from an inactive to an active state. Enhance refers to bringing a molecule from an active state to a more active state. Support means maintaining the activation state of a molecule in conditions where its activity would otherwise be down-regulated.

In particular embodiments, TNFα signal potentiators include molecules that de-activate, suppress, or disrupt TNFSRF members that de-activate, suppress, or disrupt TNFα signaling pathway members. De-activate refers to changing a molecule from an active to an inactive state. Suppress refers to bringing a molecule from an active state to a less active state. Disrupt means reducing the activation state of a molecule in conditions where its activity would otherwise be maintained and/or preventing the expression of a functioning form of the molecule.

In particular embodiments, TNFα signal potentiators can include genetic engineering molecules that knock-in TNFRSF members that potentiate TNFα signaling pathway members or knock-down/knock-out or otherwise disrupt the expression of TNFRSF members that inhibit TNFα signaling pathway members.

In particular embodiments, protein-engineering modifications, such as increased surface expression of TNF-associated death signals, can be made in CAR-T cells and other antigen-directed therapies to enhance bystander killing. Furthermore, these augmenting mechanisms tend to occur only within malignancies thus sparing normal tissue and reducing toxicities. In particular embodiments, TNFα signal potentiators include one or more of the proteins TWEAK (tumor necrosis factor-like weak inducer of apoptosis); TRAIL (Tumor necrosis factor-related apoptosis-inducing ligand); and LIGHT (homologous to lymphotoxin, exhibits inducible expression and competes with HSV glycoprotein D for binding to herpesvirus entry mediator, a receptor expressed on T lymphocytes). These proteins lower the threshold of TNFα-induced cell death. Without being limited by theory, these proteins lower the threshold of TNFα-induced cell death by inducing degradation of molecules that inhibit TNFα-induced cell death. In particular embodiments, immune cells genetically modified to express a CAR or similar molecule are also genetically modified to express or include one or more TNFα signal potentiators.

In particular embodiments, immune cells genetically modified to express a CAR or similar molecule are also genetically modified to knock-down, knock-out or otherwise inactivate one or more TNFRSF members that inhibit TNFα signaling pathway members.

FIG. 6 provides a table of TNFRSF members and whether the particular family member should be potentiated or inhibited for a molecule to be classified as a TNFα signal potentiator within the context of the current disclosure. As shown in FIG. 6, TNFα signal potentiators activate, enhance, and/or support the actions of TNFRSF members 1A, 1B, 3, 6, 8, 10A, 10B, 12A, 19 and/or 21 and/or deactivate, suppress, or disrupt the actions of TNFRSF members 6B, 10C, and/or 10D.

Further, several, clinically available small molecules can augment antigen-negative bystander cell killing by blocking inhibitors of TNFα-mediated cell death. In particular embodiments, these small molecules include one or more of BV-6, CUDC-427, GDC-0152, LCL161, Rocaglamide, Sirolimus, Emricasan, Birinapant, ASTX660, AZD5582, KILLERTRAIL™ BI 891065, DEBIO 1143, APG-1387, HGS1029, Escin, and AEG35156. In particular embodiments, the small molecule TNFα signal potentiator is a cIAP antagonist. Small molecule TNFα signal potentiators can also be SMAC-mimetics. Second mitochondria-derived activator of caspases (SMAC) are mitochondrial proteins (also referred to as DIABLO) which bind to cIAPs. This binding results in freeing caspases to activate apoptosis and results in a depletion of cIAPs. SMAC-mimetics mimic the action of SMAC on cIAPs.

The following aspects and options related to the current disclosure are now described in additional detail as follows: (I) Immune Cells; (II) Cell Sample Collection and Cell Enrichment; (III) Genetically Modifying Cell Populations to Express Chimeric Antigen Receptors (CAR) and Optionally TNFα Signal Potentiator Proteins; (III-A) Genetic Engineering Techniques; (III-B) CAR Subcomponents; (III-B-i) Binding Domains & Targeted Cellular Antigens; (III-B-ii) Spacer Regions (III-B-iii) Transmembrane Domains; (III-B-iv) Intracellular Effector Domains; (III-B-v) Linkers; (III-B-vi) Control Features Including Tag Cassettes, Transduction Markers, and/or Suicide Switches; (III-C) TNFα Signal Potentiator Proteins; (IV) Cell Activating Culture Conditions; (V) Ex Vivo Manufactured Cell Formulations; (VI) TNFα Signal Potentiators—Small Molecules and Proteins; (VII) Nanoparticle Formulations; (VIII) Methods of Use; (IX) Kits; (X) Exemplary Embodiments; and (XI) Closing Paragraphs. These headings are provided for organizational purposes only and do not limit the scope or interpretation of the disclosure.

(I) Immune Cells. The present disclosure describes immune cells genetically modified to express CAR and immune cells genetically modified to express or include a TNFα signal potentiator. In particular embodiments, the immune cells genetically modified to express a CAR are the same as the immune cells genetically modified to express or include a TNFα signal potentiator.

Genetically modified cells can include T-cells, B cells, natural killer (NK) cells, monocytes/macrophages, lymphocytes, hematopoietic stem cells (HSCs), hematopoietic progenitor cells (HPC), and/or a mixture of HSC and HPC (i.e., HSPC). In particular embodiments, genetically modified cells include T-cells.

Several different subsets of T-cells have been discovered, each with a distinct function. For example, a majority of T-cells have a T-cell receptor (TCR) existing as a complex of several proteins. The actual T-cell receptor is composed of two separate peptide chains, which are produced from the independent T-cell receptor alpha and beta (TCRα and TCRβ) genes and are called α- and β-TCR chains.

γδ T-cells represent a small subset of T-cells that possess a distinct T-cell receptor (TCR) on their surface. In γδ T-cells, the TCR is made up of one γ-chain and one δ-chain. This group of T-cells is much less common (2% of total T-cells) than the as T-cells.

CD3 is expressed on all mature T cells. Activated T-cells express 4-1BB (CD137), CD69, and CD25. CD5 and transferrin receptor are also expressed on T-cells.

T-cells can further be classified into helper cells (CD4+ T-cells) and cytotoxic T-cells (CTLs, CD8+ T-cells), which include cytolytic T-cells. T helper cells assist other white blood cells in immunologic processes, including maturation of B cells into plasma cells and activation of cytotoxic T-cells and macrophages, among other functions. These cells are also known as CD4+ T-cells because they express the CD4 protein on their surface. Helper T-cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T-cells destroy virally infected cells and tumor cells and are also implicated in transplant rejection. These cells are also known as CD8+ T-cells because they express the CD8 glycoprotein on their surface. These cells recognize their targets by binding to antigen associated with MHC class I, which is present on the surface of nearly every cell of the body.

"Central memory" T-cells (or "TCM") as used herein refers to an antigen experienced CTL that expresses CD62L or CCR7 and CD45RO on the surface thereof and does not express or has decreased expression of CD45RA as compared to naive cells. In particular embodiments, central memory cells are positive for expression of CD62L, CCR7, CD25, CD127, CD45RO, and CD95, and have decreased expression of CD45RA as compared to naive cells.

"Effector memory" T-cell (or "TEM") as used herein refers to an antigen experienced T-cell that does not express or has decreased expression of CD62L on the surface thereof as compared to central memory cells and does not express or has decreased expression of CD45RA as compared to a naive cell. In particular embodiments, effector memory cells are negative for expression of CD62L and CCR7, compared to naive cells or central memory cells, and have variable expression of CD28 and CD45RA. Effector T-cells are positive for granzyme B and perforin as compared to memory or naive T-cells.

"Naive" T-cells as used herein refers to a non-antigen experienced T cell that expresses CD62L and CD45RA and does not express CD45RO as compared to central or effector memory cells. In particular embodiments, naive CD8+ T lymphocytes are characterized by the expression of phenotypic markers of naive T-cells including CD62L, CCR7, CD28, CD127, and CD45RA.

Natural killer cells (also known as NK cells, K cells, and killer cells) are activated in response to interferons or macrophage-derived cytokines. They serve to contain viral infections while the adaptive immune response is generating antigen-specific cytotoxic T cells that can clear the infection. NK cells express CD8, CD16 and CD56 but do not express CD3.

Macrophages (and their precursors, monocytes) reside in every tissue of the body (in certain instances as microglia, Kupffer cells and osteoclasts) where they engulf apoptotic cells, pathogens and other non-self-components. Monocytes/macrophages express CD11b, F4/80; CD68; CD11c; IL-4Rα; and/or CD163.

Immature dendritic cells (i.e., pre-activation) engulf antigens and other non-self-components in the periphery and subsequently, in activated form, migrate to T-cell areas of lymphoid tissues where they provide antigen presentation to T cells. Dendritic cells express CD1a, CD1b, CD1c, CD1d, CD21, CD35, CD39, CD40, CD86, CD101, CD148, CD209, and DEC-205.

Hematopoietic Stem/Progenitor Cells or HSPC refer to a combination of hematopoietic stem cells and hematopoietic progenitor cells.

Hematopoietic stem cells refer to undifferentiated hematopoietic cells that are capable of self-renewal either in vivo, essentially unlimited propagation in vitro, and capable of differentiation to all other hematopoietic cell types.

A hematopoietic progenitor cell is a cell derived from hematopoietic stem cells or fetal tissue that is capable of further differentiation into mature cells types. In certain embodiments, hematopoietic progenitor cells are $CD24^{lo}$ $Lin^-$ $CD117^+$ hematopoietic progenitor cells. HPC can differentiate into (i) myeloid progenitor cells which ultimately give rise to monocytes and macrophages, neutrophils, basophils, eosinophils, erythrocytes, megakaryocytes/platelets, or dendritic cells; or (ii) lymphoid progenitor cells which ultimately give rise to T-cells, B-cells, and NK-cells.

HSPC can be positive for a specific marker expressed in increased levels on HSPC relative to other types of hematopoietic cells. For example, such markers include CD34, CD43, CD45RO, CD45RA, CD59, CD90, CD109, CD117, CD133, CD166, HLA DR, or a combination thereof. Also, the HSPC can be negative for an expressed marker relative to other types of hematopoietic cells. For example, such markers include Lin, CD38, or a combination thereof. Preferably, the HSPC are $CD34^+$ cells.

A statement that a cell or population of cells is "positive" for or expressing a particular marker refers to the detectable presence on or in the cell of the particular marker. When referring to a surface marker, the term can refer to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

A statement that a cell or population of cells is "negative" for a particular marker or lacks expression of a marker refers to the absence of substantial detectable presence on or in the cell of a particular marker. When referring to a surface marker, the term can refer to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

Cells to be genetically modified according to the teachings of the current disclosure can be patient-derived cells (autologous) or, when appropriate can be allogeneic.

(II) Cell Sample Collection and Cell Enrichment. Methods of sample collection and enrichment are known by those skilled in the art. In some embodiments, cells are derived from cell lines. The cells in some embodiments are obtained from a xenogeneic source, for example, from mouse, rat, non-human primate, or pig. In particular embodiments, cells are derived from humans.

In some embodiments, T cells are derived or isolated from samples such as whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. In particular embodiments, cells from the circulating blood of a subject are obtained, e.g., by apheresis or leukapheresis. The samples, in particular embodiments, contain lymphocytes, including T cells, monocytes, granulocytes, B cells, other nucleated white blood cells, HSC, HPC, HSPC, red blood cells, and/or platelets, and in some aspects contains cells other than red blood cells and platelets and further processing is necessary.

In some embodiments, blood cells collected from a subject are washed, e.g., to remove the plasma fraction and to place the cells in an appropriate buffer or media for subsequent processing steps. In particular embodiments, the cells are washed with phosphate buffered saline (PBS). In some embodiments, the wash solution lacks calcium and/or magnesium and/or many or all divalent cations. Washing can be accomplished using a semi-automated "flow-through" centrifuge (for example, the Cobe 2991 cell processor, Baxter) according to the manufacturer's instructions. Tangential flow filtration (TFF) can also be performed. In particular embodiments, cells can re-suspended in a variety of biocompatible buffers after washing, such as, Ca++/Mg++ free PBS.

The isolation can include one or more of various cell preparation and separation steps, including separation based on one or more properties, such as size, density, sensitivity or resistance to particular reagents, and/or affinity, e.g., immunoaffinity, to antibodies or other binding partners. In particular embodiments, the isolation is carried out using the same apparatus or equipment sequentially in a single process stream and/or simultaneously. In particular embodiments, the isolation, culture, and/or engineering of the different populations is carried out from the same starting composition or material, such as from the same sample.

In particular embodiments, a sample can be enriched for T cells by using density-based cell separation methods and related methods. For example, white blood cells can be separated from other cell types in the peripheral blood by lysing red blood cells and centrifuging the sample through a Percoll or Ficoll gradient.

In particular embodiments, a bulk T cell population can be used that has not been enriched for a particular T cell type. In particular embodiments, a selected T cell type can be enriched for and/or isolated based on cell-marker based positive and/or negative selection. In positive selection, cells having bound cellular markers are retained for further use. In negative selection, cells not bound by a capture agent, such as an antibody to a cellular marker are retained for further use. In some examples, both fractions can be retained for a further use.

The separation need not result in 100% enrichment or removal of a particular cell population or cells expressing a particular marker. For example, positive selection of or enrichment for cells of a particular type refers to increasing the number or percentage of such cells but need not result in a complete absence of cells not expressing the marker. Likewise, negative selection, removal, or depletion of cells of a particular type refers to decreasing the number or percentage of such cells but need not result in a complete removal of all such cells.

In some examples, multiple rounds of separation steps are carried out, where the positively or negatively selected fraction from one step is subjected to another separation step, such as a subsequent positive or negative selection.

In some embodiments, an antibody or binding domain for a cellular marker is bound to a solid support or matrix, such as a magnetic bead or paramagnetic bead, to allow for separation of cells for positive and/or negative selection. For example, in some embodiments, the cells and cell populations are separated or isolated using immunomagnetic (or affinity magnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, NJ); see also U.S. Pat. Nos. 4,452,773; 4,795,698; 5,200,084; and EP 452342.

In some embodiments, affinity-based selection is via magnetic-activated cell sorting (MACS) (Miltenyi Biotec, Auburn, CA). MACS systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376). In both cases, cells can be labeled with multiple markers, allowing for the isolation of well-defined cell subsets at high purity.

Cell-markers for different T cell subpopulations are described above. In particular embodiments, specific subpopulations of T cells, such as cells positive or expressing high levels of one or more surface markers, e.g., CCR7, CD45RO, CD8, CD27, CD28, CD62L, CD127, CD4, and/or CD45RA T cells, are isolated by positive or negative selection techniques.

CD3+, CD28+ T cells can be positively selected for and expanded using anti-CD3/anti-CD28 conjugated magnetic beads (e.g., DYNABEADS® M-450 CD3/CD28 T Cell Expander).

In particular embodiments, a CD8+ or CD4+ selection step is used to separate CD4+ helper and CD8+ cytotoxic T cells. Such CD8+ and CD4+ populations can be further sorted into sub-populations by positive or negative selection for markers expressed or expressed to a relatively higher degree on one or more naive, memory, and/or effector T cell subpopulations. In particular embodiments, cells are sorted to obtain a 1:1 CD8+ to CD4+ ratio.

In some embodiments, enrichment for central memory T (TCM) cells is carried out. In particular embodiments, memory T cells are present in both CD62L subsets of CD8+ peripheral blood lymphocytes. PBMC can be enriched for or depleted of CD62L, CD8 and/or CD62L+CD8+ fractions, such as by using anti-CD8 and anti-CD62L antibodies.

In some embodiments, the enrichment for central memory T (TCM) cells is based on positive or high surface expression of CCR7, CD45RO, CD27, CD62L, CD28, CD3, and/or CD127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CCR7, CD45RO, and/or CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or RORI, and positive selection based on a marker characteristic of central memory T cells, such as CCR7, CD45RO, and/or CD62L, where the positive and negative selections are carried out in either order.

In particular embodiments, cell enrichment results in a bulk CD8+ FACs-sorted cell population.

Other cell types can be enriched based on known marker profiles and techniques. For example, CD34+ HSC, HSP, and HSPC can be enriched using anti-CD34 antibodies directly or indirectly conjugated to magnetic particles in connection with a magnetic cell separator, for example, the CliniMACS® Cell Separation System (Miltenyi Biotec, Bergisch Gladbach, Germany).

(III) Genetically Modifying Cell Populations to Express Chimeric Antigen Receptors (CAR) and/or a TNFα Signal Potentiator. Cell populations are genetically modified to express chimeric antigen receptors (CAR) and/or a TNFα signal potentiator.

(III-A) Genetic Engineering Techniques. Desired genes encoding CAR and/or a TNFα signal potentiator disclosed herein can be introduced into cells by any method known in the art, including transfection, electroporation, microinjection, lipofection, calcium phosphate mediated transfection, infection with a viral or bacteriophage vector including the gene sequences, cell fusion, chromosome-mediated gene transfer, microcell-mediated gene transfer, spheroplast fusion, in vivo nanoparticle-mediated delivery, etc. Numerous techniques are known in the art for the introduction of foreign genes into cells (see e.g., Loeffler and Behr, 1993, *Meth. Enzymol.* 217:599-618; Cohen, et al., 1993, *Meth. Enzymol.* 217:618-644; Cline, 1985, *Pharmac. Ther.* 29:69-92) and may be used, provided that the necessary developmental and physiological functions of the recipient cells are not unduly disrupted. The technique can provide for the stable transfer of the gene to the cell, so that the gene is expressible by the cell and, in certain instances, preferably heritable and expressible by its cell progeny.

The term "gene" refers to a nucleic acid sequence (used interchangeably with polynucleotide or nucleotide sequence) that encodes a CAR and/or a TNFα signal potentiator as described herein. This definition includes various sequence polymorphisms, mutations, and/or sequence variants wherein such alterations do not substantially affect the function of the encoded CAR and/or TNFα signal potentiator. The term "gene" may include not only coding sequences but also regulatory regions such as promoters, enhancers, and termination regions. The term further can include all introns and other DNA sequences spliced from an mRNA transcript, along with variants resulting from alternative splice sites. Gene sequences encoding the molecule can be DNA or RNA that directs the expression of the chimeric molecule. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific cell type. Portions of complete gene sequences are referenced throughout the disclosure as is understood by one of ordinary skill in the art.

Gene sequences encoding CAR and/or a TNFα signal potentiator are provided herein and can also be readily prepared by synthetic or recombinant methods from the relevant amino acid sequences and other description provided herein. In embodiments, the gene sequence encoding any of these sequences can also have one or more restriction enzyme sites at the 5' and/or 3' ends of the coding sequence in order to provide for easy excision and replacement of the gene sequence encoding the sequence with another gene sequence encoding a different sequence. In embodiments, the gene sequence encoding the sequences can be codon optimized for expression in mammalian cells.

"Encoding" refers to the property of specific sequences of nucleotides in a gene, such as a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system. A "gene sequence encoding a protein" includes all nucleotide sequences that are degenerate versions of each other and that code for the same amino acid sequence or amino acid sequences of substantially similar form and function.

Polynucleotide gene sequences encoding more than one portion of an expressed CAR and/or TNFα signal potentiator can be operably linked to each other and relevant regulatory sequences. For example, there can be a functional linkage between a regulatory sequence and an exogenous nucleic acid sequence resulting in expression of the latter. For another example, a first nucleic acid sequence can be operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary or helpful, join coding regions, into the same reading frame.

In particular embodiments, the promoter is an NFAT promoter. The NFAT promoter drives expression of operably linked coding sequences in a Ca2+-dependent manner. In particular embodiments, the NFAT promoter includes any number of binding motifs, for example, one, at least two, at least three, at least four, at least five, at least six, at least seven, at least eight, at least nine, at least ten, at least eleven, or up to twelve binding motifs. In particular embodiments, the NFAT promoter includes four to eight NFAT binding motifs.

In any of the embodiments described herein, a polynucleotide can include a polynucleotide that encodes a self-cleaving polypeptide, wherein the polynucleotide encoding the self-cleaving polypeptide is located between the polynucleotide encoding the CAR construct and a polynucleotide encoding a TNFα signal potentiator and/or a transduction marker (e.g., tEGFR). Exemplary self-cleaving polypeptides include 2A peptide from porcine teschovirus-1 (P2A), Thosea asigna virus (T2A), equine rhinitis A virus (E2A), foot-and-mouth disease virus (F2A), or variants thereof (see FIG. 11). Further exemplary nucleic acid and amino acid sequences of 2A peptides are set forth in, for example, Kim et al. (*PLOS One* 6:e18556 (2011).

A "vector" is a nucleic acid molecule that is capable of transporting another nucleic acid. Vectors may be, e.g., plasmids, cosmids, viruses, or phage. An "expression vector" is a vector that is capable of directing the expression of a protein encoded by one or more genes carried by the vector when it is present in the appropriate environment.

"Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

"Retroviruses" are viruses having an RNA genome. "Gammaretrovirus" refers to a genus of the retroviridae family. Exemplary gammaretroviruses include mouse stem cell virus, murine leukemia virus, feline leukemia virus, feline sarcoma virus, and avian reticuloendotheliosis viruses.

Retroviral vectors (see Miller, et al., 1993, *Meth. Enzymol.* 217:581-599) can be used. In such embodiments, the gene to be expressed is cloned into the retroviral vector for its delivery into cells. In particular embodiments, a retroviral vector includes all of the cis-acting sequences necessary for the packaging and integration of the viral genome, i.e., (a) a long terminal repeat (LTR), or portions thereof, at each end of the vector; (b) primer binding sites for negative and positive strand DNA synthesis; and (c) a packaging signal, necessary for the incorporation of genomic RNA into virions. More detail about retroviral vectors can be found in Boesen, et al., 1994, *Biotherapy* 6:291-302; Clowes, et al., 1994, *J. Clin. Invest.* 93:644-651; Kiem, et al., 1994, *Blood* 83:1467-1473; Salmons and Gunzberg, 1993, *Human Gene Therapy* 4:129-141; and Grossman and Wilson, 1993, *Curr. Opin. in Genetics and Devel.* 3:110-114. Adenoviruses, adeno-associated viruses (AAV) and alphaviruses can also be used. See Kozarsky and Wilson, 1993, *Current Opinion in Genetics and Development* 3:499-503, Rosenfeld, et al., 1991, *Science* 252:431-434; Rosenfeld, et al., 1992, *Cell* 68:143-155; Mastrangeli, et al., 1993, *J. Clin. Invest.* 91:225-234; Walsh, et al., 1993, *Proc. Soc. Exp. Bioi. Med.* 204:289-300; and Lundstrom, 1999, *J. Recept. Signal Transduct. Res.* 19: 673-686. Other methods of gene delivery include use of mammalian artificial chromosomes (Vos, 1998, *Curr. Op. Genet. Dev.* 8:351-359); liposomes (Tarahovsky and Ivanitsky, 1998, *Biochemistry* (Mosc) 63:607-618); ribozymes (Branch and Klotman, 1998, *Exp. Nephrol.* 6:78-83); and triplex DNA (Chan and Glazer, 1997, *J. Mol. Med.* 75:267-282).

There are a large number of available viral vectors suitable within the current disclosure, including those identified for human gene therapy applications (see Pfeifer and Verma, 2001, *Ann. Rev. Genomics Hum. Genet.* 2:177). Methods of using retroviral and lentiviral viral vectors and packaging cells for transducing mammalian host cells with viral particles including CAR transgenes are described in, e.g., U.S. Pat. No. 8,119,772; Walchli, et al., 2011, *PLoS One* 6:327930; Zhao, et al., 2005, *J. Immunol.* 174:4415; Engels, et al., 2003, *Hum. Gene Ther.* 14:1155; Frecha, et al., 2010, *Mol. Ther.* 18:1748; and Verhoeyen, et al., 2009, *Methods Mol. Biol.* 506:97. Retroviral and lentiviral vector constructs and expression systems are also commercially available.

Targeted genetic engineering approaches may also be utilized to either (i) insert a gene for expression of a TNFRS family member whose activity should be potentiated and/or (ii) disrupt the activity of a TNFRS family member to be inhibited. In particular embodiments, disrupting the activity of these family members can be based on disrupting their coding sequences and/or expression utilizing targeted genetic engineering approaches.

The CRISPR (Clustered Regularly Interspaced Short Palindromic Repeats)/Cas (CRISPR-associated protein) nuclease system is an engineered nuclease system used for genetic engineering that is based on a bacterial system. Information regarding CRISPR-Cas systems and components thereof are described in, for example, U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, WO2016205711, WO2017/106657, WO2017/127807 and applications related thereto.

Particular embodiments utilize zinc finger nucleases (ZFNs) as gene editing agents. ZFNs are a class of site-specific nucleases engineered to bind and cleave DNA at specific positions. ZFNs are used to introduce double stranded breaks (DSBs) at a specific site in a DNA sequence which enables the ZFNs to target unique sequences within a genome in a variety of different cells.

For additional information regarding ZFNs and ZFNs useful within the teachings of the current disclosure, see, e.g., U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; 6,479,626; US 2003/0232410 and US 2009/0203140 as well as Gaj et al., Nat Methods, 2012, 9(8):805-7; Ramirez et al., Nucl Acids Res, 2012, 40(12):5560-8; Kim et al., Genome Res, 2012, 22(7): 1327-33; Urnov et al., Nature Reviews Genetics, 2010, 11:636-646; Miller, et al. Nature biotechnology 25, 778-785 (2007); Bibikova, et al. Science 300, 764 (2003); Bibikova, et al. Genetics 161, 1169-1175 (2002); Wolfe, et al. Annual review of biophysics and biomolecular structure 29, 183-212 (2000); Kim, et al. Proceedings of the National Academy of Sciences of the United States of America 93, 1156-1160 (1996); and Miller, et al. The EMBO journal 4, 1609-1614 (1985).

Particular embodiments can use transcription activator like effector nucleases (TALENs) as gene editing agents. TALENs refer to fusion proteins including a transcription activator-like effector (TALE) DNA binding protein and a DNA cleavage domain. TALENs are used to edit genes and genomes by inducing double DSBs in the DNA, which induce repair mechanisms in cells. Generally, two TALENs must bind and flank each side of the target DNA site for the DNA cleavage domain to dimerize and induce a DSB. For additional information regarding TALENs, see U.S. Pat. Nos. 8,440,431; 8,440,432; 8,450,471; 8,586,363; and 8,697,853; as well as Joung and Sander, Nat Rev Mol Cell Biol, 2013, 14(1):49-55; Beurdeley et al., Nat Commun, 2013, 4: 1762; Scharenberg et al., Curr Gene Ther, 2013, 13(4):291-303; Gaj et al., Nat Methods, 2012, 9(8):805-7; Miller, et al. Nature biotechnology 29, 143-148 (2011); Christian, et al. Genetics 186, 757-761 (2010); Boch, et al. Science 326, 1509-1512 (2009); and Moscou, & Bogdanove, Science 326, 1501 (2009).

Particular embodiments can utilize MegaTALs as gene editing agents. MegaTALs have a sc rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the megaTAL only requires the delivery of a single peptide chain for functional activity.

Nanoparticles that result in selective in vivo genetic modification of targeted cell types have been described and can be used within the teachings of the current disclosure. In particular embodiments, the nanoparticles can be those described in WO2014153114, WO2017181110, and WO201822672.

(III-B) CAR Subcomponents. As described previously, CAR molecules include several distinct subcomponents that allow genetically modified cells to recognize and kill unwanted cells, such as cancer cells. The subcomponents include at least an extracellular component and an intracellular component. The extracellular component includes a binding domain that specifically binds an antigen marker that is preferentially present on the surface of unwanted cells. When the binding domain binds such antigen markers, the intracellular component activates the cell to destroy the bound cell. CAR additionally include a transmembrane domain that links the extracellular component to the intracellular component, and other subcomponents that can increase the CAR's function. For example, the inclusion of a spacer region and/or one or more linker sequences can allow the CAR to have additional conformational flexibility, often increasing the binding domain's ability to bind the targeted cell marker.

(III-B-i) Binding Domains & Targeted Cellular Antigens. Binding domains include any substance that binds to a cellular antigen to form a complex. The choice of binding domain can depend upon the type and number of cellular antigens that define the surface of a target cell. Examples of binding domains include cellular antigen ligands, receptor ligands, antibodies, peptides, peptide aptamers, receptors (e.g., T cell receptors), or combinations and engineered fragments or formats thereof.

Antibodies are one example of binding domains and include whole antibodies or binding fragments of an antibody, e.g., Fv, Fab, Fab', F(ab')2, and single chain (sc) forms and fragments thereof that bind specifically to a cellular antigen. Antibodies or antigen binding fragments can include all or a portion of polyclonal antibodies, monoclonal antibodies, human antibodies, humanized antibodies, synthetic antibodies, non-human antibodies, recombinant antibodies, chimeric antibodies, bispecific antibodies, mini bodies, and linear antibodies. Functional fragments thereof, include a single-domain antibody such as a heavy chain variable domain (VH), a light chain variable domain (VL) and a variable domain (VHH) of camelid derived nanobody, and the like.

In some instances, scFvs can be prepared according to methods known in the art (see, for example, Bird et al., (1988) Science 242:423-426 and Huston et al., (1988) Proc. Natl. Acad. Sci. USA 85:5879-5883). ScFv molecules can be produced by linking VH and VL regions of an antibody together using flexible polypeptide linkers. If a short polypeptide linker is employed (e.g., between 5-10 amino acids) intrachain folding is prevented. Interchain folding is also required to bring the two variable regions together to form a functional epitope binding site. For examples of linker orientations and sizes see, e.g., Hollinger et al. 1993 Proc Natl Acad. Sci. U.S.A. 90:6444-6448, US 2005/0100543, US 2005/0175606, US 2007/0014794, and WO2006/020258 and WO2007/024715.

An scFv can include a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. In particular embodiments, the linker sequence may include any naturally occurring amino acid. Generally, linker sequences that are used to connect the VH and VL of an scFv are five to 35 amino acids in length. In particular embodiments, a VH-VL linker includes from five to 35, ten to 30 amino acids or from 15 to 25 amino acids. Variation in the linker length may retain or enhance activity, giving rise to superior efficacy in activity studies.

In some embodiments, the linker sequence includes the amino acids glycine and serine. In particular embodiments, the linker sequence includes sets of glycine and serine repeats such as from one to ten repeats of $(Gly_xSer_y)_n$, wherein x and y are independently an integer from 0 to 10 provided that x and y are not both 0 and wherein n is an integer of 1, 2, 3, 4, 5, 6, 7, 8, 9 or 10) and wherein linked VH-VL regions form a functional immunoglobulin-like binding domain (e.g., scFv, scTCR). Particular examples include $(Gly_4Ser)_n$ (SEQ ID NO: 1), $(Gly_3Ser)_n(Gly_4Ser)_n$ (SEQ ID NO: 2), $(Gly_3Ser)_n(Gly_2Ser)_n$ (SEQ ID NO: 3), $(Gly_3Ser)_n(Gly_4Ser)_1$ (SEQ ID NO: 4), $(Gly_4Ser)_1$ (SEQ ID NO: 5), $(Gly_3Ser)_1$ (SEQ ID NO: 6), or $(Gly_2Ser)_1$. In particular embodiments, the linker is $(Gly_4Ser)_4$ (SEQ ID NO: 7) or $(Gly_4Ser)_3$ (SEQ ID NO: 8). As indicated through reference to scTCR above, such linkers can also be used to link T cell receptor $V_{\alpha/\beta}$ and $C_{\alpha/\beta}$ chains (e.g., $V_\alpha$-$C_\alpha$, $V_\beta$-$C_\beta$, $V_\alpha$-$V_\beta$).

Additional examples include scFv-based grababodies and soluble VH domain antibodies. These antibodies form binding regions using only heavy chain variable regions. See, for example, Jespers et al., Nat. Biotechnol. 22:1161, 2004; Cortez-Retamozo et al., Cancer Res. 64:2853, 2004; Baral et al., Nature Med. 12:580, 2006; and Barthelemy et al., J. Biol. Chem. 283:3639, 2008.

In some instances, it is beneficial for the binding domain to be derived from the same species it will ultimately be used in. For example, for use in humans, it may be beneficial for the antigen binding domain to include a human antibody, humanized antibody, or a fragment or engineered form thereof. Antibodies from human origin or humanized antibodies have lowered or no immunogenicity in humans and have a lower number of non-immunogenic epitopes compared to non-human antibodies. Antibodies and their engineered fragments will generally be selected to have a reduced level or no antigenicity in human subjects.

In particular embodiments, the binding domain includes a humanized antibody or an engineered fragment thereof. In some aspects, a non-human antibody is humanized, where one or more amino acid residues of the antibody are modified to increase similarity to an antibody naturally produced in a human or fragment thereof. These nonhuman amino acid residues are often referred to as "import" residues, which are typically taken from an "import" variable domain. As provided herein, humanized antibodies or antibody fragments include one or more CDRs from nonhuman immunoglobulin molecules and framework regions wherein the amino acid residues including the framework are derived completely or mostly from human germline. In one aspect, the antigen binding domain is humanized. A humanized antibody can be produced using a variety of techniques known in the art, including CDR-grafting (see, e.g., European Patent No. EP 239,400; WO 91/09967; and U.S. Pat. Nos. 5,225,539, 5,530,101, and 5,585,089), veneering or resurfacing (see, e.g., EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973), chain shuffling (see, e.g., U.S. Pat. No. 5,565,332), and techniques disclosed in, e.g., US 2005/0042664, US 2005/0048617, U.S. Pat. Nos. 6,407,213, 5,766,886, WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16): 10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994). Often, framework residues in the framework regions will be substituted with the corresponding residue from the CDR donor antibody to alter, for example improve, cellular antigen binding. These framework substitutions are identified by methods well-known in the art, e.g., by modeling of the interactions of the CDR and framework residues to identify framework residues important for cellular antigen binding and sequence comparison to identify unusual framework residues at particular positions. (See, e.g., U.S. Pat. No. 5,585,089; and Riechmann et al., 1988, Nature, 332:323).

Antibodies that specifically bind a particular cellular antigen can be prepared using methods of obtaining monoclonal antibodies, methods of phage display, methods to generate human or humanized antibodies, or methods using a transgenic animal or plant engineered to produce antibodies as is known to those of ordinary skill in the art (see, for example, U.S. Pat. Nos. 6,291,161 and 6,291,158). Phage display libraries of partially or fully synthetic antibodies are available and can be screened for an antibody or fragment thereof that can bind to a cellular antigen. For example, binding domains may be identified by screening a Fab phage library for Fab fragments that specifically bind to a cellular antigen of interest (see Hoet et al., Nat. Biotechnol. 23:344, 2005). Phage display libraries of human antibodies are also available. Additionally, traditional strategies for hybridoma development using a cellular antigen of interest as an immunogen in convenient systems (e.g., mice, HuMAb Mouse® (GenPharm Int'l. Inc., Mountain View, CA), TC Mouse® (Kirin Pharma Co. Ltd., Tokyo, JP), KM-Mouse® (Medarex, Inc., Princeton, NJ), llamas, chicken, rats, hamsters, rabbits, etc.) can be used to develop binding domains. In particular embodiments, antibodies specifically bind to a cellular antigen preferentially expressed by a particular unwanted cell type and do not cross react with nonspecific components or unrelated targets. Once identified, the amino acid sequence of the antibody and gene sequence encoding the antibody can be isolated and/or determined.

An alternative source of binding domains includes sequences that encode random peptide libraries or sequences that encode an engineered diversity of amino acids in loop regions of alternative non-antibody scaffolds, such as scTCR (see, e.g., Lake et al., Int. Immunol. 11:745, 1999; Maynard et al., J. Immunol. Methods 306:51, 2005; U.S. Pat. No. 8,361,794), fibrinogen domains (see, e.g., Weisel et al., Science 230:1388, 1985), Kunitz domains (see, e.g., U.S. Pat. No. 6,423,498), designed ankyrin repeat proteins (DARPins; Binz et al., J. Mol. Biol. 332:489, 2003 and Binz et al., Nat. Biotechnol. 22:575, 2004), fibronectin binding domains (adnectins or monobodies; Richards et al., J. Mol. Biol. 326:1475, 2003; Parker et al., Protein Eng. Des. Selec. 18:435, 2005 and Hackel et al. (2008) J. Mol. Biol. 381: 1238-1252), cysteine-knot miniproteins (Vita et al., 1995, Proc. Nat'l. Acad. Sci. (USA) 92:6404-6408; Martin et al., 2002, Nat. Biotechnol. 21:71, 2002 and Huang et al. (2005) Structure 13:755, 2005), tetratricopeptide repeat domains (Main et al., Structure 11:497, 2003 and Cortajarena et al., ACS Chem. Biol. 3:161, 2008), leucine-rich repeat domains (Stumpp et al., J. Mol. Biol. 332:471, 2003), lipocalin domains (see, e.g., WO 2006/095164, Beste et al., Proc. Nat'l. Acad. Sci. (USA) 96:1898, 1999 and Schönfeld et al., Proc. Nat'l. Acad. Sci. (USA) 106:8198, 2009), V-like domains (see, e.g., US 2007/0065431), C-type lectin domains (Zelensky and Gready, FEBS J. 272:6179, 2005; Beavil et al., Proc. Nat'l. Acad. Sci. (USA) 89:753, 1992 and Sato et al., Proc. Nat'l. Acad. Sci. (USA) 100:7779, 2003), mAb2 or Fc-region with antigen binding domain (Fcab™ (F-Star Biotechnology, Cambridge UK; see, e.g., WO 2007/098934 and WO 2006/072620), armadillo repeat proteins (see, e.g., Madhurantakam et al., Protein Sci. 21: 1015, 2012; WO 2009/040338), affilin (Ebersbach et al., J. Mol. Biol. 372: 172, 2007), affibody, avimers, knottins, fynomers, atrimers, cytotoxic T-lymphocyte associated protein-4 (Weidle et al., Cancer Gen. Proteo. 10:155, 2013), or the like (Nord et al., Protein Eng. 8:601, 1995; Nord et al., Nat. Biotechnol. 15:772, 1997; Nord et al., Euro. J. Biochem. 268:4269, 2001; Binz et al., Nat. Biotechnol. 23:1257, 2005; Boersma and Plückthun, Curr. Opin. Biotechnol. 22:849, 2011).

Peptide aptamers include a peptide loop (which is specific for a cellular antigen) attached at both ends to a protein scaffold. This double structural constraint increases the binding affinity of peptide aptamers to levels comparable to antibodies. The variable loop length is typically 8 to 20 amino acids and the scaffold can be any protein that is stable, soluble, small, and non-toxic. Peptide aptamer selection can be made using different systems, such as the yeast two-hybrid system (e.g., Gal4 yeast-two-hybrid system), or the LexA interaction trap system.

In particular embodiments, a binding domain is a sc T cell receptor (scTCR) including Vα/β and Cα/β chains (e.g., Vα-Cα, Vβ-Cβ, Vα-Vβ) or including a Vα-Cα, Vβ-CR, Vα-Vβ pair specific for a cellular antigen of interest (e.g., peptide-MHC complex).

In particular embodiments, engineered CAR include a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a known or identified TCR Vα, Vβ, Cα, or Cβ, wherein each CDR includes zero changes or at most one, two, or three changes, from a TCR or fragment or derivative thereof that specifically binds to the targeted cellular antigen.

In particular embodiments, engineered CAR include Vα, Vβ, Cα, or Cβ regions derived from or based on a Vα, Vβ, Cα, or Cβ of a known or identified TCR (e.g., a high-affinity TCR) and includes one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the Vα, Vβ, Cα, or Cβ of a known or identified TCR. An insertion, deletion or substitution may be anywhere in a Vα, Vβ, Cα, or Cβ region, including at the amino- or carboxy-terminus or both ends of these regions, provided that each CDR includes zero changes or at most one, two, or three changes and provides a target binding domain containing a modified Vα, Vβ, Cα, or Cβ region can still specifically bind its target with an affinity and action similar to wild type.

Binding domains can be selected to bind numerous cellular antigens associated with unwanted cell types, such as cancer cell markers. Exemplary cellular antigens include A33; BAGE; Bcl-2; β-catenin; BCMA; B7H4; BTLA; CA125; CA19-9; CD3, CD5; CD20; CD21; CD22; CD25; CD28; CD30; CD33; CD37; CD38; CD40; CD52; CD44v6; CD45; CD56; CD79b; CD80; CD81; CD86; CD123; CD134; CD137; CD151; CD171; CD276; CEA; CEACAM6; c-Met; CS-1; CTLA-4; cyclin 1; DAGE; EBNA; EGFR; EGFRvIII, ephrinB2; ErbB2; ErbB3; ErbB4; EphA2; estrogen receptor; FAP; ferritin; α-fetoprotein (AFP); FLT1; FLT4; folate-binding protein; FOLR; Frizzled; GAGE; G250; GD-2; GHRHR; GHR; GITR; GM2; GPRC5D; gp75; gp100 (Pmel 17); gp130; HLA; HER-2/neu; HPV E6; HPV E7; hTERT; HVEM; IGF1R; IL6R; KDR; Ki-67; Lewis A; Lewis Y; LIFRP; LRP; LRP5; LTPR; MAGE; MART; mesothelin; MUC; MUC1; MUM-1-B; myc; NYESO-1; O-acetyl GD-2; O-acetyl GD3; OSMRR; p53; PD1; PD-L1; PD-L2; PRAME; progesterone receptor; PSA; PSMA; PTCH1; RANK; ras; Robo1; RORI; survivin; TCRα; TCRβ; tenascin; TGFBR1; TGFBR2; TLR7; TLR9; TNFR1; TNFR2; TNFRSF4; TWEAK-R; TSTA tyrosinase; VEGF; and WTI1.

Particular cellular antigens associated with prostate cancer include PSMA, WT1, ProstateStem Cell antigen (PSCA), and SV40 T. Particular antigens associated with breast cancer include HER2 and ERBB2. Particular cellular antigens associated with ovarian cancer include L1-CAM, extracellular domain of MUC16 (MUC-CD), folate binding protein (folate receptor), Lewis Y, mesothelin, and WT-1. Particular cellular antigens associated with pancreatic cancer include mesothelin, CEA and CD24. Particular cellular antigens associated with multiple myeloma include BCMA, GPRC5D, CD38, and CS-1. Particular antigens associated with leukemia and/or lymphoma include CLL-1, CD123, CD33, and PD-1.

In particular embodiments, the binding domain of a CAR can bind CD33. In particular embodiments, the binding domain of a CAR binds the cellular antigen CD33. In particular embodiments, the binding domain that binds CD33 is derived from one of gemtuzumab, aclizumab, or HuM195. In particular embodiments a CD33 binding domain is a human or humanized binding domain including a variable light chain including a CDRL1 sequence including TASSSVNYIH (SEQ ID NO: 14), a CDRL2 sequence including TSKVAS (SEQ ID NO: 15), and a CDRL3 sequence including QQWRSYPLT (SEQ ID NO: 16), and a variable heavy chain including a CDRH1 sequence including DYVVH (SEQ ID NO: 17), a CDRH2 sequence including YINPYNDGTKYNEKFKG (SEQ ID NO: 18), and a CDRH3 sequence including DYRYEVYGMDY (SEQ ID NO: 19).

In particular embodiments, a CD33 binding domain is a human or humanized scFv including a variable light chain including a CDRL1 sequence including RASEVDNYGISFMN (SEQ ID NO: 20), a CDRL2 sequence including AASNQGS (SEQ ID NO: 21), and a CDRL3 sequence including QQSKEVPW (SEQ ID NO: 22), and a variable heavy chain including a CDRH1 sequence including DYNMH (SEQ ID NO: 23), a CDRH2 sequence including YIYPYNGGTGYNQKFKS (SEQ ID NO: 24), and a CDRH3 sequence including GRPAMDY (SEQ ID NO: 25). For more information regarding binding domains that bind CD33, see U.S. Pat. No. 8,759,494.

In particular embodiments, a sequence that binds human CD33 includes a variable light chain including sequence:

```
                                              (SEQ ID NO: 26
DIVLTQSPTIMSASPGERVTMTCTASSSVNYIHWYQQKSGDSPKRWIFDT

SKVASGVPARFSGSGSGTSYSLTISTMEAEDAATYYCQQWRSYPLTFGDG

TRLELKRADAAPTVS,
```

and a variable heavy chain including sequence:

```
                                              (SEQ ID NO: 27)
EVKLQESGPELVKPGASVKMSCKASGYKFTDYVVHWLKQKPGQGLEWIGY

INPYNDGTKYNEKFKGKATLTSDKSSSTAYMEVSSLTSEDSAVYYCARDY

RYEVYGMDYWGQGTSVTVSS.
```

In particular embodiments, a sequence that binds human CD33 includes a variable light chain including sequence:

```
                                              (SEQ ID NO: 26)
DIVLTQSPTIMSASPGERVTMTCTASSSVNYIHWYQQKSGDSPKRWIFDT

SKVASGVPARFSGSGSGTSYSLTISTMEAEDAATYYCQQWRSYPLTFGDG

TRLELKRADAAPTVS.
```

and a variable heavy chain including sequence.

```
                                              (SEQ ID NO: 28)
DIVLTQSPAIMSASPGEKVTMTCSANSSVSYIHWYQQKSGTSPKRWIFDT

SKLASGVPARFSGSGSGTSYSLTISTMEAEDAATYYCQQWTSHPLTFGTG

TKLQLKRADAAPTVS.
```

In particular embodiments, the binding domain of a CAR binds the cellular antigen CD33DeltaE2 (CD33ΔE2). In particular embodiments, the binding domain that binds CD33ΔE2 is derived from 1H7. In particular embodiments, a 1H7 binding domain includes a variable light chain including a CDRL1 sequence including RASQDINYYLN (SEQ ID NO: 45), a CDRL2 sequence including YYSSRLHS (SEQ ID NO: 46), a CDRL3 sequence including QQDDALPYT (SEQ ID NO: 47), a CDRH1 sequence including KASGYAFSNYWMN (SEQ ID NO: 48), a CDRH2 sequence including QINPGDGDTN (SEQ ID NO: 49), and a CDRH3 sequence including AREDRDYFDY (SEQ ID NO: 50). This CDR set is according to North.

In particular embodiments, a 1H7 binding domain includes a variable light chain including a CDRL1 sequence including QDINYY (SEQ ID NO: 163), a CDRL2 sequence including YSS, a CDRL3 sequence including QQDDALPYT (SEQ ID NO: 47), a CDRH1 sequence including GYAFSNYW (SEQ ID NO: 164), a CDRH2 sequence including INPGDGDT (SEQ ID NO: 165), and a CDRH3 sequence including AREDRDYFDY (SEQ ID NO: 50). This CDR set is according to IMGT.

In particular embodiments, a 1H7 binding domain includes a variable light chain including a CDRL1 sequence including RASQDINYYLN (SEQ ID NO: 45), a CDRL2 sequence including YSSRLHS (SEQ ID NO: 166), a CDRL3 sequence including QQDDALPYT (SEQ ID NO:

47), a CDRH1 sequence including NYWMN (SEQ ID NO: 167), a CDRH2 sequence including QINPGDGDTNYNGKFKG (SEQ ID NO: 168), and a CDRH3 sequence including EDRDYFDY (SEQ ID NO: 169). This CDR set is according to Kabat.

In particular embodiments, a 1H7 binding domain includes a variable light chain including a CDRL1 sequence including RASQDINYYLN (SEQ ID NO: 45), a CDRL2 sequence including YSSRLHS (SEQ ID NO: 166), a CDRL3 sequence including QQDDALPYT (SEQ ID NO: 47), a CDRH1 sequence including GYAFSNY (SEQ ID NO: 170), a CDRH2 sequence including NPGDGD (SEQ ID NO: 171), and a CDRH3 sequence including EDRDYFDY (SEQ ID NO: 169). This CDR set is according to Chothia.

In particular embodiments, a 1H7 binding domain includes a variable light chain including the sequence:

(SEQ ID NO: 51)
DIQMTQTTSSLSASLGDRVTISCRASQDINYYLNWYQQKPDGTVKLLIYY

SSRLHSGVPSRFSGSGSGTDFSLTISNLEQEDIATYFCQQDDALPYTFGG

GTKLEIK and a variable heavy chain including the sequence:

(SEQ ID NO: 52)
QVQLQQSGAELVKPGASVKISCKASGYAFSNYWMNWVKQRPGKGLEWIGQ

INPGDGDTNYNGKFKGKATLTADKSSSTAYMQLSSLTSEDSAVYFCARED

RDYFDYWGQGTTLTVSS.

In particular embodiments, the binding domain of a CAR binds the cellular antigen Her2. In particular embodiments, the binding domain that binds HER2 is derived from trastuzumab (Herceptin). In particular embodiments, the binding domain includes a variable light chain including a CDRL1 sequence including KASQDVSIGVA (SEQ ID NO: 53), a CDRL2 sequence including ASYRYT (SEQ ID NO: 54), and a CDRL3 sequence including QQYYIYPYT (SEQ ID NO: 55), and a variable heavy chain including a CDRH1 sequence including GFTFTDYTMD (SEQ ID NO: 56), a CDRH2 sequence including DVNPNSGGSIYNQRFK (SEQ ID NO: 57), and a CDRH3 sequence including LGPSFYFDY (SEQ ID NO: 58).

In particular embodiments, the binding domain of a CAR binds the cellular antigen PD-1. In particular embodiments, the binding domain that binds PD-L1 is derived from at least one of pembrolizumab or FAZ053 (Novartis). In particular embodiments, the binding domain includes a variable light chain including a CDRL1 sequence including RASKGVSTSGYSYLH (SEQ ID NO: 59), a CDRL2 sequence including LASYLES (SEQ ID NO: 60), and a CDRL3 sequence including QHSRDLPLT (SEQ ID NO: 61), and a variable heavy chain including a CDRH1 sequence including NYYMY (SEQ ID NO: 62), a CDRH2 sequence including GINPSNGGTNFNEKFKN (SEQ ID NO: 63), and a CDRH3 sequence including RDYRFDMGFDY (SEQ ID NO: 64).

An exemplary binding domain for PD-L1 can include or be derived from Avelumab or Atezolizumab. In particular embodiments, the variable light chain of Avelumab includes:

(SEQ ID NO: 65)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRV

FGTGTKVTVL.

In particular embodiments, the variable heavy chain of Avelumab includes:

(SEQ ID NO: 66)
EVQLLESGGGLVQPGGSLRLSCAASGFTFSSYIMMWVRQAPGKGLEWVSS

IYPSGGITFYADTVKGRFTISRDNSKNTLYLQMNSLRAEDTAVYYCARIK

LGTVTTVDYWGQGTLVTVSS.

In particular embodiments, the CDR regions of Avelumab include: CDRL1: TGTSSDVGGYNYVS (SEQ ID NO: 67); CDRL2: DVSNRPS (SEQ ID NO: 68); CDRL3: SSYTSSSTRV (SEQ ID NO: 69); CDRH1: SGFTFSSYIMM (SEQ ID NO: 70); CDRH2: SIYPSGGITFYADTVKG (SEQ ID NO: 71); and CDRH3: IKLGTVTTVDY (SEQ ID NO: 72).

In particular embodiments, the variable light chain of Atezolizumab includes:

(SEQ ID NO: 73)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIK.

In particular embodiments, the variable heavy chain of Atezolizumab includes:

(SEQ ID NO: 74)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS.

In particular embodiments, the CDR regions of Atezolizumab include: CDRL1: RASQDVSTAVA (SEQ ID NO: 75); CDRL2: SASFLYS (SEQ ID NO: 76); CDRL3: QQYLYHPAT (SEQ ID NO: 77); CDRH1: SGFTFSDSWIH (SEQ ID NO: 78); CDRH2: WISPYGGSTYYADSVKG (SEQ ID NO: 79); and CDRH3: RHWPGGFDY (SEQ ID NO: 80).

In particular embodiments, the binding domain of a CAR binds the cellular antigen PSMA. In particular embodiments, the binding domain includes a variable light chain including a CDRL1 sequence including KASQDVGTAVD (SEQ ID NO: 81), a CDRL2 sequence including WASTRHT (SEQ ID NO: 82), a CDRL3 sequence including QQYNSYPLT (SEQ ID NO: 83). In particular embodiments, the binding domain includes a variable heavy chain including a CDRH1 sequence including GYTFTEYTIH (SEQ ID NO: 84), a CDRH2 sequence including NINPNNGGTTYNQKFED (SEQ ID NO: 85), and a CDRH3 sequence including GWNFDY (SEQ ID NO: 86).

An exemplary binding domain for mesothelin can include or be derived from Amatuximab.

In particular embodiments, the variable light chain of Amatuximab includes:

(SEQ ID NO: 98)
DIELTQSPAIMSASPGEKVTMTCSASSSVSYMHWYQQKSGTSPKRWIYDT
SKLASGVPGRFSGSGSGNSYSLTISSVEAEDDATYYCQQWSKHPLTFGSG
TKVEIK.

In particular embodiments, the variable heavy chain of Amatuximab includes:

(SEQ ID NO: 99)
QVQLQQSGPELEKPGASVKISCKASGYSFTGYTMNWVKQSHGKSLEWIGL
ITPYNGASSYNQKFRGKATLTVDKSSSTAYMDLLSLTSEDSAVYFCARGG
YDGRGFDYWGSGTPVTVSS.

In particular embodiments, the CDR regions of Amatuximab include:
CDRL1: SASSSVSYMH (SEQ ID NO: 100); CDRL2: DTSKLAS (SEQ ID NO: 101); and CDRL3: QQWSKHPLT (SEQ ID NO: 102); CDRH1: GYSFTGYTMN (SEQ ID NO: 103); CDRH2: LITPYNGASSYNQ (SEQ ID NO: 104); and CDRH3: GGYDGRGFDY (SEQ ID NO: 105).

As indicated previously, binding domains can adopt a variety of engineered formats including, for example, Fab fragments, scFv, scFv-based grababodies, and soluble VH domain antibodies.

In particular embodiments, a binding domain of a CAR includes or is a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a light chain variable region (VL) or to a heavy chain variable region (VH), or both, wherein each CDR includes zero changes or at most one, two, or three changes, from a monoclonal antibody or fragment or derivative thereof that specifically binds to a cellular antigen of interest.

In particular embodiments, a binding domain VH region of the present disclosure can be derived from or based on a VH of a known monoclonal antibody and can contain one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the VH of a known monoclonal antibody. An insertion, deletion or substitution may be anywhere in the VH region, including at the amino- or carboxy-terminus or both ends of this region, provided that each CDR includes zero changes or at most one, two, or three changes and provided a binding domain containing the modified VH region can still specifically bind its target with an affinity similar to the wild type binding domain.

In particular embodiments, a VL region in a binding domain of the present disclosure is derived from or based on a VL of a known monoclonal antibody and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared with the VL of the known monoclonal antibody. An insertion, deletion or substitution may be anywhere in the VL region, including at the amino- or carboxy-terminus or both ends of this region, provided that each CDR includes zero changes or at most one, two, or three changes and provided a binding domain containing the modified VL region can still specifically bind its target with an affinity similar to the wild type binding domain.

The precise amino acid sequence boundaries of a given CDR or FR can be readily determined using any of a number of well-known schemes, including those described by: Kabat et al. (1991) "Sequences of Proteins of Immunological Interest," 5th Ed. Public Health Service, National Institutes of Health, Bethesda, Md. (Kabat numbering scheme); Al-Lazikani et al. (1997) J Mol Biol 273: 927-948 (Chothia numbering scheme); Maccallum et al. (1996) J Mol Biol 262: 732-745 (Contact numbering scheme); Martin et al. (1989) Proc. Natl. Acad. Sci., 86: 9268-9272 (AbM numbering scheme); Lefranc M P et al. (2003) Dev Comp Immunol 27(1): 55-77 (IMGT numbering scheme); and Honegger and Pluckthun (2001) J Mol Biol 309(3): 657-670 ("Aho" numbering scheme). The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. In particular embodiments, the antibody CDR sequences disclosed herein are according to Kabat numbering.

(III-B-ii) Spacer Regions. Spacer regions are used to create appropriate distances and/or flexibility from other CAR sub-components. As indicated, in particular embodiments, the length of a spacer region is customized for binding a particular cellular antigen and mediating destruction. In particular embodiments, a spacer region length can be selected based upon the location of a cellular antigen epitope, affinity of a binding domain for the epitope, and/or the ability of the targeting agent to mediate cell destruction following binding to the cellular antigen.

Spacer regions typically include those having 10 to 250 amino acids, 10 to 200 amino acids, 10 to 150 amino acids, 10 to 100 amino acids, 10 to 50 amino acids, or 10 to 25 amino acids.

In particular embodiments, a spacer region is 5 amino acids, 8 amino acids, 10 amino acids, 12 amino acids, 14 amino acids, 20 amino acids, 21 amino acids, 26 amino acids, 27 amino acids, 45 amino acids, or 50 amino acids. These lengths qualify as short spacer regions.

In particular embodiments, a spacer region is 100 amino acids, 110 amino acids, 120 amino acids, 125 amino acids, 128 amino acids, 131 amino acids, 135 amino acids, 140 amino acids, 150 amino acids, 160 amino acids, or 170 amino acids. These lengths qualify as intermediate spacer regions.

Long spacer regions have more than 170 amino acids.

Exemplary spacer regions include all or a portion of an immunoglobulin hinge region. An immunoglobulin hinge region may be a wild-type immunoglobulin hinge region or an altered wild-type immunoglobulin hinge region. In certain embodiments, an immunoglobulin hinge region is a human immunoglobulin hinge region. As used herein, a "wild type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of an antibody.

An immunoglobulin hinge region may be an IgG, IgA, IgD, IgE, or IgM hinge region. An IgG hinge region may be an IgG1, IgG2, IgG3, or IgG4 hinge region. Sequences from IgG1, IgG2, IgG3, IgG4 or IgD can be used alone or in combination with all or a portion of a CH2 region; all or a portion of a CH3 region; or all or a portion of a CH2 region and all or a portion of a CH3 region.

In particular embodiments, the spacer is a short spacer including an IgG4 hinge region. In particular embodiments the short spacer is SEQ ID NO: 129 or the sequence encoded by SEQ ID NO: 130. In particular embodiments, the spacer is an intermediate spacer including an IgG4 hinge region and an IgG4 hinge CH3 region. In particular embodiments the intermediate spacer is encoded by SEQ ID NO: 131. In particular embodiments, the spacer is a long spacer including an IgG4 hinge region, an IgG4 CH3 region, and an IgG4 CH2 region. In particular embodiments the long spacer is encoded by SEQ ID NO: 132.

Other examples of hinge regions that can be used CAR described herein include the hinge region present in the extracellular regions of type 1 membrane proteins, such as CD8a, CD4, CD28 and CD7, which may be wild-type or variants thereof.

In particular embodiments, a spacer region includes a hinge region that includes a type II C-lectin interdomain (stalk) region or a cluster of differentiation (CD) molecule stalk region. A "stalk region" of a type II C-lectin or CD molecule refers to the portion of the extracellular domain of the type II C-lectin or CD molecule that is located between the C-type lectin-like domain (CTLD; e.g., similar to CTLD of natural killer cell receptors) and the hydrophobic portion (transmembrane domain). For example, the extracellular domain of human CD94 (GenBank Accession No. AAC50291.1) corresponds to amino acid residues 34-179, but the CTLD corresponds to amino acid residues 61-176, so the stalk region of the human CD94 molecule includes amino acid residues 34-60, which are located between the hydrophobic portion (transmembrane domain) and CTLD (see Boyington et al., Immunity 10:15, 1999; for descriptions of other stalk regions, see also Beavil et al., Proc. Nat'l. Acad. Sci. USA 89:153, 1992; and Figdor et al., Nat. Rev. Immunol. 2:11, 2002). These type II C-lectin or CD molecules may also have junction amino acids (described below) between the stalk region and the transmembrane region or the CTLD. In another example, the 233 amino acid human NKG2A protein (GenBank Accession No. P26715.1) has a hydrophobic portion (transmembrane domain) ranging from amino acids 71-93 and an extracellular domain ranging from amino acids 94-233. The CTLD includes amino acids 119-231 and the stalk region includes amino acids 99-116, which may be flanked by additional junction amino acids. Other type II C-lectin or CD molecules, as well as their extracellular ligand-binding domains, stalk regions, and CTLDs are known in the art (see, e.g., GenBank Accession Nos. NP 001993.2; AAH07037.1; NP 001773.1; AAL65234.1; CAA04925.1; for the sequences of human CD23, CD69, CD72, NKG2A, and NKG2D and their descriptions, respectively).

(III-B-iii) Transmembrane Domains. As indicated, transmembrane domains within a CAR serve to connect the extracellular component and intracellular component through the cell membrane. The transmembrane domain can anchor the expressed molecule in the modified cell's membrane.

The transmembrane domain can be derived either from a natural and/or a synthetic source. When the source is natural, the transmembrane domain can be derived from any membrane-bound or transmembrane protein. Transmembrane domains can include at least the transmembrane region(s) of the α, β or ζ chain of a T-cell receptor, CD28, CD27, CD3 epsilon, CD45, CD4, CD5, CD8, CD9, CD16, CD22; CD33, CD37, CD64, CD80, CD86, CD134, CD137 and CD154. In particular embodiments, a transmembrane domain may include at least the transmembrane region(s) of, e.g., KIRDS2, OX40, CD2, CD27, LFA-1 (CD 11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2RP, IL2Rγ, IL7R a, ITGA1, VLA1, CD49a, ITGA4, IA4, CD49D, ITGA6, VLA-6, CD49f, ITGAD, CDI Id, ITGAE, CD103, ITGAL, CDI Ia, ITGAM, CDI Ib, ITGAX, CDI Ic, ITGB1, CD29, ITGB2, CD18, ITGB7, TNFR2, DNAM1(CD226), SLAMF4 (CD244, 2B4), CD84, CD96 (Tactile), CEACAM1, CRT AM, Ly9(CD229), PSGL1, CD100 (SEMA4D), SLAMF6 (NTB-A, Lyl08), SLAM (SLAMF1, CD150, IPO-3), BLAME (SLAMF8), SELPLG (CD162), LTBR, PAG/Cbp, NKG2D, or NKG2C. In particular embodiments, a variety of human hinges can be employed as well including the human Ig (immunoglobulin) hinge (e.g., an IgG4 hinge, an IgD hinge), a GS linker (e.g., a GS linker described herein), a KIR2DS2 hinge or a CD8a hinge.

In particular embodiments, a transmembrane domain has a three-dimensional structure that is thermodynamically stable in a cell membrane, and generally ranges in length from 15 to 30 amino acids. The structure of a transmembrane domain can include an α helix, a β barrel, a β sheet, a β helix, or any combination thereof.

A transmembrane domain can include one or more additional amino acids adjacent to the transmembrane region, e.g., one or more amino acid within the extracellular region of the CAR (e.g., up to 15 amino acids of the extracellular region) and/or one or more additional amino acids within the intracellular region of the CAR (e.g., up to 15 amino acids of the intracellular components). In one aspect, the transmembrane domain is from the same protein that the signaling domain, co-stimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins to minimize interactions with other unintended members of the receptor complex. In particular embodiments, the transmembrane domain is encoded by the nucleic acid sequence encoding the CD28 transmembrane domain (SEQ ID NOs: 133-136). In particular embodiments, the transmembrane domain includes the amino acid sequence of the CD28 transmembrane domain (SEQ ID NOs: 137 and 138).

(III-B-iv) Intracellular Effector Domains. The intracellular effector domains of a CAR are responsible for activation of the cell in which the CAR is expressed. The term "effector domain" is thus meant to include any portion of the intracellular domain sufficient to transduce an activation signal. An effector domain can directly or indirectly promote a biological or physiological response in a cell when receiving the appropriate signal. In certain embodiments, an effector domain is part of a protein or protein complex that receives a signal when bound, or it binds directly to a target molecule, which triggers a signal from the effector domain. An effector domain may directly promote a cellular response when it contains one or more signaling domains or motifs, such as an immunoreceptor tyrosine-based activation motif (ITAM). In other embodiments, an effector domain will indirectly promote a cellular response by associating with one or more other proteins that directly promote a cellular response, such as co-stimulatory domains.

Effector domains can provide for activation of at least one function of a modified cell upon binding to the cellular antigen expressed by a cancer cell. Activation of the modified cell can include one or more of differentiation, proliferation and/or activation or other effector functions. In particular embodiments, an effector domain can include an intracellular signaling component including a T cell receptor and a co-stimulatory domain which can include the cytoplasmic sequence from co-receptor or co-stimulatory molecule.

An effector domain can include one, two, three or more intracellular signaling components (e.g., receptor signaling domains, cytoplasmic signaling sequences), co-stimulatory domains, or combinations thereof. Exemplary effector domains include signaling and stimulatory domains selected from: 4-1BB (CD137), CARD11, CD3γ, CD3δ, CD3ε, CD3ζ, CD27, CD28, CD79A, CD79B, DAP10, FcRα, FcRβ (FcεR1b), FcRγ, Fyn, HVEM (LIGHTR), ICOS, LAG3, LAT, Lck, LRP, NKG2D, NOTCH1, pTα, PTCH2, OX40, ROR2, Ryk, SLAMF1, SIp76, TCRα, TCRβ, TRIM, Wnt, Zap70, or any combination thereof. In particular embodiments, exemplary effector domains include signaling and co-stimulatory domains selected from: CD86, FcγRIIa, DAP12, CD30, CD40, PD-1, lymphocyte function-associated antigen-1 (LFA-1), CD2, CD7, LIGHT, NKG2C, B7-H3, a ligand that specifically binds with CD83, CDS, ICAM-1, GITR, BAFFR, SLAMF7, NKp80 (KLRF1), CD127, CD160, CD19, CD4, CD8a, CD8P, IL2RP, IL2Rγ, IL7Rα, ITGA4, VLA1, CD49a, IA4, CD49D, ITGA6, VLA-6, CD49f, ITGAD, CD11d, ITGAE, CD103, ITGAL, CD11a, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), PSGL1, CD100 (SEMA4D), CD69, SLAMF6 (NTB-A, Ly108), SLAM (CD150, IPO-3), BLAME (SLAMF8), SELPLG (CD162), LTBR, GADS, PAG/Cbp, NKp44, NKp30, or NKp46.

Intracellular signaling component sequences that act in a stimulatory manner may include iTAMs. Examples of iTAMs including primary cytoplasmic signaling sequences include those derived from CD3γ, CD3δ, CD3ε, CD3ζ, CD5, CD22, CD66d, CD79a, CD79b, and common FcRγ (FCER1G), FcγRIIa, FcRβ (Fcε Rib), DAP10, and DAP12. In particular embodiments, variants of CD3ζ retain at least one, two, three, or all ITAM regions.

In particular embodiments, an effector domain includes a cytoplasmic portion that associates with a cytoplasmic signaling protein, wherein the cytoplasmic signaling protein is a lymphocyte receptor or signaling domain thereof, a protein including a plurality of ITAMs, a co-stimulatory domain, or any combination thereof.

Additional examples of intracellular signaling components include the cytoplasmic sequences of the CD3ζ chain, and/or co-receptors that act in concert to initiate signal transduction following binding domain engagement.

A co-stimulatory domain is a domain whose activation can be required for an efficient lymphocyte response to cellular antigen binding. Some molecules are interchangeable as intracellular signaling components or co-stimulatory domains. Examples of costimulatory domains include CD27, CD28, 4-1BB (CD 137), OX40, CD30, CD40, PD-1, ICOS, lymphocyte function-associated antigen-1 (LFA-1), CD2, CD7, LIGHT, NKG2C, B7-H3, and a ligand that specifically binds with CD83. For example, CD27 co-stimulation has been demonstrated to enhance expansion, effector function, and survival of human CART cells in vitro and augments human T cell persistence and anti-cancer activity in vivo (Song et al. Blood. 2012; 119(3):696-706). Further examples of such co-stimulatory domain molecules include CDS, ICAM-1, GITR, BAFFR, HVEM (LIGHTR), SLAMF7, NKp80 (KLRF1), NKp44, NKp30, NKp46, CD160, CD19, CD4, CD8α, CD8β, IL2Rβ, IL2Rγ, IL7Rα, ITGA4, VLA1, CD49a, ITGA4, IA4, CD49D, ITGA6, VLA-6, CD49f, ITGAD, CDIId, ITGAE, CD103, ITGAL, CDIIa, ITGAM, CDI Ib, ITGAX, CDIIc, ITGBI, CD29, ITGB2, CD18, ITGB7, TNFR2, TRANCE/RANKL, DNAM1 (CD226), SLAMF4 (CD244, 2B4), CD84, CD96 (Tactile), NKG2D, CEACAM1, CRTAM, Ly9 (CD229), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and CD19a.

In particular embodiments, the nucleic acid sequences encoding the intracellular signaling components includes CD3z encoding sequence (SEQ ID NOs: 139-141) and a variant of the 4-1BB signaling encoding sequence (SEQ ID NOs: 144-146). In particular embodiments, the amino acid sequence of the intracellular signaling component includes a variant of CD3ζ (SEQ ID NOs: 142 and 143) and a portion of the 4-1BB (SEQ ID NO: 147 and 148) intracellular signaling component.

In particular embodiments, the intracellular signaling component includes (i) all or a portion of the signaling domain of CD3ζ, (ii) all or a portion of the signaling domain of 4-1BB, or (iii) all or a portion of the signaling domain of CD3ζ and 4-1BB. In particular embodiments, the intracellular signaling component includes (i) all or a portion of the signaling domain of CD3ζ, (ii) all or a portion of the signaling domain of 4-1 BB, (iii) all or a portion of the signaling domain of CD28, (iv) or all or a portion of the signaling domain of CD3ζ, 4-1BB, and CD28.

Intracellular components may also include one or more of a protein of a Wnt signaling pathway (e.g., LRP, Ryk, or ROR2), NOTCH signaling pathway (e.g., NOTCH1, NOTCH2, NOTCH3, or NOTCH4), Hedgehog signaling pathway (e.g., PTCH or SMO), receptor tyrosine kinases (RTKs) (e.g., epidermal growth factor (EGF) receptor family, fibroblast growth factor (FGF) receptor family, hepatocyte growth factor (HGF) receptor family, insulin receptor (IR) family, platelet-derived growth factor (PDGF) receptor family, vascular endothelial growth factor (VEGF) receptor family, tropomycin receptor kinase (Trk) receptor family, ephrin (Eph) receptor family, AXL receptor family, leukocyte tyrosine kinase (LTK) receptor family, tyrosine kinase with immunoglobulin-like and EGF-like domains 1 (TIE) receptor family, receptor tyrosine kinase-like orphan (ROR) receptor family, discoidin domain (DDR) receptor family, rearranged during transfection (RET) receptor family, tyrosine-protein kinase-like (PTK7) receptor family, related to receptor tyrosine kinase (RYK) receptor family, or muscle specific kinase (MuSK) receptor family); G-protein-coupled receptors, GPCRs (Frizzled or Smoothened); serine/threonine kinase receptors (BMPR or TGFR); or cytokine receptors (IL1R, IL2R, IL7R, or IL15R).

(III-B-v) Linkers. As used herein, a linker can include any portion of a CAR molecule that serves to connect two other subcomponents of the molecule. Some linkers serve no purpose other than to link components while many linkers serve an additional purpose. Linkers can, for example, link VL and VH of antibody derived binding domains of scFvs and serve as junction amino acids between subcomponent portions of a CAR.

Linkers can be flexible, rigid, or semi-rigid, depending on the desired function of the linker. Linkers can include junction amino acids. For example, in particular embodiments, linkers provide flexibility and room for conformational movement between different components of CAR. Commonly used flexible linkers include Gly-Ser linkers. In particular embodiments, the linker sequence includes sets of glycine and serine repeats such as from one to ten repeats of $(Gly_xSer_y)_n$, wherein x and y are independently an integer from 0 to 10 provided that x and y are not both 0 and wherein n is an integer of 1, 2, 3, 4, 5, 6, 7, 8, 9 or 10). Particular examples include (Gly4Ser)n (SEQ ID NO: 1), (Gly3Ser)n (Gly4Ser)n (SEQ ID NO: 2), (Gly3Ser)n(Gly2Ser)n (SEQ ID NO: 3), or (Gly3Ser)n(Gly4Ser)1 (SEQ ID NO: 4). In particular embodiments, the linker is $(Gly4Ser)_4$ (SEQ ID NO: 7), $(Gly4Ser)_3$ (SEQ ID NO: 8), $(Gly4Ser)_2$ (SEQ ID NO: 106), $(Gly4Ser)_1$ (SEQ ID NO: 5), $(Gly3Ser)_2$ (SEQ ID NO: 107), $(Gly3Ser)_1$ (SEQ ID NO: 6), $(Gly2Ser)_2$ (SEQ ID NO: 108) or $(Gly2Ser)_1$, GGSGGGSGGSG (SEQ ID NO: 109), GGSGGGSGSG (SEQ ID NO: 110), or GGSGGGSG (SEQ ID NO: 111).

In particular embodiments, a linker region is (GGGGS)n (SEQ ID NO: 1) wherein n is an integer including, 1, 2, 3, 4, 5, 6, 7, 8, 9, or more. In particular embodiments, the spacer region is (EAAAK)n (SEQ ID NO: 112) wherein n is an integer including 1, 2, 3, 4, 5, 6, 7, 8, 9, or more.

In some situations, flexible linkers may be incapable of maintaining a distance or positioning of CAR needed for a particular use. In these instances, rigid or semi-rigid linkers may be useful. Examples of rigid or semi-rigid linkers include proline-rich linkers. In particular embodiments, a proline-rich linker is a peptide sequence having more proline residues than would be expected based on chance alone. In particular embodiments, a proline-rich linker is one having at least 30%, at least 35%, at least 36%, at least 39%, at least 40%, at least 48%, at least 50%, or at least 51% proline residues. Particular examples of proline-rich linkers include fragments of proline-rich salivary proteins (PRPs).

Linkers can be susceptible to cleavage (cleavable linker), such as, acid-induced cleavage, photo-induced cleavage, peptidase-induced cleavage, esterase-induced cleavage, and disulfide bond cleavage. Alternatively, linkers can be substantially resistant to cleavage (e.g., stable linker or non-cleavable linker). In some aspects, the linker is a procharged linker, a hydrophilic linker, or a dicarboxylic acid-based linker.

Junction amino acids can be a linker which can be used to connect sequences when the distance provided by a spacer region is not needed and/or wanted. For example, junction amino acids can be short amino acid sequences that can be used to connect co-stimulatory intracellular signaling components. In particular embodiments, junction amino acids are 9 amino acids or less (e.g., 2, 3, 4, 5, 6, 7, 8, or 9 amino acids). In particular embodiments, a glycine-serine doublet can be used as a suitable junction amino acid linker. In particular embodiments, a single amino acid, e.g., an alanine, a glycine, can be used as a suitable junction amino acid.

(III-B-vi) Control Features Including Tag Cassettes, Transduction Markers, and/or Suicide Switches. In particular embodiments, CAR constructs can include one or more tag cassettes and/or transduction markers. Tag cassettes and transduction markers can be used to activate, promote proliferation of, detect, enrich for, isolate, track, deplete and/or eliminate genetically modified cells in vitro, in vivo and/or ex vivo. "Tag cassette" refers to a unique synthetic peptide sequence affixed to, fused to, or that is part of a CAR, to which a cognate binding molecule (e.g., ligand, antibody, or other binding partner) is capable of specifically binding where the binding property can be used to activate, promote proliferation of, detect, enrich for, isolate, track, deplete and/or eliminate the tagged protein and/or cells expressing the tagged protein. Transduction markers can serve the same purposes but are derived from naturally occurring molecules and are often expressed using a skipping element that separates the transduction marker from the rest of the CAR molecule.

Tag cassettes that bind cognate binding molecules include, for example, His tag (HHHHHH; SEQ ID NO: 113), Flag tag (DYKDDDDK; SEQ ID NO: 114), Xpress tag (DLYDDDDK; SEQ ID NO: 115), Avi tag (GLNDIFEAQKIEWHE; SEQ ID NO: 116), Calmodulin tag (KRRWKKNFIAVSAANRFKKISSSGAL; SEQ ID NO: 117), Polyglutamate tag, HA tag (YPYDVPDYA; SEQ ID NO: 118), Myc tag (EQKLISEEDL; SEQ ID NO: 119), Strep tag (which refers the original STREP® tag (WRHPQFGG; SEQ ID NO: 120), STREP® tag II (WSHPQFEK; SEQ ID NO: 121 (IBA Institut fur Bioanalytik, Germany); see, e.g., U.S. Pat. No. 7,981,632), Softag 1 (SLAELLNAGLGGS; SEQ ID NO: 122), Softag 3 (TQDPSRVG; SEQ ID NO: 123), and V5 tag (GKPIPNPLLGLDST; SEQ ID NO: 124).

Conjugate binding molecules that specifically bind tag cassette sequences disclosed herein are commercially available. For example, His tag antibodies are commercially available from suppliers including Life Technologies, Pierce Antibodies, and GenScript. Flag tag antibodies are commercially available from suppliers including Pierce Antibodies, GenScript, and Sigma-Aldrich. Xpress tag antibodies are commercially available from suppliers including Pierce Antibodies, Life Technologies and GenScript. Avi tag antibodies are commercially available from suppliers including Pierce Antibodies, IsBio, and Genecopoeia. Calmodulin tag antibodies are commercially available from suppliers including Santa Cruz Biotechnology, Abcam, and Pierce Antibodies. HA tag antibodies are commercially available from suppliers including Pierce Antibodies, Cell Signal and Abcam. Myc tag antibodies are commercially available from suppliers including Santa Cruz Biotechnology, Abcam, and Cell Signal. Strep tag antibodies are commercially available from suppliers including Abcam, Iba, and Qiagen.

Transduction markers may be selected from at least one of a truncated CD19 (tCD19; see Budde et al., Blood 122: 1660, 2013); a truncated human EGFR (tEGFR; see Wang et al., Blood 118: 1255, 2011); an extracellular domain of human CD34; and/or RQR8 which combines target epitopes from CD34 (see Fehse et al, Mol. Therapy 1(5 Pt 1); 448-456, 2000) and CD20 antigens (see Philip et al, Blood 124: 1277-1278).

In particular embodiments, a polynucleotide encoding an iCaspase9 construct (iCasp9) may be inserted into a CAR construct as a suicide switch.

Control features may be present in multiple copies in a CAR or can be expressed as distinct molecules with the use of a skipping element (SEQ ID NOs: 149-152). For example, a CAR can have one, two, three, four or five tag cassettes and/or one, two, three, four, or five transduction markers could also be expressed. For example, embodiments can include a CAR construct having two Myc tag cassettes, or a His tag and an HA tag cassette, or a HA tag and a Softag 1 tag cassette, or a Myc tag and a SBP tag cassette. Exemplary transduction markers and cognate pairs are described in U.S. Ser. No. 13/463,247.

One advantage of including at least one control feature in a CAR is that cells expressing CAR administered to a subject can be increased or depleted using the cognate binding molecule to a tag cassette. In certain embodiments, the present disclosure provides a method for depleting a modified cell expressing a CAR by using an antibody specific for the tag cassette, using a cognate binding molecule specific for the control feature, or by using a second modified cell expressing a CAR and having specificity for the control feature. Elimination of modified cells may be accomplished using depletion agents specific for a control feature. For example, if tEGFR is used, then an anti-tEGFR binding domain (e.g., antibody, scFv) fused to or conjugated to a cell-toxic reagent (such as a toxin, radiometal) may be used, or an anti-tEGFR/anti-CD3 bispecific scFv, or an anti-tEGFR CAR T cell may be used.

In certain embodiments, modified cells expressing a chimeric molecule may be detected or tracked in vivo by using antibodies that bind with specificity to a control feature (e.g., anti-Tag antibodies), or by other cognate binding molecules that specifically bind the control feature, which binding partners for the control feature are conjugated to a fluorescent dye, radio-tracer, iron-oxide nanoparticle or other imaging agent known in the art for detection by X-ray, CT-scan, MRI-scan, PET-scan, ultrasound, flow-cytometry, near infrared imaging systems, or other imaging modalities (see, e.g., Yu, et al., *Theranostics* 2:3, 2012).

Thus, modified cells expressing at least one control feature with a CAR can be, e.g., more readily identified, isolated, sorted, induced to proliferate, tracked, and/or eliminated as compared to a modified cell without a tag cassette.

(III-C) TNFα Signal Potentiators. As indicated previously, TNFRS family members are provided in FIG. 6 including whether a compound should activate or inhibit the activity of the family member to qualify as a TNFα signal potentiator. In particular embodiments, cells are genetically modified to express one or more TNFRSF members that potentiate TNFα. In particular embodiments, cells are genetically modified to inhibit or inactive TNFRSF members that inhibit TNFα. The cell genetically modified to express a TNFα signal potentiator protein can be the same cell genetically modified to express a CAR or can be a different cell.

Particular examples of proteins that can be expressed as TNFα signal potentiators include TWEAK (tumor necrosis factor-like weak inducer of apoptosis); TRAIL (Tumor necrosis factor-related apoptosis-inducing ligand); and LIGHT (homologous to lymphotoxin, exhibits inducible expression and competes with HSV glycoprotein D for binding to herpesvirus entry mediator, a receptor expressed on T lymphocytes).

TWEAK, also known as TNFRSF12A, was initially described as a member of the tumor necrosis factor (TNF) superfamily in 1997. TWEAK is a cell surface-associated type II transmembrane protein, but a smaller, biologically active form can also be shed into the extracellular milieu. There is one receptor currently known to bind TWEAK with physiological affinity, and it is a type I transmembrane protein that is referred to in the literature as either TWEAK receptor (TweakR) or fibroblast growth factor-inducible 14 (Fn14). TweakR/Fn14 is the smallest member of the TNF receptor (TNFR) superfamily described to date, and it appears to signal via recruitment of several different TNFR-associated factors. TWEAK has multiple biological activities, including stimulation of cell growth and angiogenesis, induction of inflammatory cytokines, and under some experimental conditions, stimulation of apoptosis. (PMID: 12787562). For additional information regarding TWEAK, see WO2011084714A2.

TRAIL/Apo2L is a member of the tumor necrosis factor (TNF) family of ligands capable of initiating apoptosis through engagement of its death receptors. TRAIL selectively induces apoptosis of a variety of tumor cells and transformed cells, but not most normal cells, and therefore has garnered intense interest as a promising agent for cancer therapy. TRAIL is expressed on different cells of the immune system and plays a role in both T-cell- and natural killer cell-mediated tumor surveillance and suppression of suppressing tumor metastasis.

LIGHT, also known as tumor necrosis factor superfamily member 14 (TNFSF14), is a secreted protein of the TNF superfamily. It is recognized by herpesvirus entry mediator (HVEM), as well as decoy receptor 3. For more information regarding LIGHT, see EP3105317B1 and US20050163747.

(IV) Cell Activating Culture Conditions. Cell populations can be incubated in a culture-initiating composition to expand genetically modified cell populations. The incubation can be carried out in a culture vessel, such as a bag, cell culture plate, flask, chamber, chromatography column, cross-linked gel, cross-linked polymer, column, culture dish, hollow fiber, microtiter plate, silica-coated glass plate, tube, tubing set, well, vial, or other container for culture or cultivating cells.

Culture conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some aspects, incubation is carried out in accordance with techniques such as those described in U.S. Pat. No. 6,040,177, Klebanoff et al. (2012) J Immunother. 35(9): 651-660, Terakura et al. (2012) Blood. 1:72-82, and/or Wang et al. (2012) J Immunother. 35(9):689-701.

Exemplary culture media for culturing T cells include (i) RPMI supplemented with non-essential amino acids, sodium pyruvate, and penicillin/streptomycin; (ii) RPMI with HEPES, 5-15% human serum, 1-3% L-Glutamine, 0.5-1.5% penicillin/streptomycin, and 0.25×10-4-0.75×10-4 M β-MercaptoEthanol; (iii) RPMI-1640 supplemented with 10% fetal bovine serum (FBS), 2 mM L-glutamine, 10 mM HEPES, 100 U/ml penicillin and 100 m/mL streptomycin; (iv) DMEM medium supplemented with 10% FBS, 2 mM L-glutamine, 10 mM HEPES, 100 U/ml penicillin and 100 m/mL streptomycin; and (v) X-Vivo 15 medium (Lonza, Walkersville, MD) supplemented with 5% human AB serum (Gemcell, West Sacramento, CA), 1% HEPES (Gibco, Grand Island, NY), 1% Pen-Strep (Gibco), 1% GlutaMax (Gibco), and 2% N-acetyl cysteine (Sigma-Aldrich, St. Louis, MO). T cell culture media are also commercially available from Hyclone (Logan, UT). Additional T cell activating components that can be added to such culture media are described in more detail below.

In some embodiments, the T cells are expanded by adding to the culture-initiating composition feeder cells, such as non-dividing peripheral blood mononuclear cells (PBMC), (e.g., such that the resulting population of cells contains at least 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can include gamma-irradiated PBMC feeder cells. In some embodiments, the PBMC are irradiated with gamma rays in the range of 3000 to 3600 rads to prevent cell division. In some aspects, the feeder cells are added to culture medium prior to the addition of the populations of T cells.

Optionally, the incubation may further include adding non-dividing EBV-transformed lymphoblastoid cells (LCL) as feeder cells. LCL can be irradiated with gamma rays in the range of 6000 to 10,000 rads. The LCL feeder cells in some aspects is provided in any suitable amount, such as a ratio of LCL feeder cells to initial T lymphocytes of at least 10:1.

In some embodiments, the stimulating conditions include temperature suitable for the growth of human T lymphocytes, for example, at least 25° C., at least 30° C., or 37° C.

The activating culture conditions for T cells include conditions whereby T cells of the culture-initiating composition proliferate or expand. T cell activating conditions can include one or more cytokines, for example, interleukin (IL)-2, IL-7, IL-15 and/or IL-21. IL-2 can be included at a range of 1-100 ng/μl (e.g., 40, 50, or 60 ng/μl). IL-7, IL-15, and/or IL-21 can be individually included at a range of 0.1-50 ng/μl (e.g., 5, 10, or 15 ng/μl). Particular embodiments utilize IL-2 at 25 and 50 IU/μl. Particular embodiments utilize IL-7, IL-15 and IL-21 individually included at 10 ng/μl.

In particular embodiments, T cell activating culture condition conditions can include T cell stimulating epitopes. T cell stimulating epitopes include CD3, CD27, CD2, CD4, CD5, CD7, CD8, CD28, CD30, CD40, CD56, CD83, CD90, CD95, 4-1BB (CD 137), B7-H3, CTLA-4, Frizzled-1 (FZD1), FZD2, FZD3, FZD4, FZD5, FZD6, FZD7, FZD8, FZD9, FZD10, HVEM, ICOS, IL-1R, LAT, LFA-1, LIGHT, MHCI, MHCII, NKG2D, OX40, ROR2 and RTK.

CD3 is a primary signal transduction element of T cell receptors. As indicated previously, CD3 is expressed on all mature T cells. In particular embodiments, the CD3 stimulating molecule (i.e., CD3 binding domain) can be derived from the OKT3 antibody (see U.S. Pat. Nos. 5,929,212; 4,361,549; ATCC® CRL-8001™; and Arakawa et al., J. Biochem. 120, 657-662 (1996)), the 20G6-F3 antibody, the 4B4-D7 antibody, the 4E7-C9, or the 18F5-H10 antibody.

In particular embodiments, CD3 stimulating molecules can be included within culture media at a concentration of at least 0.25 or 0.5 ng/ml or at a concentration of 2.5-10 μg/ml. Particular embodiments utilize a CD3 stimulating molecule (e.g., OKT3) at 5 μg/ml.

In particular embodiments, activating molecules associated with avi-tags can be biotinylated and bound to streptavidin beads. This approach can be used to create, for example, a removable T cell epitope stimulating activation system.

An exemplary binding domain for CD28 can include or be derived from TGN1412, CD80, CD86 or the 9D7 antibody. Additional antibodies that bind CD28 include 9.3, KOLT-2, 15E8, 248.23.2, EX5.3D10, and CD28.3 (deposited as a synthetic single chain Fv construct under GenBank Accession No. AF451974.1; see also Vanhove et al., BLOOD, 15 Jul. 2003, Vol. 102, No. 2, pages 564-570). Further, 1YJD provides a crystal structure of human CD28 in complex with the Fab fragment of a mitogenic antibody (5.11A1). In particular embodiments, antibodies that do not compete with 9D7 are selected.

4-1BB binding domains can be derived from LOB12, IgG2a, LOB12.3, or IgG1 as described in Taraban et al. Eur J Immunol. 2002 December; 32(12):3617-27. In particular embodiments a 4-1BB binding domain is derived from a monoclonal antibody described in U.S. Pat. No. 9,382,328. Additional 4-1BB binding domains are described in U.S. Pat. Nos. 6,569,997, 6,303,121, and Mittler et al. Immunol Res. 2004; 29(1-3):197-208.

OX40 (CD134) and/or ICOS activation may also be used. OX40 binding domains are described in US20100196359, US 20150307617, WO 2015/153513, WO2013/038191 and Melero et al. Clin Cancer Res. 2013 Mar. 1; 19(5):1044-53. Exemplary binding domains that can bind and activate ICOS are described in e.g., US20080279851 and Deng et al. Hybrid Hybridomics. 2004 June; 23(3):176-82.

When in soluble form, T-cell activating agents can be coupled with another molecule, such as polyethylene glycol (PEG) molecule. Any suitable PEG molecule can be used. Typically, PEG molecules up to a molecular weight of 1000 Da are soluble in water or culture media. In some cases, such PEG based reagent can be prepared using commercially available activated PEG molecules (for example, PEG-NHS derivatives available from NOF North America Corporation, Irvine, Calif., USA, or activated PEG derivatives available from Creative PEGWorks, Chapel Hills, N.C., USA).

In particular embodiments, cell stimulating agents are immobilized on a solid phase within the culture media. In particular embodiments, the solid phase is a surface of the culture vessel (e.g., bag, cell culture plate, chamber, chromatography column, cross-linked gel, cross-linked polymer, column, culture dish, hollow fiber, microtiter plate, silica-coated glass plate, tube, tubing set, well, vial, other structure or container for culture or cultivation of cells).

In particular embodiments, a solid phase can be added to a culture media. Such solid phases can include, for example, beads, hollow fibers, resins, membranes, and polymers.

Exemplary beads include magnetic beads, polymeric beads, and resin beads (e.g., Strep-Tactin® Sepharose, Strep-Tactin® Superflow, and Strep-Tactin® MacroPrep IBA GmbH, Gottingen)). Anti-CD3/anti-CD28 beads are commercially available reagents for T cell expansion (Invitrogen). These beads are uniform, 4.5 μm superparamagnetic, sterile, non-pyrogenic polystyrene beads coated with a mixture of affinity purified monoclonal antibodies against the CD3 and CD28 cell surface molecules on human T cells. Hollow fibers are available from TerumoBCT Inc. (Lakewood, Colo., USA). Resins include metal affinity chromatography (IMAC) resins (e.g., TALON® resins (Westburg, Leusden)). Membranes include paper as well as the membrane substrate of a chromatography matrix (e.g., a nitrocellulose membrane or a polyvinylidene difluoride (PVDF) membrane).

Exemplary polymers include polysaccharides, such as polysaccharide matrices. Such matrices include agarose gels (e.g., Superflow™ agarose or a Sepharose® material such as Superflow™ Sepharose® that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as Sephadex® or Superdex®, both available from GE Healthcare.

Synthetic polymers that may be used include polyacrylamide, polymethacrylate, a co-polymer of polysaccharide and agarose (e.g. a polyacrylamide/agarose composite) or a polysaccharide and N,N'-methylenebisacrylamide. An example of a copolymer of a dextran and N,N'-methylenebisacrylamide is the Sephacryl® (Pharmacia Fine Chemicals, Inc., Piscataway, NJ) series of materials.

Particular embodiments may utilize silica particles coupled to a synthetic or to a natural polymer, such as polysaccharide grafted silica, polyvinylpyrrolidone grafted silica, polyethylene oxide grafted silica, poly(2-hydroxyethylaspartamide) silica and poly(N-isopropylacrylamide) grafted silica.

Cell activating agents can be immobilized to solid phases through covalent bonds or can be reversibly immobilized through non-covalent attachments.

In particular embodiments, a T-cell activating culture media includes a FACS-sorted T cell population cultured within RPMI with HEPES, 5-15% human serum, 1-3% L-Glutamine, 0.5-1.5% Pen/strep, 0.25x10-4-0.75x$10^{-4}$ M β-MercaptoEthanol, with IL-7, IL-15 and IL-21 individually included at 5-15 (e.g., 10) ng/μl. The culture is carried out on a flat-bottom well plate with 0.1-0.5x10e6 plated cells/well. On Day 3 post activation cells are transferred to a TC-treated plate.

In particular embodiments, a T-cell activating culture media includes a FACS-sorted CD8+ T population cultured within RPMI with HEPES, 10% human serum, 2% L-Glutamine, 1% Pen/strep, 0.5x$10^{-4}$ M p-MercaptoEthanol, with IL-7, IL-15 and IL-21 individually included at 5-15 (e.g., 10) ng/μl. The culture is carried out on a flat-bottom non-tissue culture (TC)-treated 96/48-well plate with 0.1-0.5x 10e6 plated cells/well. On Day 3 post activation cells are transferred to TC-treated plate.

Culture conditions for HSC/HSP can include expansion with a Notch agonist (see, e.g., U.S. Pat. Nos. 7,399,633; 5,780,300; 5,648,464; 5,849,869; and 5,856,441 and growth factors present in the culture condition as follows: 25-300 ng/ml SCF, 25-300 ng/ml Flt-3L, 25-100 ng/ml TPO, 25-100 ng/ml IL-6 and 10 ng/ml IL-3. In more specific embodiments, 50, 100, or 200 ng/ml SCF; 50, 100, or 200 ng/ml of Flt-3L; 50 or 100 ng/ml TPO; 50 or 100 ng/ml IL-6; and 10 ng/ml IL-3 can be used.

(V) Ex Vivo Manufactured Cell Formulations. In particular embodiments, genetically-modified cells can be harvested from a culture medium and washed and concentrated into a carrier in a therapeutically-effective amount. Exemplary carriers include saline, buffered saline, physiological saline, water, Hanks' solution, Ringer's solution, Nonnosol-R (Abbott Labs), PLASMA-LYTE A® (Baxter Laboratories, Inc., Morton Grove, IL), glycerol, ethanol, and combinations thereof.

In particular embodiments, carriers can be supplemented with human serum albumin (HSA) or other human serum components or fetal bovine serum. In particular embodiments, a carrier for infusion includes buffered saline with 5% HAS or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, compositions or formulations can include a local anesthetic such as lidocaine to ease pain at a site of injection.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Therapeutically effective amounts of cells within compositions or formulations can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$.

In compositions and formulations disclosed herein, cells are generally in a volume of a liter or less, 500 mls or less, 250 mls or less or 100 mls or less. Hence the density of administered cells is typically greater than $10^4$ cells/ml, $10^7$ cells/ml or $10^8$ cells/ml.

As indicated, compositions include at least one genetically-modified cell type (e.g., modified T cells, NK cells, or stem cells). Formulations can include different types of genetically-modified cells (e.g., T cells, NK cells, and/or stem cells in combination).

Different types of genetically-modified cells or cell subsets (e.g., modified T cells, NK cells, and/or stem cells) can be provided in different ratios e.g., a 1:1:1 ratio, 2:1:1 ratio, 1:2:1 ratio, 1:1:2 ratio, 5:1:1 ratio, 1:5:1 ratio, 1:1:5 ratio, 10:1:1 ratio, 1:10:1 ratio, 1:1:10 ratio, 2:2:1 ratio, 1:2:2 ratio, 2:1:2 ratio, 5:5:1 ratio, 1:5:5 ratio, 5:1:5 ratio, 10:10:1 ratio, 1:10:10 ratio, 10:1:10 ratio, etc. These ratios can also apply to numbers of cells expressing the same or different CAR components. If only two of the cell types are combined or only 2 combinations of expressed CAR components are included within a formulation, the ratio can include any 2-number combination that can be created from the 3 number combinations provided above. In embodiments, the combined cell populations are tested for efficacy and/or cell proliferation in vitro, in vivo and/or ex vivo, and the ratio of cells that provides for efficacy and/or proliferation of cells is selected. Particular embodiments include a 1:1 ratio of CD4 T cells and CD8 T cells.

The cell-based compositions disclosed herein can be prepared for administration by, e.g., injection, infusion, perfusion, or lavage. The compositions and formulations can further be formulated for bone marrow, intravenous, intradermal, intraarterial, intranodal, intralymphatic, intraperitoneal, intralesional, intratumoral, intravesicular, and/or subcutaneous injection.

(VI) TNFα Signal Potentiators—Small Molecules and Proteins. Compounds used within the current disclosure that can serve as small molecule TNFα signal potentiators include BV-6, CUDC-427, GDC-0152, LCL161, Rocaglamide, Sirolimus, Emricasan, Birinapant, ASTX660, AZD5582, BI 891065, DEBIO 1143, APG-1387, HGS1029, AEG35156, Escin, and KILLERTRAIL™.

In particular embodiments, the TNFα signal potentiator is selected from Rocaglamide, Sirolimus, and Emricasan:

Rocaglamide (1R,2R,3S,3aR,8bS)-1,8b-dihydroxy-6,8-dimethoxy-3a-(4-methoxyphenyl)-N,N-dimethyl-3-phenyl-2,3-dihydro-1H-cyclopenta[b][1]benzofuran-2-carboxamide,

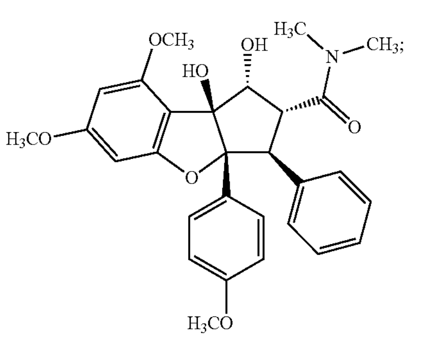 [SMILES: COc1ccc([C@@]23Oc4cc(OC)cc(OC)c4[C@]2(O)[C@H](O)[C@H](C(=O)N(C)C)[C@H]3c2ccccc2)cc1]

Sirolimus (1R,9S,12S,15R,16E,18R,19R,21R,23S,24E,26E,28E,30S,32S,35R)-1,18-dihydroxy-12-[(2R)-1-[(1S,3R,4R)-4-hydroxy-3-methoxycyclohexyl]propan-2-yl]-19,30-dimethoxy-15,17,21,23,29,35-hexamethyl-11,36-dioxa-4-azatricyclo[30.3.1.04,9]hexatriaconta-16,24,26,28-tetraene-2,3,10,14,20-pentone,

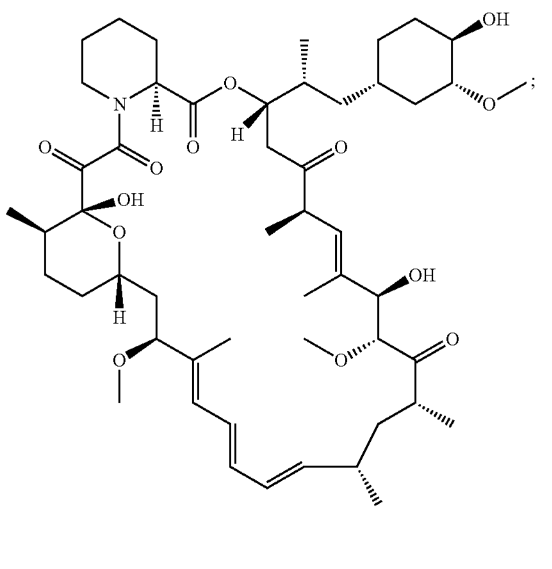

and

Emricasan (3S)-3-[[(2S)-2-[[2-(2-tert-butylanilino)-2-oxoacetyl]amino]propanoyl]amino]-4-oxo-5-(2,3,5,6-tetrafluorophenoxy)pentanoic acid,

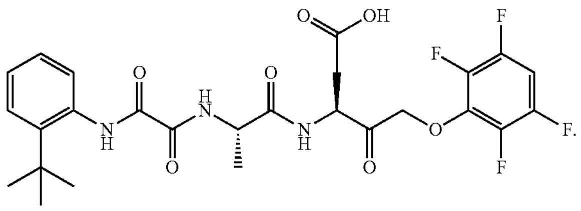 [SMILES: C[C@H](NC(=O)C(=O)Nc1ccccc1C(C)(C)C)C(=O)N[C@@H](CC(=O)O)C(=O)COc1c(F)c(F)cc(F)c1F]

In particular embodiments, compounds which amplify TNFα are SMAC-mimetics including: Birinapant (2S)—N-[(2S)-1-[(2R,4S)-2-[[6-fluoro-2-[6-fluoro-3-[[(2R,4S)-4-hydroxy-1-[(2S)-2-[[(2S)-2-(methylamino)propanoyl]amino]butanoyl]pyrrolidin-2-yl]methyl]-1H-indol-2-yl]-1H-indol-3-yl]methyl]-4-hydroxypyrrolidin-1-yl]-1-oxobutan-2-yl]-2-(methylamino)propenamide,

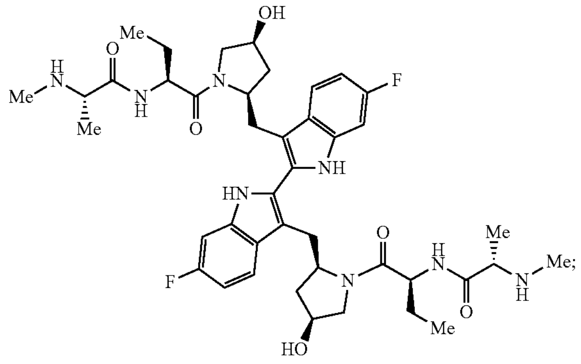 [SMILES: CC[C@H](NC(=O)[C@H](C)NC)C(=O)N1C[C@@H](O)C[C@H]1Cc1c(-c2[nH]c3cc(F)ccc3c2C[C@@H]2C[C@H](O)CN2C(=O)[C@H](CC)NC(=O)[C@H](C)NC)[nH]c2cc(F)ccc12]

LCL161 (2S)—N-[(1S)-1-cyclohexyl-2-[(2S)-2-[4-(4-fluorobenzoyl)-1,3-thiazol-2-yl]pyrrolidin-1-yl]-2-oxoethyl]-2-(methylamino)propenamide,

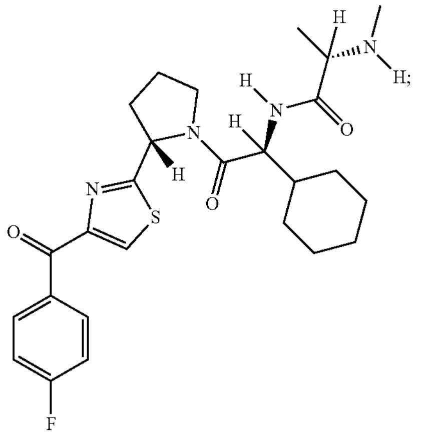

ASTX660 1-[6-[(4-fluorophenyl)methyl]-5-(hydroxymethyl)-3,3-dimethyl-2H-pyrrolo[3,2-b]pyridin-1-yl]-2-[(2R,5R)-5-methyl-2-[[(3R)-3-methylmorpholin-4-yl]methyl]piperazin-1-yl]ethenone,

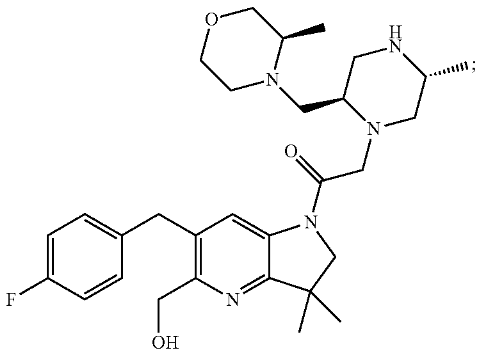 [SMILES: C[C@@H]1CN(CC(=O)N2CC(C)(C)c3nc(CO)c(Cc4ccc(F)cc4)cc32)[C@@H](CN2CCOC[C@H]2C)CN1]

;

BI 891065; CUDC-427 (2S)-1-[(2S)-2-cyclohexyl-2-[[(2S)-2-(methylamino)propanoyl]amino]acetyl]-N-[2-(1,3-oxazol-2-yl)-4-phenyl-1,3-thiazol-5-yl]pyrrolidine-2-carboxamide,

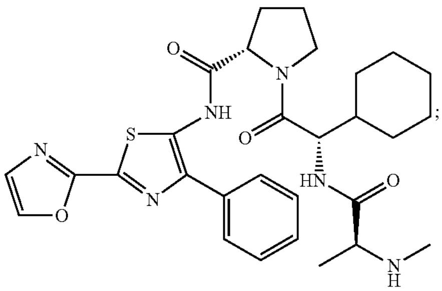 [SMILES: CN[C@@H](C)C(=O)N[C@H](C(=O)N1CCC[C@H]1C(=O)Nc1sc(-c2ncco2)nc1-c1ccccc1)C1CCCCC1]

;

DEBIO 1143 (5S,8S,10aR)—N-benzhydryl-5-[[(2S)-2-(methylamino)propanoyl]amino]-3-(3-methylbutanoyl)-6-oxo-1,2,4,5,8,9,10,10a-octahydropyrrolo[1,2-a][1,5]diazocine-8-carboxamide,

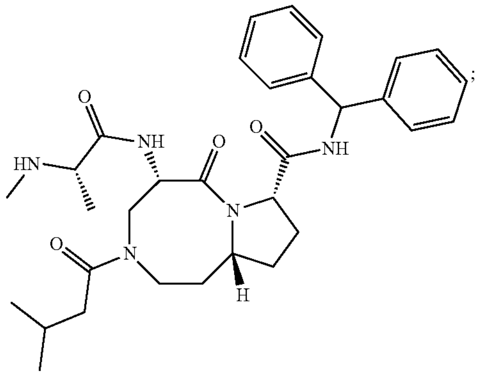 [SMILES: CN[C@@H](C)C(=O)N[C@H]1CN(C(=O)CC(C)C)CC[C@H]2CC[C@@H](C(=O)NC(c3ccccc3)c3ccccc3)N2C1=O]

;

APG-1387 (5S,8S,10aR)-3-[3-[[(5S,8S,10aR)-8-(benzhydrylcarbamoyl)-5-[[(2S)-2-(methylamino) propanoyl]amino]-6-oxo-1,2,4,5,8,9,10,10a-octahydropyrrolo[1,2-a][1,5]diazocin-3-yl]sulfonyl]phenyl]sulfonyl-N-benzhydryl-5-[[(2S)-2-(methylamino)propanoyl]amino]-6-oxo-1,2,4,5,8,9,10,10a-octahydropyrrolo[1,2-a][1,5]diazocine-8-carboxamide,

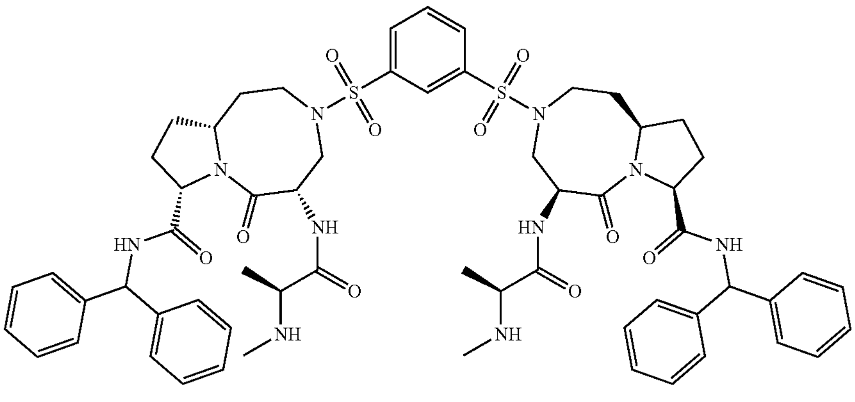

;

HGS1029; AEC35156; AZD5582 (2S)-1-[(2S)-2-cyclohexyl-2-[[(2S)-2-(methylamino)propanoyl]amino]acetyl]-N-[(1S,2R)-2-[6-[[(1S,2R)-1-[[(2S)-1-[(2S)-2-cyclohexyl-2-[[(2S)-2-(methylamino)propanoyl]amino]acetyl]pyrrolidine-2-carbonyl]amino]-2,3-dihydro-1H-inden-2-yl]oxy]hexa-2,4-diynoxy]-2,3-dihydro-1H-inden-1-yl]pyrrolidine-2-carboxamide,

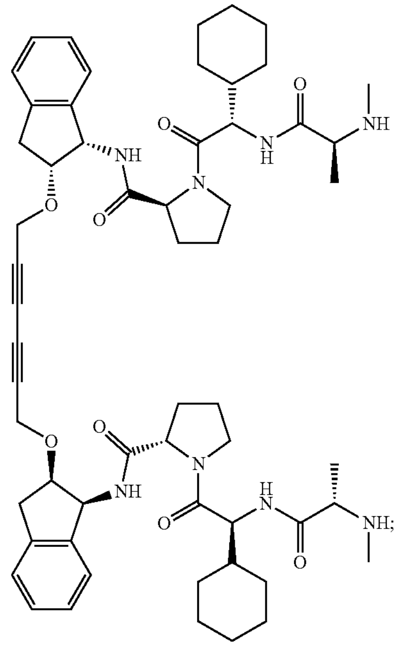 [SMILES: CN[C@@H](C)C(=O)N[C@H](C(=O)N1CCC[C@H]1C(=O)N[C@H]1c2ccccc2C[C@H]1OCC#CC#CCO[C@@H]1Cc2ccccc2[C@@H]1NC(=O)[C@@H]1CCCN1C(=O)[C@@H](NC(=O)[C@H](C)NC)C1CCCCC1)C1CCCCC1]

APG-1387 (5S,8S,10aR)-3-[3-[[(5S 8S,10aR)-8-(benzhydrylcarbamoyl)-5-[[(2S)-2-(methylamino) propanoyl]amino]-6-oxo-1,2,4,5,8,9,10,10a-octahydropyrrolo[1,2-a][1,5]diazocin-3-yl]sulfonyl]phenyl]sulfonyl-N-benzhydryl-5-[[(2S)-2-(methylamino)propanoyl]amino]-6-oxo-1,2,4,5,8,9,10,10a-octahydropyrrolo[1,2-a][1,5]diazocine-8-carboxamide,

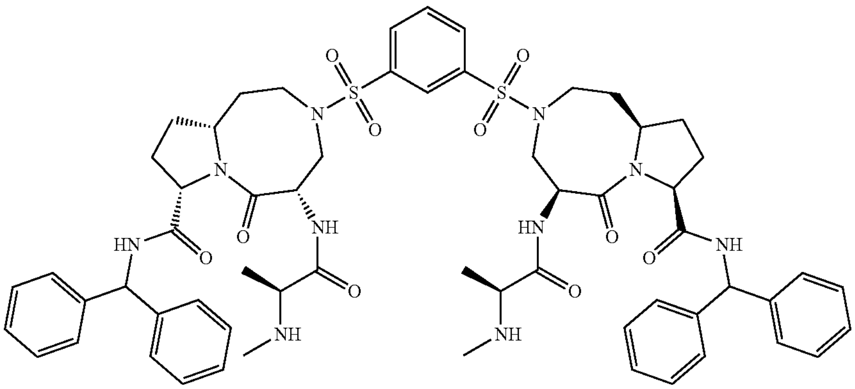

;

GDC-0152 (2S)-1-[(2S)-2-cyclohexyl-2-[[(2S) 2 (methylamino)propanoyl]amino]acetyl]-N-(4-phenylthiadiazol-5-yl)pyrrolidine-2-carboxamide,

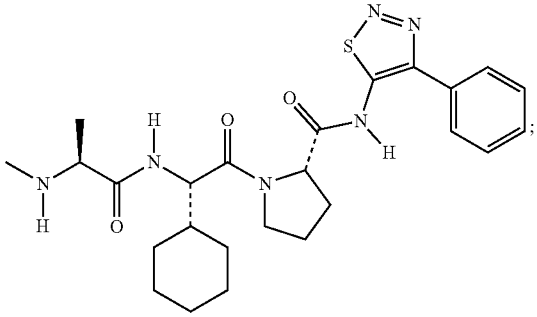 [SMILES: CN[C@@H](C)C(=O)N[C@H](C(=O)N1CCC[C@H]1C(=O)Nc1snnc1-c1ccccc1)C1CCCCC1]

;

WX20120108

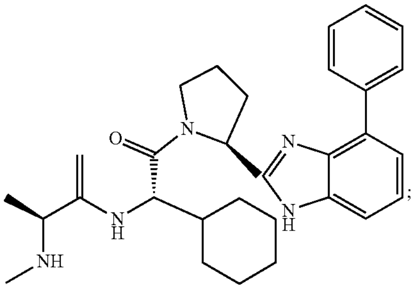

;

SM-122 (3S,6S,10As)—N-benzhydryl-6-[[(2S)-2-(methylamino)propanoyl]amino]-5-oxo-2,3,6,7,8,9,10,10a-octahydro-1H-pyrrolo[1,2-a]azocine-3-carboxamide,
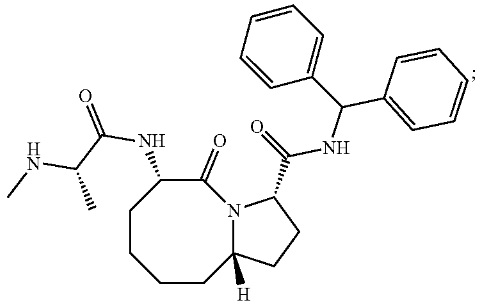 [SMILES: CN[C@@H](C)C(=O)N[C@H]1CCCC[C@H]2CC[C@@H](C(=O)NC(c3ccccc3)c3ccccc3)N2C1=O]
;
SM-164 (3S,6S,10As)—N—[(S)-[1-[4-[4-[4-[4-[(S)-[[(3S,6S,10aS)-6-[[(2S)-2-(methylamino)propanoyl]amino]-5-oxo-2,3,6,7,8,9,10,10a-octahydro-1H-pyrrolo[1,2-a]azocine-3-carbonyl]amino]-phenylmethyl]triazol-1-yl]butyl]phenyl]butyl]triazol-4-yl]-phenylmethyl]-6-[[(2S)-2-(methylamino) propanoyl]amino]-5-oxo-2,3,6,7,8,9,10,10a-octahydro-1H-pyrrolo[1,2-a]azocine-3-carboxamide,
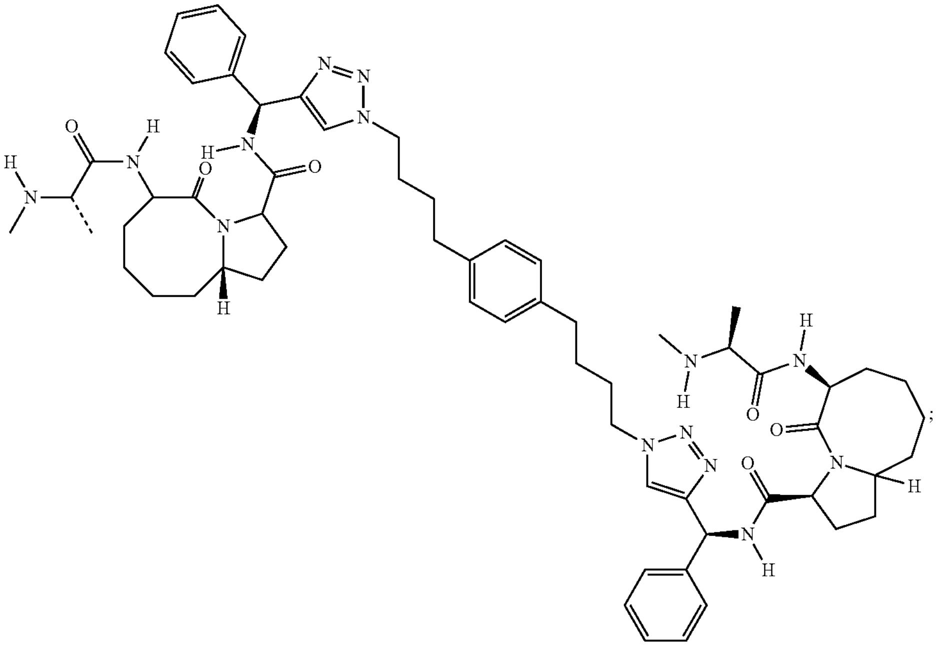 [SMILES: CN[C@@H](C)C(=O)NC1CCCC[C@H]2CCC(C(=O)N[C@@H](c3ccccc3)c3cn(CCCCc4ccc(CCCCn5cc([C@@H](NC(=O)[C@@H]6CCC7CCCC[C@H](NC(=O)[C@H](C)NC)C(=O)N76)c6ccccc6)nn5)cc4)nn3)N2C1=O]
;

BV-6 (S,S,2S,2'S)—N,N'-((2S,2'S)-(hexane-1,6-diylbis(azanediyl))bis(3-oxo-1,1-diphenylpropane-3,2-diyl))bis(1-((S)-2-cyclohexyl-2-((S)-2-(methylamino)propanamido)acetyl)pyrrolidine-2-carboxamide),

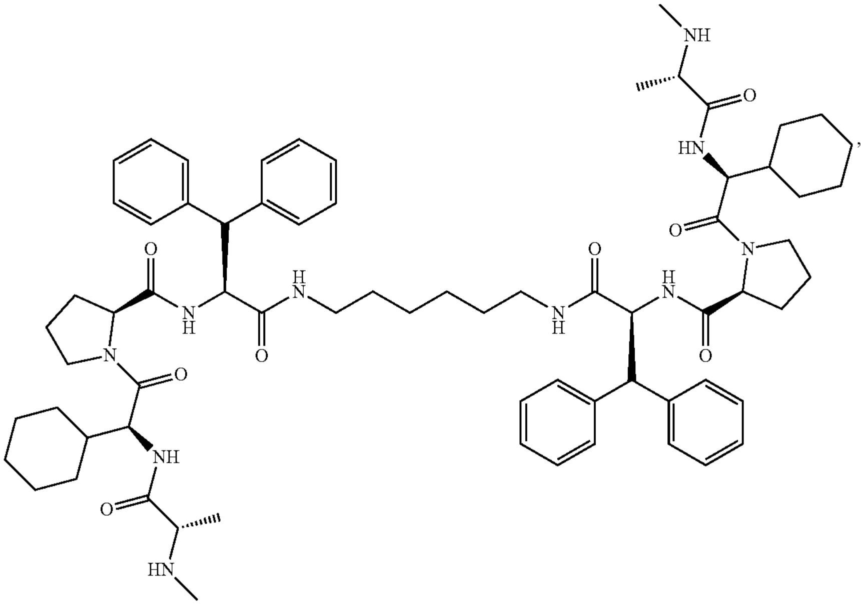 [SMILES: CN[C@@H](C)C(=O)N[C@H](C(=O)N1CCC[C@H]1C(=O)N[C@H](C(=O)NCCCCCCNC(=O)[C@@H](NC(=O)[C@@H]1CCCN1C(=O)[C@@H](NC(=O)[C@H](C)NC)C1CCCCC1)C(c1ccccc1)c1ccccc1)C(c1ccccc1)c1ccccc1)C1CCCCC1]

AZD5582 ((2S)-1-[(2S)-2-cyclohexyl-2-[[(2S)-2-(methylamino)propanoyl]amino]acetyl]-N-[(1S,2R)-2-[6-[[(1S,2R)-1-[[(2S)-1-[(2S)-2-cyclohexyl-2-[[(2S)-2-(methylamino)propanoyl]amino]acetyl]pyrrolidine-2-carbonyl]amino]-2,3-dihydro-1H-inden-2-yl]oxy]hexa-2,4-diynoxy]-2,3-dihydro-1H-inden-1-yl]pyrrolidine-2-carboxamide)

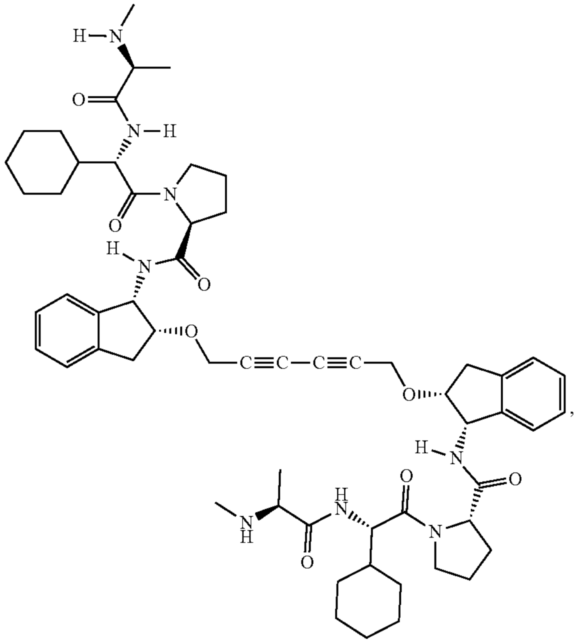 [SMILES: CN[C@@H](C)C(=O)N[C@H](C(=O)N1CCC[C@H]1C(=O)N[C@H]1c2ccccc2C[C@H]1OCC#CC#CCO[C@@H]1Cc2ccccc2[C@@H]1NC(=O)[C@@H]1CCCN1C(=O)[C@@H](NC(=O)[C@H](C)NC)C1CCCCC1)C1CCCCC1]

CUDC-427 ((2S)-1-[(2S)-2-cyclohexyl-2-[[(2S)-2-(methylamino)propanoyl]amino]acetyl]-N-[2-(1,3-oxazol-2-yl)-4-phenyl-1,3-thiazol-5-yl]pyrrolidine-2-carboxamide)

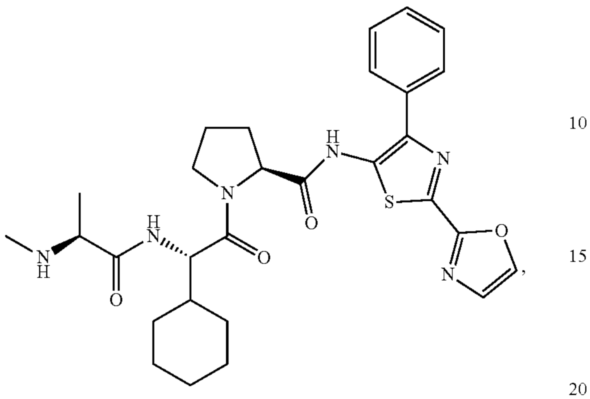

Escin ((2S,3S,4S,5R,6R)-6-[[(3S,4S,4aR,6aR,6bS,8R,8aR,9R,10R,12aS,14aR,14bR)-9-acetyloxy-8-hydroxy-4,8a-bis(hydroxymethyl)-4,6a,6b,11,11,14b-hexamethyl-10-[(Z)-2-methylbut-2-enoyl]oxy-1,2,3,4a,5,6,7,8,9,10,12,12a,14,14a-tetradecahydropicen-3-yl]oxy]-4-hydroxy-3,5-bis[[(2S,3R,4S,5S,6R)-3,4,5-trihydroxy-6-(hydroxymethyl)oxan-2-yl]oxy]oxane-2-carboxylic acid

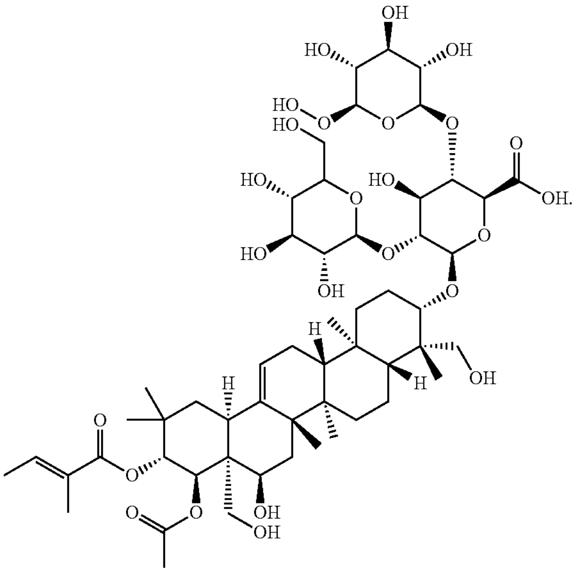 [SMILES: C/C=C(\C)C(=O)O[C@H]1[C@H](OC(C)=O)[C@]2(CO)[C@H](O)C[C@]3(C)C(=CC[C@@H]4[C@@]5(C)CC[C@H](O[C@@H]6O[C@H](C(=O)O)[C@@H](O[C@H]7O[C@@H](OO)[C@H](O)[C@@H](O)[C@@H]7O)[C@H](O)[C@H]6O[C@@H]6OC(CO)[C@@H](O)[C@H](O)[C@H]6O)[C@](C)(CO)[C@@H]5CC[C@]43C)[C@@H]2CC1(C)C]

KILLERTRAIL™ refers to a recombinant protein including the extracellular domain of human TRAIL (aa 95-281) fused at the N-terminus to a His-tag and a linker peptide.

As indicated, SMAC mimetics and potentiators of TNF superfamily ligand-regulated cell death can be used. For more information on additional SMAC-mimetic structures and derivatives with similar functional properties see: US2018155322, US2017037004, US2015158908, U.S. Pat. Nos. 8,986,993, 8,283,372, US2019031766, US2019185511, US2019135794, US2018186882, US2018179183, US2018065959, U.S. Pat. No. 9,783,538, US2019151295, U.S. Pat. Nos. 8,716,236, 8,664,212, 8,278,293, WO2020024932, WO2019122941, WO2019122337, WO2015109391, AU2017223233, WO2017117684, WO2019165215, US20160184383, US20170319592, US2010317593, US2018193470, U.S. Pat. Nos. 8,883,771, 8,980,837, 8,202,902, US20120238766, EP1693059, US20100098770, WO2006116727, WO2018017426, and PMID: 31316176. The current disclosure also includes use of pharmaceutically acceptable salts, solvates, prodrugs, tautomers, enantiomers, stereoisomers, and diastereoisomers of compounds described or referenced herein. For more information regarding small molecule TNFα small molecules, see Trace et al., Annu. Rev. Med. 1994; 45: 491-503; WO2017117684; US2018065959; and U.S. Pat. No. 9,783,538.

(VII) Nanoparticle Formulations. Nanoparticles that result in in vivo genetic modification of cells and/or small molecules described herein can be formulated alone or in combination into compositions for administration to subjects. Compositions include nanoparticles and/or small molecules formulated with at least one pharmaceutically acceptable carrier.

For injection, compositions can be formulated as aqueous solutions, such as in buffers including Hanks' solution, Ringer's solution, or physiological saline. The aqueous solutions can include formulatory agents such as suspending, stabilizing, and/or dispersing agents. Alternatively, the formulation can be in lyophilized and/or powder form for constitution with a suitable vehicle, e.g., sterile pyrogen-free water, before use.

The use of different solvents (for example, dichloromethane, chloroform, ethyl acetate, triacetin, N-methyl pyrrolidone, tetrahydrofuran, phenol, or combinations thereof) can alter nanoparticle size and structure in order to modulate release characteristics. Other useful solvents include water, ethanol, dimethyl sulfoxide (DMSO), N-methyl-2-pyrrolidone (NMP), acetone, methanol, isopropyl alcohol (IPA), ethyl benzoate, and benzyl benzoate.

Exemplary release modifiers can include surfactants, detergents, internal phase viscosity enhancers, complexing agents, surface active molecules, co-solvents, chelators, stabilizers, derivatives of cellulose, (hydroxypropyl)methyl cellulose (HPMC), HPMC acetate, cellulose acetate, pluronics (e.g., F68/F127), polysorbates, Span® (Croda Americas, Wilmington, Delaware), poly(vinyl alcohol) (PVA), Brij® (Croda Americas, Wilmington, Delaware), sucrose acetate isobutyrate (SAIB), salts, and buffers.

Any composition disclosed herein can advantageously include any other pharmaceutically acceptable carriers which include those that do not produce significantly adverse, allergic, or other untoward reactions that outweigh the benefit of administration. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by the US FDA Office of Biological Standards and/or other relevant foreign regulatory agencies.

(VIII) Methods of Use. Methods disclosed herein include treating subjects (humans, veterinary animals (dogs, cats, reptiles, birds, etc.) livestock (horses, cattle, goats, pigs, chickens, etc.) and research animals (monkeys, rats, mice, fish, etc.) with compositions and formulations disclosed herein. Treating subjects includes delivering therapeutically effective amounts. Therapeutically effective amounts include those that provide effective amounts, prophylactic treatments and/or therapeutic treatments.

An "effective amount" is the amount of a composition necessary to result in a desired physiological change in the subject. For example, an effective amount can provide an immunogenic anti-cancer effect. Effective amounts are often administered for research purposes. Effective amounts disclosed herein can cause a statistically-significant effect in an animal model or in vitro assay relevant to the assessment of a cancer's development or progression. An immunogenic composition can be provided in an effective amount, wherein the effective amount stimulates an immune response.

A "prophylactic treatment" includes a treatment administered to a subject who does not display signs or symptoms of a cancer or displays only early signs or symptoms of a cancer such that treatment is administered for the purpose of diminishing or decreasing the risk of developing the cancer further. Thus, a prophylactic treatment functions as a preventative treatment against a cancer. In particular embodiments, prophylactic treatments reduce, delay, or prevent metastasis from a primary a cancer tumor site from occurring.

A "therapeutic treatment" includes a treatment administered to a subject who displays symptoms or signs of a cancer and is administered to the subject for the purpose of diminishing or eliminating those signs or symptoms of the cancer. The therapeutic treatment can reduce, control, or eliminate the presence or activity of the cancer and/or reduce control or eliminate side effects of the cancer.

Function as an effective amount, prophylactic treatment or therapeutic treatment are not mutually exclusive, and in particular embodiments, administered dosages may accomplish more than one treatment type.

In particular embodiments, therapeutically effective amounts provide anti-cancer effects. Anti-cancer effects include a decrease in the number of cancer cells, decrease in the number of metastases, a decrease in tumor volume, an increase in life expectancy, induced chemo- or radiosensitivity in cancer cells, inhibited angiogenesis near cancer cells, inhibited cancer cell proliferation, inhibited tumor growth, prevented or reduced metastases, prolonged subject life, reduced cancer-associated pain, and/or reduced relapse or re-occurrence of cancer following treatment. In particular embodiments, combination treatments disclosed herein enhance the killing of antigen-negative bystander cells.

A "tumor" is a swelling or lesion formed by an abnormal growth of cells (called neoplastic cells or tumor cells). A "tumor cell" is an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be benign, pre-malignant or malignant.

Types of cancer that can be treated using combination treatments as described herein include prostate cancer, breast cancer, stem cell cancer, ovarian cancer, mesothelioma, renal cell carcinoma melanoma, pancreatic cancer, lung cancer, HBV-induced hepatocellular carcinoma, and multiple myeloma. Further exemplary cancers that may be treated include medulloblastoma, oligodendroglioma, ovarian clear cell adenocarcinoma, ovarian endometrioid adenocarcinoma, ovarian serous adenocarcinoma, pancreatic ductal adenocarcinoma, pancreatic endocrine tumor, malignant rhabdoid tumor, astrocytoma, atypical teratoid rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, epitheloid sarcoma, renal medullo carcinoma, diffuse large B-cell lymphoma, follicular lymphoma and not otherwise specified (NOS) sarcoma.

Acute myeloid leukemia (AML), blastic plasmacytoid dendritic cell neoplasm (BPDCN), myelodysplastic syndromes (MDS), natural killer cell lymphomas, hairy cell leukemia, acute lymphocytic leukemia (ALL; also known as acute lymphoblastic lymphoma), chronic myelocytic leukemia (CML), other leukemias, hematological cancers or tumors, Hodgkin's lymphoma (HL), B-cell HL, non-Hodgkin lymphoma (NHL), mantle cell lymphoma (MCL), T cell lymphoma, multiple myeloma (refractory, relapsed, etc.), systemic mastocytosis (SM), hypereosinophilic syndrome (HES), myelofibrosis, anemia, systemic lupus erythematosus (SLE), psoriasis, and systemic sclerosis (scleroderma) may also be treated with combination treatments disclosed herein.

For administration, therapeutically effective amounts (also referred to herein as doses) can be initially estimated based on results from in vitro assays and/or animal model studies. Such information can be used to more accurately determine useful doses in subjects of interest. The actual dose amount administered to a particular subject can be determined by a physician, veterinarian or researcher taking into account parameters such as physical and physiological factors including target, body weight, severity of condition, type of cancer, stage of cancer, previous or concurrent therapeutic interventions, idiopathy of the subject and route of administration.

Therapeutically effective amounts to administer can include greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$.

Useful doses of nanoparticles and/or small molecules can range from 0.1 to 5 μg/kg or from 0.5 to 1 μg/kg. In other examples, a dose can include 1 μg/kg, 15 μg/kg, 30 μg/kg, 50 μg/kg, 55 μg/kg, 70 μg/kg, 90 μg/kg, 150 μg/kg, 350 μg/kg, 500 μg/kg, 750 μg/kg, 1000 μg/kg, 0.1 to 5 mg/kg or from 0.5 to 1 mg/kg. In other examples, a dose can include 1 mg/kg, 10 mg/kg, 30 mg/kg, 50 mg/kg, 70 mg/kg, 100 mg/kg, 300 mg/kg, 500 mg/kg, 700 mg/kg, 1000 mg/kg or more.

An exemplary dose of Birinapant includes from 0.1 to 70 $mg/m^2$. An exemplary dose of LCL161 includes from 10 to 3000 mg. An exemplary dose of AEG35156 includes from 10-500 $mg/m^2$. An exemplary dose of Sirolimus includes a 2-20 mg loading dose and 1-10 mg daily. An exemplary dose of CUDC-427 includes 100-600 mg daily for 14 days in a 21-day cycle.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly). Therapeutically effective amounts can also be achieved by administering doses over 1-4 weeks over a 21 or 28-day cycle.

As indicated, the compositions and formulations disclosed herein can be administered by, e.g., injection, infusion, perfusion, or lavage and can more particularly include administration through one or more bone marrow, intravenous, intradermal, intraarterial, intranodal, intralymphatic, intraperitoneal, intralesional, intraprostatic, intravaginal, intrarectal, topical, intrathecal, intratumoral, intramuscular, intravesicular, and/or subcutaneous infusions and/or bolus injections.

In certain embodiments, cells or nanoparticle- or small molecule-based formulations are administered to a patient in conjunction with (e.g., before, simultaneously or following) any number of relevant treatment modalities. In particular embodiments, cells or nanoparticle- or small molecule-based formulations may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycoplienolic acid, steroids, FR901228, cytokines, and irradiation.

(IX) Kits. Kits disclosed herein include components to carry out a combination therapy disclosed herein. The components can vary based on the particular embodiment being practiced. Embodiments of kits can include one more of, for example, an immune cell (e.g., T cells (e.g., CD4+, CD8+), B cells, NK cells, monocytes/macrophages, lymphocytes, HSCs, HPC, HSPC) pre-genetic modification and/or genetically modified to (i) express a CAR or similar molecule, and/or a TNFα signal potentiator protein or (ii) to have disrupted activity of a TNFRS family member that inhibits a TNFα signaling pathway member (see FIG. 6); a gene encoding a CAR, TCR, CAR/TCR hybrid and/or one more more TNFα signal potentiators (e.g., TWEAK, TRAIL, LIGHT, and see FIG. 6), a molecule that results in the disruption of the expression and/or activity of a TNFRS family member that inhibits a TNFα signaling pathway member (see FIG. 6); a TNFα signal potentiator protein (e.g., TWEAK, TRAIL, LIGHT, and see FIG. 6); a TNFα signal potentiator small molecule (e.g., BV-6, CUDC-427, GDC-0152, LCL161, Rocaglanide, Sirolimus, Escin, Emricasan, Birinapant, ASTX660, AZD5582, KILLERTRAIL™, BI 891065, DEBIO 1143, APG-1387, HGS1029, and AEG35156); wash buffer; PBS; a Percoll and/or Ficoll gradient; a magnetic bead; a vector (e.g., a viral vector), CRISPR gene-editing components; base-editing components; nanoparticles; a bag, cell culture plate, flask, chamber, chromatography column, cross-linked gel, cross-linked polymer, column, culture dish, hollow fiber, microtiter plate, silica-coated glass plate, tube, tubing set, well, vial, or other container for culture or cultivating cells; one or more cytokines, for example, interleukin (IL)-2, IL-7, IL-15 and/or IL-21; a CD3 stimulating molecule; a CD28 stimulating molecule; a 4-1BB stimulating molecule; a Notch agonist; saline, water, Hanks' solution, citrate buffers, succinate buffers, tartrate buffers, fumarate buffers, gluconate buffers, oxalate buffers, lactate buffers, acetate buffers, phosphate buffers, histidine buffers, and/or trimethylamine salts.

(X) Exemplary Embodiments.

1. A combination treatment including
   (i) an immune cell genetically modified to express a chimeric antigen receptor (CAR) including an extracellular component and an intracellular component wherein the extracellular component includes a binding domain that binds an antigen expressed by a cancer cell and wherein the intracellular component includes an effector domain; and
   (ii) a tumor necrosis factor alpha (TNFα) signal potentiator.
2. A combination treatment of embodiment 1, wherein the TNFα signal potentiator activates, enhances, or supports the actions of a tumor necrosis factor receptor superfamily (TNFRSF) member that activates, enhances, or supports a TNFα signaling pathway member and/or wherein the TNFα signal potentiator activates, enhances, or supports the actions of a TNFα signaling pathway member.
3. A combination treatment of embodiment 1 or 2, wherein the TNFα signal potentiator de-activates, suppresses, or disrupts the actions of a TNFRSF member that de-activates, suppresses, or disrupts a TNFα signaling pathway member.
4. A combination treatment of any of embodiments 1-3, wherein the TNFα signal potentiator activates, enhances, or supports TNFRSF members 1A, 1B, 3, 6, 8, 10A, 10B, 12A, 19 and/or 21 and/or de-activates, suppresses, or disrupts the actions of TNFRSF members 6B, 10C, and/or 10D.
5. A combination treatment of any of embodiments 1-4, wherein the TNFα signal potentiator is a molecule that results in expression of a TNFα signal potentiator protein.
6. A combination treatment of any of embodiments 1-5, wherein the TNFα signal potentiator is a TNFα signal potentiator protein.
7. A combination treatment of embodiment 5 or 6, wherein the TNFα signal potentiator protein includes tumor necrosis factor-like weak inducer of apoptosis (TWEAK), Tumor necrosis factor-related apoptosis-inducing ligand (TRAIL), and/or homologous to lymphotoxin, exhibits inducible expression and competes with HSV glycoprotein D for binding to herpesvirus entry mediator, a receptor expressed on T lymphocytes (LIGHT).
8. A combination treatment of any of embodiments 1-7, wherein the TNFα signal potentiator is a molecule that disrupts the expression of a TNFRSF member that de-activates, suppresses, or disrupts a TNFα signaling pathway member.
9. A combination treatment of embodiment 8, wherein the molecule that disrupts the expression of a TNFRSF member that de-activates, suppresses, or disrupts a TNFα signaling pathway member includes a CRISPR/Cas molecule, a zinc finger nuclease molecule, a TALEN, or a megaTAL.
10. A combination treatment of embodiment 8 or 9, wherein the molecule that disrupts the expression of a TNFRSF member that de-activates, suppresses, or disrupts a TNFα signaling pathway member includes a base editor.
11. A combination treatment of any of embodiments 1-10, wherein the immune cell of embodiment 1 that expresses the CAR also includes or expresses the TNFα signal potentiator.
12. A combination treatment of any of embodiments 1-11, wherein the immune cell of embodiment 1 that expresses the CAR is also genetically modified to include or express the TNFα signal potentiator.
13. A combination treatment of any of embodiments 1-12, wherein the TNFα signal potentiator includes a small molecule or protein:

selected from one or more of BV-6, CUDC-427, GDC-0152, LCL161, Escin, Rocaglarnide, Sirolimus, Ernricasan, Birinapant, ASTX660, AZD5582, BI 891065, DEBIO 1143, APG-1387, HGS1029, AEG35156, a recombinant protein having the extracellular domain of human TRAIL, and a recombinant protein having the extracellular domain of human TRAIL and a linker (e.g. KILLERTRAIL™);

selected from one or more of BV-6, CUDC-427, GDC-0152, LCL161, ASTX660, AZD5582, Birinapant, and a recombinant protein having the extracellular domain of human TRAIL, and a recombinant protein having the extracellular domain of human TRAIL and a linker (e.g., KILLERTRAIL™)

selected from one or more of BV-6, CUDC-427, GDC-0152, and LCL161: or selected from one or more of Rocaglamide, Sirolimus, Emricasan, BI 891065, DEBIO 1143, APG-1387, HGS1029, and AEG35156.

14. A combination treatment of any of embodiments 1-13, wherein expression of the CAR and/or TNFα signal potentiator is controlled by the NFAT promoter.

15. A combination treatment of any of embodiments 1-14, wherein the binding domain is a T cell receptor (TCR) or derived from the CDRs of an antibody.

16. A combination treatment of any of embodiments 1-15, wherein the binding domain specifically binds A33; BAGE; Bcl-2; p-catenin; BCMA; B7H4; BTLA; CA125; CA19-9; CD3, CD5; CD20; CD21; CD22; CD25; CD28; CD30; CD33; CD37; CD38; CD40; CD52; CD44v6; CD45; CD56; CD79b; CD80; CD81; CD86; CD123; CD134; CD137; CD151; CD171; CD276; CEA; CEACAM6; CLL-1; c-Met; CS-1; CTLA-4; cyclin 1; DAGE; EBNA; EGFR; EGFRvIII, ephrinB2; ErbB2; HER2; ErbB4; EphA2; estrogen receptor; FAP; ferritin; α-fetoprotein (AFP); FLT1; FLT4; folate-binding protein; FOLR; Frizzled; GAGE; G250; GD-2; GHRHR; GHR; GITR; GM2; GPRC5D; gp75; gp100 (Pmel 17); gp130; HLA; HER-2/neu; HPV E6; HPV E7; hTERT; HVEM; IGF1R; IL6R; KDR; Ki-67; Lewis A; Lewis Y; LIFR3; LRP; LRP5; LT3R; MAGE; MART; mesothelin; MUC; MUC1; MUM-1-B; myc; NYESO-1; O-acetyl GD-2; O-acetyl GD3; OSMRp; p53; PD1; PD-L1; PD-L2; PRAME; progesterone receptor; PSA; PSMA; PTCH1; RANK; ras; Robo1; RORI; survivin; TCRα; TCR3; tenascin; TGFBR1; TGFBR2; TLR7; TLR9; TNFR1; TNFR2; TNFRSF4; TWEAK-R; TSTA tyrosinase; VEGF; or WTI1.

17. A combination treatment of embodiments 1-16, wherein the binding domain specifically binds HER2, ERBB2, CD33, PSMA, PD-L1, MUC16, FOLR, CD123, or CLL-1.

18. A combination treatment of any of embodiments 1-17, wherein the binding domains are derived from antibodies including a CDR set, VH, or VL of FMC63, SJ25C1, HD37, Herceptin, pembrolizumab, FAZ053, Avelumab, Atezolizumab, or Amatuximab.

19. A combination treatment of any of embodiments 1-15, wherein the binding domain includes an scFv.

20. A combination treatment of any of embodiments 1-15 or 19, wherein the binding domain includes (a) a CDRL1 including TASSSVNYIH (SEQ ID NO: 14), a CDRL2 including TSKVAS (SEQ ID NO: 15), a CDRL3 including QQWRSYPLT (SEQ ID NO: 16), a CDRH1 including DYVVH (SEQ ID NO: 17), a CDRH2 including YINPYNDGTKYNEKFKG (SEQ ID NO: 18), and a CDRH3 including DYRYEVYGMDY (SEQ ID NO: 19);

(b) a CDRL1 including RASEVDNYGISFMN (SEQ ID NO: 20), a CDRL2 including AASNQGS (SEQ ID NO: 21), a CDRL3 including QQSKEVPW (SEQ ID NO: 22), a CDRH1 including DYNMH (SEQ ID NO: 23), a CDRH2 including YIYPYNGGTGYNQKFKS (SEQ ID NO: 24), and a CDRH3 including GRPAMDY (SEQ ID NO: 25);

(c) a variable light chain including: DIVL TQ SPTIMSASPGERVTMTCTASSSVNYIHWYQQ KSGDSPKRWIFDTSKVASGVβ ARFSGSGSGTSYSLTISTMEAEDAATYYCQQWRSYPLTF GDGTRLELKRADAAPTVS (SEQ ID NO: 26), and a variable heavy chain including: EVKLQESG PELVKPGASVKMSCKASGYKFTDYVVHWLK QKPGQGLEWIGYINPYNDG TKYNEKFKGK ATLTSDKSSSTAYMEVSSLTSEDSAVYYCARDYRYEVYGMDYWGQGT SVTVSS (SEQ ID NO: 27);

(d) a variable light chain including: DIVLTQSPTI MSASPGERVTMTCTASSSVNYIHWYQQKSG DSPKRWIFDTSKVASGVβ ARFSGSGSGTSYSLTISTMEAEDAATYYCQQWRSYPLTFGDGTRLELKRADAAPTVS (SEQ ID NO: 26), and a variable heavy chain including: DIVLTQ SPAIMSASPGEKVTMTCSANSSVSYIHW YQQKSGTSPKRWIFDTSKLASGVPA RFSGS GSGTSYSLTISTMEAEDAATYYCQQWTSHPLTFGTGTKLQLKRADAAPTVS (SEQ ID NO: 28);

(e) a CDRL1 including RASQDINYYLN (SEQ ID NO: 45), a CDRL2 including YYSSRLHS (SEQ ID NO: 46), a CDRL3 including QQDDALPYT (SEQ ID NO: 47), a CDRH1 including KASGYAFSNYWMN (SEQ ID NO: 48), a CDRH2 including QINPGDGDTN (SEQ ID NO: 49), and a CDRH3 including AREDRDYFDY (SEQ ID NO: 50);

(f) a CDRL1 including QDINYY (SEQ ID NO: 163), a CDRL2 including YSS, a CDRL3 including QQDDALPYT (SEQ ID NO: 47), a CDRH1 including GYAFSNYW (SEQ ID NO: 164), a CDRH2 including INPGDGDT (SEQ ID NO: 165), and a CDRH3 including AREDRDYFDY (SEQ ID NO: 50);

(g) a CDRL1 including RASQDINYYLN (SEQ ID NO: 45), a CDRL2 including YSSRLHS (SEQ ID NO: 166), a CDRL3 including QQDDALPYT (SEQ ID NO: 47), a CDRH1 including NYWMN (SEQ ID NO: 167), a CDRH2 including QINPGDGDTNYNGKFKG (SEQ ID NO: 168), and a CDRH3 including EDRDYFDY (SEQ ID NO: 169);

(h) a CDRL1 including RASQDINYYLN (SEQ ID NO: 45), a CDRL2 including YSSRLHS (SEQ ID NO: 166), a CDRL3 including QQDDALPYT (SEQ ID NO: 47), a CDRH1 including GYAFSNY (SEQ ID NO: 170), a CDRH2 including NPGDGD (SEQ ID NO: 171), and a CDRH3 including EDRDYFDY (SEQ ID NO: 169); or (i) a variable light chain including: DIQMTQTT SSLSASLGDRVTISCRASQDINYYLNWYQQKPDGTVKLLIYYSSRLHSGVβ SRFSGSGS GTDFSLTISNLEQEDIATYFCQQDDALPYTFG GGTKLEIK (SEQ ID NO: 51) and a variable heavy chain including: QVQLQQSGAELVKPGASVKISCKASGYAFSNYWMNWVKQRPGKGLEWIG QINPGDG DTNYNGKFKGKATLTADKSS STAYMQLSSLTSEDSAVYFCAREDRDYFD WGQGTTL TVSS (SEQ ID NO: 52).

21. A combination treatment of any of embodiments 1-20, wherein the extracellular component and the intracellular component are linked through a transmembrane domain.

22. The combination treatment of embodiment 21, wherein the transmembrane domain is the transmembrane domain of the α, β or ζ chain of a T-cell receptor, CD28, CD27, CD3 epsilon, CD45, CD4, CD5, CD8, CD9, CD16, CD22, CD33, CD37, CD64, CD80, CD86, CD134, CD137 or CD154.

23. The combination treatment of embodiment 21, wherein the transmembrane domain is the transmembrane domain of CD28.
24. A combination treatment of any of embodiments 1-23, wherein the effector domain includes an intracellular signaling domain of CD3, CD28, 4-1BB, CD27, OX40, CD30, CD40, PD-1, ICOS, LFA-1, CD2, CD7, LIGHT, NKG2C, and/or B7-H3.
25. A combination treatment of any of embodiments 1-24, wherein the effector domain includes an intracellular signaling domain of CD3, CD28, and/or 4-1BB.
26. A combination treatment of any of embodiments 1-25, wherein the effector domain includes an intracellular signaling domain of CD3ζ and 4-1 BB.
27. A combination treatment of any of embodiments 1-25, wherein the effector domain includes a variant of CD3ζ (SEQ ID NOs: 142 or 143) and a portion of 4-1BB (SEQ ID NO: 147 or 148).
28. A combination treatment of any of embodiments 1-27, wherein the CAR further includes a spacer region between the binding domain and the intracellular component.
29. A combination treatment of embodiment 28, wherein the spacer region includes an immunoglobulin hinge region or portion thereof.
30. A combination treatment of embodiment 29 or 30, wherein the spacer region includes an IgG4 hinge region, an IgG4 hinge region and an IgG4 hinge CH3 region, or an IgG4 hinge region, an IgG4 CH3 region, and an IgG4 CH2 region.
31. A combination treatment of any of embodiments 1-30, wherein the CAR further includes a control feature including a tag cassette, a transduction marker and/or a suicide switch.
32. A combination treatment of any of embodiments 1-31, wherein the CAR is encoded by SEQ ID NO: 176 or 177.
33. A combination treatment of any of embodiments 1-32, wherein the genetically modified immune cell is a T cell, natural killer cell, monocyte/macrophage, hematopoietic stem cell or a hematopoietic progenitor cell.
34. A combination treatment of embodiment 33, wherein the T cell is selected from a CD3 T cell, a CD4 T cell, a CD8 T cell, a central memory T cell, an effector memory T cell, and/or a naïve T cell.
35. A combination treatment of embodiment 33, wherein the T cell is a CD4 T cell and/or a CD8 T cell.
36. A combination treatment of embodiment 35, including a 1:1 ratio of CD4 T cells and CD8 T cells.
37. A combination treatment of any of embodiments 1-36, wherein the genetically modified immune cell is ex vivo or in vivo.
38. A combination treatment of any of embodiments 1-37, wherein the combination treatment includes a composition including at least two cell types genetically modified ex vivo to express the CAR of the selected combination treatment.
39. A combination treatment of embodiment 38, wherein the at least two cell types include T cells and natural killer cells, T cells and monocyte/macrophages, T cells and hematopoietic stem cells, T cells and hematopoietic progenitor cells, natural killer cells and monocyte/macrophages, natural killer cells and hematopoietic stem cells, natural killer cells and hematopoietic progenitor cells, monocyte/macrophages and hematopoietic stem cells, monocyte/macrophages and hematopoietic progenitor cells, or hematopoietic stem cells and hematopoietic progenitor cells.
40. A combination treatment of any of embodiments 139, including nanoparticles that result in in vivo genetic modification of cells to express the CAR portion of the combination treatment.
41. A combination treatment of any of embodiments 1-40, including nanoparticles that result in in vivo genetic modification of cells to express or include a TNFα signal potentiator.
42. A cell genetically modified to include or express a combination treatment of any of embodiments 1-41.
43. A cell of embodiment 42, wherein the expression of a TNFα signal potentiator is controlled by the NFAT promoter.
44. A cell of embodiments 42 or 43, wherein the cell is ex vivo or in vivo.
45. A cell of any of embodiments 42-44, wherein the cell is a T cell, natural killer cell, monocyte/macrophage, hematopoietic stem cell or a hematopoietic progenitor cell.
46. A cell of embodiment 45, wherein the T cell is a CD3 T cell, a CD4 T cell, a CD8 T cell, a central memory T cell, an effector memory T cell, and/or a naïve T cell.
47. A cell of embodiment 45, wherein the T cell is a CD4 T cell and/or a CD8 T cell.
48. A method of treating cancer in a subject in need thereof including administering a therapeutically effective amount of a combination treatment of any of embodiments 1-41 to the subject thereby treating the cancer in the subject in need thereof.
49. A method of embodiment 48, wherein the treating provides an anti-cancer effect.
50. A method of embodiment 49, wherein the anti-cancer effect is against leukemia, prostate cancer, breast cancer, stem cell cancer, ovarian cancer, mesothelioma, renal cell carcinoma melanoma, pancreatic cancer, lung cancer, HBV-induced hepatocellular carcinoma, or multiple myeloma.
51. A kit including components to practice a combination treatment of any of embodiments 1-41, a cell of any of embodiments 42-47, and/or a method of any of embodiments 48-50.

(XI) Closing Paragraphs. The nucleic acid and amino acid sequences provided herein are shown using letter abbreviations for nucleotide bases and amino acid residues, as defined in 37 C.F.R. § 1.822 and set forth in the tables in WIPO Standard ST.25 (1998), Appendix 2, Tables 1 and 3. Only one strand of each nucleic acid sequence is shown, but the complementary strand is understood as included in embodiments where it would be appropriate.

To the extent not explicitly provided herein, coding sequences for proteins disclosed herein and protein sequences for coding sequences disclosed herein can be readily derived from one of ordinary skill in the art.

Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wisconsin) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gln), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (Ile), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, Ile, Phe, Met, and Trp; Group 11 (aliphatic): Gly, Ala, Val, Leu, and Ile; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.](1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M NaH2PO4; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

"Specifically binds" refers to an association of a binding domain (of, for example, a CAR binding domain or a nanoparticle selected cell targeting ligand) to its cognate binding molecule with an affinity or $K_a$ (i.e., an equilibrium association constant of a particular binding interaction with units of 1/M) equal to or greater than $10^5$ $M^{-1}$, while not significantly associating with any other molecules or components in a relevant environment sample. "Specifically binds" is also referred to as "binds" herein. Binding domains may be classified as "high affinity" or "low affinity". In particular embodiments, "high affinity" binding domains refer to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. In particular embodiments, "low affinity" binding domains refer to those binding domains with a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M). In certain embodiments, a binding domain may have "enhanced affinity," which refers to a selected or engineered binding domains with stronger binding to a cognate binding molecule than a wild type (or parent) binding domain. For example, enhanced affinity may be due to a Ka (equilibrium association constant) for the cognate binding molecule that is higher than the reference binding domain or due to a $K_d$ (dissociation constant) for the cognate binding molecule that is less than that of the reference binding domain, or due to an off-rate ($K_{off}$) for the cognate binding molecule that is less than that of the reference binding domain. A variety of assays are known for detecting binding domains that specifically bind a particular cognate binding molecule as well as determining binding affinities, such as Western blot, ELISA, and BIACORE® analysis (see also, e.g., Scatchard, et al., 1949, *Ann. N. Y. Acad. Sci.* 51:660; and U.S. Pat. Nos. 5,283,173, 5,468,614, or the equivalent).

Unless otherwise indicated, the practice of the present disclosure can employ conventional techniques of immunology, molecular biology, microbiology, cell biology and recombinant DNA. These methods are described in the following publications. See, e.g., Sambrook, et al. Molecular Cloning: A Laboratory Manual, 2nd Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in the antigen-independent killing of unwanted cells (e.g., cancer cells).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or +1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

What is claimed is:

1. An immune cell genetically modified to express:

(i) a first molecule comprising a chimeric antigen receptor (CAR) comprising an extracellular component linked to an intracellular component by a transmembrane domain, wherein the extracellular component comprises a binding domain that binds an antigen expressed by a cancer cell and wherein the intracellular component comprises an effector domain; and (ii) a second molecule comprising a tumor necrosis factor alpha (TNFα) signal potentiator comprising tumor necrosis factor-like weak inducer of apoptosis (TWEAK);

Tumor necrosis factor-related apoptosis-inducing ligand (TRAIL); or tumor necrosis factor superfamily member 14 (LIGHT).

2. The immune cell of claim 1, wherein the TRAIL is recombinant TRAIL linked to a His tag and a linker peptide.

3. The immune cell of claim 2, wherein an extracellular domain of the recombinant TRAIL is linked to the His tag and the linker peptide.

4. The immune cell of claim 1, wherein expression of the CAR and/or TNFα signal potentiator is controlled by an NFAT promoter.

5. The immune cell of claim 1, wherein the binding domain is a T cell receptor (TCR) or derived from the CDRs of an antibody.

6. The immune cell of claim 2, wherein the binding domain specifically binds CD33; A33; BAGE; Bcl-2; p-catenin; BCMA; B7H4; BTLA; CA125; CA19-9; CD3, CD5; CD20; CD21; CD22; CD25; CD28; CD30; CD37; CD38; CD40; CD52; CD44v6; CD45; CD56; CD79b; CD80; CD81; CD86; CD123; CD134; CD137; CD151; CD171; CD276; CEA; CEACAM6; CLL-1; c-Met; CS-1; CTLA-4; cyclin 1; DAGE; EBNA; EGFR; EGFRvIII, ephrinB2; ErbB2; HER2; ErbB4; EphA2; estrogen receptor; FAP; ferritin; α-fetoprotein (AFP); FLT1; FLT4; folate-binding protein; FOLR; Frizzled; GAGE; G250; GD-2; GHRHR; GHR; GITR; GM2; GPRC5D; gp75; gp100 (Pmel 17); gp130; HLA; HER-2/neu; HPV E6; HPV E7; hTERT; HVEM; IGF1R; IL6R; KDR; Ki-67; Lewis A; Lewis Y; LIFRP; LRP; LRP5; LTPR; MAGE; MART; mesothelin; MUC; MUC1; MUC16; MUM-1-B; myc; NYESO-1; O-acetyl GD-2; O-acetyl GD3; OSMRβ; p53; PD1; PD-L1; PD-L2; PRAME; progesterone receptor; PSA; PSMA; PTCH1; RANK; ras; Robo1; RORI; survivin; TCRα; TCRβ; tenascin; TGFBR1; TGFBR2; TLR7; TLR9; TNFR1; TNFR2; TNFRSF4; TWEAK-R; TSTA tyrosinase; VEGF; or WT1.

7. The immune cell of claim 1, wherein the binding domain is derived from an antibody comprising a CDR set or VH and VL of FMC63, SJ25C1, HD37, Herceptin, gpembrolizumab, FAZ053, Avelumab, Atezolizumab, or Amatuximab.

8. The immune cell of claim 1, wherein the effector domain comprises 4-1BB and/or CD3ζ.

9. The immune cell of claim 1, wherein the CAR further comprises or is expressed with a control feature comprising a tag cassette, a transduction marker, and/or a suicide switch.

10. The immune cell of claim 1, wherein the genetically modified immune cell is a T cell, natural killer cell, monocyte/macrophage, hematopoietic stem cell, or a hematopoietic progenitor cell.

11. The immune cell of claim 10, wherein the T cell is a CD4 T cell or a CD8 T cell.

12. The immune cell of claim 1, wherein the genetically modified immune cell is ex vivo or in vivo.

13. The immune cell of claim 1, wherein the immune cell is genetically modified by administration of nanoparticles comprising nucleic acids encoding the CAR and/or the TNFα signal potentiator.

14. A method of treating cancer in a subject in need thereof comprising administering a therapeutically effective amount of a formulation comprising the immune cell of claim 1 to the subject, thereby treating the cancer in the subject in need thereof.

15. The method of claim 14, wherein the treating provides an anti-cancer effect against leukemia, prostate cancer, breast cancer, stem cell cancer, ovarian cancer, mesothelioma, renal cell carcinoma melanoma, pancreatic cancer, lung cancer, HBV-induced hepatocellular carcinoma, or multiple myeloma.

16. A system comprising:

(i) a first nucleic acid encoding a chimeric antigen receptor (CAR), that when expressed by a cell, comprises an extracellular component linked to an intracellular component by a transmembrane domain, wherein the extracellular component comprises a binding domain that binds an antigen expressed by a cancer cell and wherein the intracellular component comprises an effector domain; and (ii) (a) a second nucleic acid encoding a tumor necrosis factor alpha (TNFα) signal potentiator comprising:

tumor necrosis factor-like weak inducer of apoptosis (TWEAK);

Tumor necrosis factor-related apoptosis-inducing ligand (TRAIL); or tumor necrosis factor superfamily member 14 (LIGHT); or (b) a small molecule TNFα signal potentiator selected from the group consisting of BV-6, CUDC-427, GDC-0152, LCL161, Rocaglamide, Escin, Emricasan, Birinapant, ASTX660, AZD5582, BI 891065, DEBIO 1143, APG-1387, HGS1029, and AEG35156.

17. The system of claim 16, wherein the system comprises the first nucleic acid and the second nucleic acid within a vector.

18. The system of claim 16, wherein the first nucleic acid is operably linked to an NFAT promoter.

19. The system of claim 16, wherein the second nucleic acid is operably linked to an NFAT promoter.

20. The system of claim 16, wherein the first nucleic acid and the second nucleic acid are operably linked to a same NFAT promoter.

* * * * *

SEQUENCE LISTING

```
<160> NUMBER OF SEQ ID NOS: 178

<210> SEQ ID NO 1
<211> LENGTH: 50
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (5)..(50)
<223> OTHER INFORMATION: (GlyGlyGlyGlySer) sequence can be present or
      absent

<400> SEQUENCE: 1

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50


<210> SEQ ID NO 2
<211> LENGTH: 90
```

<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (5)..(40)
<223> OTHER INFORMATION: (GlyGlyGlySer) sequence can be present or absent
<220> FEATURE:
<221> NAME/KEY: MISC_FEATURE
<222> LOCATION: (46)..(90)
<223> OTHER INFORMATION: (GlyGlyGlyGlySer) sequence can be present or absent

<400> SEQUENCE: 2

```
Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser
                85                  90
```

<210> SEQ ID NO 3
<211> LENGTH: 70
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (5)..(40)
<223> OTHER INFORMATION: (GlyGlyGlySer) sequence can be present or absent
<220> FEATURE:
<221> NAME/KEY: MISC_FEATURE
<222> LOCATION: (44)..(70)
<223> OTHER INFORMATION: (GlyGlySer) sequence can be present or absent

<400> SEQUENCE: 3

```
Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Ser Gly Gly Ser Gly Gly
        35                  40                  45

Ser Gly Gly Ser Gly Gly Ser Gly Gly Ser Gly Gly Ser Gly Gly Ser
    50                  55                  60

Gly Gly Ser Gly Gly Ser
65                  70
```

<210> SEQ ID NO 4
<211> LENGTH: 45
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (5)..(40)

```
<223> OTHER INFORMATION: (GlyGlyGlySer) sequence can be present or
      absent

<400> SEQUENCE: 4

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Gly Ser
        35                  40                  45


<210> SEQ ID NO 5
<211> LENGTH: 5
<212> TYPE: PRT
<213> ORGANISM: Artificial Sequence
<220> FEATURE:
<223> OTHER INFORMATION: GlySer linker

<400> SEQUENCE: 5

Gly Gly Gly Gly Ser
1               5


<210> SEQ ID NO 6
<211> LENGTH: 4
<212> TYPE: PRT
<213> ORGANISM: Artificial Sequence
<220> FEATURE:
<223> OTHER INFORMATION: GlySer linker

<400> SEQUENCE: 6

Gly Gly Gly Ser
1


<210> SEQ ID NO 7
<211> LENGTH: 20
<212> TYPE: PRT
<213> ORGANISM: Artificial Sequence
<220> FEATURE:
<223> OTHER INFORMATION: GlySer linker

<400> SEQUENCE: 7

Gly Gly Gly Gly Ser Gly Gly Gly Gly Ser Gly Gly Gly Gly Ser Gly
1               5                   10                  15

Gly Gly Gly Ser
            20


<210> SEQ ID NO 8
<211> LENGTH: 15
<212> TYPE: PRT
<213> ORGANISM: Artificial Sequence
<220> FEATURE:
<223> OTHER INFORMATION: GlySer linker

<400> SEQUENCE: 8

Gly Gly Gly Gly Ser Gly Gly Gly Gly Ser Gly Gly Gly Gly Ser
1               5                   10                  15


<210> SEQ ID NO 9

<400> SEQUENCE: 9

000


<210> SEQ ID NO 10
```

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14
<211> LENGTH: 10
<212> TYPE: PRT
<213> ORGANISM: Artificial Sequence
<220> FEATURE:
<223> OTHER INFORMATION: anti-CD33 CDRL1

<400> SEQUENCE: 14

Thr Ala Ser Ser Ser Val Asn Tyr Ile His
1               5                   10

<210> SEQ ID NO 15
<211> LENGTH: 6
<212> TYPE: PRT
<213> ORGANISM: Artificial Sequence
<220> FEATURE:
<223> OTHER INFORMATION: anti-CD33 CDRL2

<400> SEQUENCE: 15

Thr Ser Lys Val Ala Ser
1               5

<210> SEQ ID NO 16
<211> LENGTH: 9
<212> TYPE: PRT
<213> ORGANISM: Artificial Sequence
<220> FEATURE:
<223> OTHER INFORMATION: anti-CD33 CDRL3

<400> SEQUENCE: 16

Gln Gln Trp Arg Ser Tyr Pro Leu Thr
1               5

<210> SEQ ID NO 17
<211> LENGTH: 5
<212> TYPE: PRT
<213> ORGANISM: Artificial Sequence
<220> FEATURE:
<223> OTHER INFORMATION: anti-CD33 CDRH1

<400> SEQUENCE: 17

Asp Tyr Val Val His
1               5

<210> SEQ ID NO 18

-continued

<211> LENGTH: 17
<212> TYPE: PRT
<213> ORGANISM: Artificial Sequence
<220> FEATURE:
<223> OTHER INFORMATION: anti-CD33 CDRH2

<400> SEQUENCE: 18

Tyr Ile Asn Pro Tyr Asn Asp Gly Thr Lys Tyr Asn Glu Lys Phe Lys
1 5 10 15

Gly

<210> SEQ ID NO 19
<211> LENGTH: 11
<212> TYPE: PRT
<213> ORGANISM: Artificial Sequence
<220> FEATURE:
<223> OTHER INFORMATION: anti-CD33 CDRH3

<400> SEQUENCE: 19

Asp Tyr Arg Tyr Glu Val Tyr Gly Met Asp Tyr
1 5 10

<210> SEQ ID NO 20
<211> LENGTH: 14
<212> TYPE: PRT
<213> ORGANISM: Artificial Sequence
<220> FEATURE:
<223> OTHER INFORMATION: anti-CD33 CDRL1

<400> SEQUENCE: 20

Arg Ala Ser Glu Val Asp Asn Tyr Gly Ile Ser Phe Met Asn
1 5 10

<210> SEQ ID NO 21
<211> LENGTH: 7
<212> TYPE: PRT
<213> ORGANISM: Artificial Sequence
<220> FEATURE:
<223> OTHER INFORMATION: anti-CD33 CDRL2

<400> SEQUENCE: 21

Ala Ala Ser Asn Gln Gly Ser
1 5

<210> SEQ ID NO 22
<211> LENGTH: 8
<212> TYPE: PRT
<213> ORGANISM: Artificial Sequence
<220> FEATURE:
<223> OTHER INFORMATION: anti-CD33 CDRL3

<400> SEQUENCE: 22

Gln Gln Ser Lys Glu Val Pro Trp
1 5

<210> SEQ ID NO 23
<211> LENGTH: 5
<212> TYPE: PRT
<213> ORGANISM: Artificial Sequence
<220> FEATURE:
<223> OTHER INFORMATION: anti-CD33 CDRH1

<400> SEQUENCE: 23

Asp Tyr Asn Met His
1 5

<210> SEQ ID NO 24
<211> LENGTH: 17
<212> TYPE: PRT
<213> ORGANISM: Artificial Sequence
<220> FEATURE:
<223> OTHER INFORMATION: anti-CD33 CDRH2

<400> SEQUENCE: 24

```
Tyr Ile Tyr Pro Tyr Asn Gly Gly Thr Gly Tyr Asn Gln Lys Phe Lys
1               5                   10                  15

Ser
```

<210> SEQ ID NO 25
<211> LENGTH: 7
<212> TYPE: PRT
<213> ORGANISM: Artificial Sequence
<220> FEATURE:
<223> OTHER INFORMATION: anti-CD33 CDRH3

<400> SEQUENCE: 25

```
Gly Arg Pro Ala Met Asp Tyr
1               5
```

<210> SEQ ID NO 26
<211> LENGTH: 115
<212> TYPE: PRT
<213> ORGANISM: Artificial Sequence
<220> FEATURE:
<223> OTHER INFORMATION: anti-CD33 variable light chain

<400> SEQUENCE: 26

```
Asp Ile Val Leu Thr Gln Ser Pro Thr Ile Met Ser Ala Ser Pro Gly
1               5                   10                  15

Glu Arg Val Thr Met Thr Cys Thr Ala Ser Ser Ser Val Asn Tyr Ile
            20                  25                  30

His Trp Tyr Gln Gln Lys Ser Gly Asp Ser Pro Lys Arg Trp Ile Phe
        35                  40                  45

Asp Thr Ser Lys Val Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Arg Ser Tyr Pro Leu Thr
                85                  90                  95

Phe Gly Asp Gly Thr Arg Leu Glu Leu Lys Arg Ala Asp Ala Ala Pro
            100                 105                 110

Thr Val Ser
        115
```

<210> SEQ ID NO 27
<211> LENGTH: 120
<212> TYPE: PRT
<213> ORGANISM: Artificial Sequence
<220> FEATURE:
<223> OTHER INFORMATION: anti-CD33 variable heavy chain

<400> SEQUENCE: 27

```
Glu Val Lys Leu Gln Glu Ser Gly Pro Glu Leu Val Lys Pro Gly Ala
1               5                   10                  15

Ser Val Lys Met Ser Cys Lys Ala Ser Gly Tyr Lys Phe Thr Asp Tyr
            20                  25                  30

Val Val His Trp Leu Lys Gln Lys Pro Gly Gln Gly Leu Glu Trp Ile
        35                  40                  45
```

```
Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Val Ser Ser Leu Thr Ser Glu Asp Ser Ala Val Tyr Tyr Cys
                85                  90                  95

Ala Arg Asp Tyr Arg Tyr Glu Val Tyr Gly Met Asp Tyr Trp Gly Gln
            100                 105                 110

Gly Thr Ser Val Thr Val Ser Ser
        115                 120


<210> SEQ ID NO 28
<211> LENGTH: 115
<212> TYPE: PRT
<213> ORGANISM: Artificial Sequence
<220> FEATURE:
<223> OTHER INFORMATION: anti-CD33 variable heavy chain

<400> SEQUENCE: 28

Asp Ile Val Leu Thr Gln Ser Pro Ala Ile Met Ser Ala Ser Pro Gly
1               5                   10                  15

Glu Lys Val Thr Met Thr Cys Ser Ala Asn Ser Ser Val Ser Tyr Ile
            20                  25                  30

His Trp Tyr Gln Gln Lys Ser Gly Thr Ser Pro Lys Arg Trp Ile Phe
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Thr Ser His Pro Leu Thr
                85                  90                  95

Phe Gly Thr Gly Thr Lys Leu Gln Leu Lys Arg Ala Asp Ala Ala Pro
            100                 105                 110

Thr Val Ser
        115


<210> SEQ ID NO 29

<400> SEQUENCE: 29

000


<210> SEQ ID NO 30

<400> SEQUENCE: 30

000


<210> SEQ ID NO 31

<400> SEQUENCE: 31

000


<210> SEQ ID NO 32

<400> SEQUENCE: 32

000
```

-continued

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45
<211> LENGTH: 11
<212> TYPE: PRT
<213> ORGANISM: Artificial Sequence
<220> FEATURE:
<223> OTHER INFORMATION: CDRL1 of 1H7 (North, Kabat, and Chothia)

<400> SEQUENCE: 45

Arg Ala Ser Gln Asp Ile Asn Tyr Tyr Leu Asn
1               5                   10

<210> SEQ ID NO 46
<211> LENGTH: 8
<212> TYPE: PRT
<213> ORGANISM: Artificial Sequence
<220> FEATURE:
<223> OTHER INFORMATION: CDRL2 of 1H7 (North)

<400> SEQUENCE: 46

Tyr Tyr Ser Ser Arg Leu His Ser
1               5

<210> SEQ ID NO 47
<211> LENGTH: 9
<212> TYPE: PRT
<213> ORGANISM: Artificial Sequence
<220> FEATURE:
<223> OTHER INFORMATION: CDRL3 of 1H7 (North, IMGT, Kabat, and Chothia)

<400> SEQUENCE: 47

Gln Gln Asp Asp Ala Leu Pro Tyr Thr
1               5

<210> SEQ ID NO 48
<211> LENGTH: 13
<212> TYPE: PRT
<213> ORGANISM: Artificial Sequence
<220> FEATURE:
<223> OTHER INFORMATION: CDRH1 of 1H7 (North)

<400> SEQUENCE: 48

Lys Ala Ser Gly Tyr Ala Phe Ser Asn Tyr Trp Met Asn
1               5                   10

<210> SEQ ID NO 49
<211> LENGTH: 10
<212> TYPE: PRT
<213> ORGANISM: Artificial Sequence
<220> FEATURE:
<223> OTHER INFORMATION: CDRH2 of 1H7 (North)

<400> SEQUENCE: 49

Gln Ile Asn Pro Gly Asp Gly Asp Thr Asn
1               5                   10

<210> SEQ ID NO 50
<211> LENGTH: 10
<212> TYPE: PRT
<213> ORGANISM: Artificial Sequence
<220> FEATURE:
<223> OTHER INFORMATION: CDRH3 of 1H7 (North and IMGT)

<400> SEQUENCE: 50

-continued

```
Ala Arg Glu Asp Arg Asp Tyr Phe Asp Tyr
1               5                   10


<210> SEQ ID NO 51
<211> LENGTH: 107
<212> TYPE: PRT
<213> ORGANISM: Artificial Sequence
<220> FEATURE:
<223> OTHER INFORMATION: variable light chain of 1H7

<400> SEQUENCE: 51

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Tyr Tyr
            20                  25                  30

Leu Asn Trp Tyr Gln Gln Lys Pro Asp Gly Thr Val Lys Leu Leu Ile
        35                  40                  45

Tyr Tyr Ser Ser Arg Leu His Ser Gly Val Pro Ser Arg Phe Ser Gly
    50                  55                  60

Ser Gly Ser Gly Thr Asp Phe Ser Leu Thr Ile Ser Asn Leu Glu Gln
65                  70                  75                  80

Glu Asp Ile Ala Thr Tyr Phe Cys Gln Gln Asp Asp Ala Leu Pro Tyr
                85                  90                  95

Thr Phe Gly Gly Gly Thr Lys Leu Glu Ile Lys
            100                 105


<210> SEQ ID NO 52
<211> LENGTH: 117
<212> TYPE: PRT
<213> ORGANISM: Artificial Sequence
<220> FEATURE:
<223> OTHER INFORMATION: variable heavy chain of 1H7

<400> SEQUENCE: 52

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Ser Asn Tyr
            20                  25                  30

Trp Met Asn Trp Val Lys Gln Arg Pro Gly Lys Gly Leu Glu Trp Ile
        35                  40                  45

Gly Gln Ile Asn Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Glu Asp Arg Asp Tyr Phe Asp Tyr Trp Gly Gln Gly Thr Thr
            100                 105                 110

Leu Thr Val Ser Ser
        115


<210> SEQ ID NO 53
<211> LENGTH: 11
<212> TYPE: PRT
<213> ORGANISM: Artificial Sequence
<220> FEATURE:
<223> OTHER INFORMATION: anti-HER2 CDRL1

<400> SEQUENCE: 53

Lys Ala Ser Gln Asp Val Ser Ile Gly Val Ala
```

-continued 1 5 10

<210> SEQ ID NO 54
<211> LENGTH: 6
<212> TYPE: PRT
<213> ORGANISM: Artificial Sequence
<220> FEATURE:
<223> OTHER INFORMATION: anti-HER2 CDRL2

<400> SEQUENCE: 54

Ala Ser Tyr Arg Tyr Thr
1 5

<210> SEQ ID NO 55
<211> LENGTH: 9
<212> TYPE: PRT
<213> ORGANISM: Artificial Sequence
<220> FEATURE:
<223> OTHER INFORMATION: anti-HER2 CDRL3

<400> SEQUENCE: 55

Gln Gln Tyr Tyr Ile Tyr Pro Tyr Thr
1 5

<210> SEQ ID NO 56
<211> LENGTH: 10
<212> TYPE: PRT
<213> ORGANISM: Artificial Sequence
<220> FEATURE:
<223> OTHER INFORMATION: anti-HER2 CDRH1

<400> SEQUENCE: 56

Gly Phe Thr Phe Thr Asp Tyr Thr Met Asp
1 5 10

<210> SEQ ID NO 57
<211> LENGTH: 16
<212> TYPE: PRT
<213> ORGANISM: Artificial Sequence
<220> FEATURE:
<223> OTHER INFORMATION: anti-HER2 CDRH2

<400> SEQUENCE: 57

Asp Val Asn Pro Asn Ser Gly Gly Ser Ile Tyr Asn Gln Arg Phe Lys
1 5 10 15

<210> SEQ ID NO 58
<211> LENGTH: 9
<212> TYPE: PRT
<213> ORGANISM: Artificial Sequence
<220> FEATURE:
<223> OTHER INFORMATION: anti-HER2 CDRH3

<400> SEQUENCE: 58

Leu Gly Pro Ser Phe Tyr Phe Asp Tyr
1 5

<210> SEQ ID NO 59
<211> LENGTH: 15
<212> TYPE: PRT
<213> ORGANISM: Artificial Sequence
<220> FEATURE:
<223> OTHER INFORMATION: anti-PD-L1 CDRL1

<400> SEQUENCE: 59

Arg Ala Ser Lys Gly Val Ser Thr Ser Gly Tyr Ser Tyr Leu His
1 5 10 15

<210> SEQ ID NO 60
<211> LENGTH: 7
<212> TYPE: PRT
<213> ORGANISM: Artificial Sequence
<220> FEATURE:
<223> OTHER INFORMATION: anti-PD-L1 CDRL2

<400> SEQUENCE: 60

Leu Ala Ser Tyr Leu Glu Ser
1               5

<210> SEQ ID NO 61
<211> LENGTH: 9
<212> TYPE: PRT
<213> ORGANISM: Artificial Sequence
<220> FEATURE:
<223> OTHER INFORMATION: anti-PD-L1 CDRL3

<400> SEQUENCE: 61

Gln His Ser Arg Asp Leu Pro Leu Thr
1               5

<210> SEQ ID NO 62
<211> LENGTH: 5
<212> TYPE: PRT
<213> ORGANISM: Artificial Sequence
<220> FEATURE:
<223> OTHER INFORMATION: anti-PD-L1 CDRH1

<400> SEQUENCE: 62

Asn Tyr Tyr Met Tyr
1               5

<210> SEQ ID NO 63
<211> LENGTH: 17
<212> TYPE: PRT
<213> ORGANISM: Artificial Sequence
<220> FEATURE:
<223> OTHER INFORMATION: anti-PD-L1 CDRH2

<400> SEQUENCE: 63

Gly Ile Asn Pro Ser Asn Gly Gly Thr Asn Phe Asn Glu Lys Phe Lys
1               5                   10                  15

Asn

<210> SEQ ID NO 64
<211> LENGTH: 11
<212> TYPE: PRT
<213> ORGANISM: Artificial Sequence
<220> FEATURE:
<223> OTHER INFORMATION: anti-PD-L1 CDRH3

<400> SEQUENCE: 64

Arg Asp Tyr Arg Phe Asp Met Gly Phe Asp Tyr
1               5                   10

<210> SEQ ID NO 65
<211> LENGTH: 110
<212> TYPE: PRT
<213> ORGANISM: Artificial Sequence
<220> FEATURE:
<223> OTHER INFORMATION: variable light chain of Avelumab

<400> SEQUENCE: 65

Gln Ser Ala Leu Thr Gln Pro Ala Ser Val Ser Gly Ser Pro Gly Gln

```
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110


<210> SEQ ID NO 66
<211> LENGTH: 120
<212> TYPE: PRT
<213> ORGANISM: Artificial Sequence
<220> FEATURE:
<223> OTHER INFORMATION: variable heavy chain of Avelumab

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120


<210> SEQ ID NO 67
<211> LENGTH: 14
<212> TYPE: PRT
<213> ORGANISM: Artificial Sequence
<220> FEATURE:
<223> OTHER INFORMATION: CDRL1 of Avelumab

<400> SEQUENCE: 67

Thr Gly Thr Ser Ser Asp Val Gly Gly Tyr Asn Tyr Val Ser
1               5                   10


<210> SEQ ID NO 68
<211> LENGTH: 7
<212> TYPE: PRT
<213> ORGANISM: Artificial Sequence
<220> FEATURE:
<223> OTHER INFORMATION: CDRL2 of Avelumab

<400> SEQUENCE: 68

Asp Val Ser Asn Arg Pro Ser
1               5
```

<210> SEQ ID NO 69
<211> LENGTH: 10
<212> TYPE: PRT
<213> ORGANISM: Artificial Sequence
<220> FEATURE:
<223> OTHER INFORMATION: CDRL3 of Avelumab

<400> SEQUENCE: 69

Ser Ser Tyr Thr Ser Ser Ser Thr Arg Val
1               5                   10

<210> SEQ ID NO 70
<211> LENGTH: 11
<212> TYPE: PRT
<213> ORGANISM: Artificial Sequence
<220> FEATURE:
<223> OTHER INFORMATION: CDRH1 of Avelumab

<400> SEQUENCE: 70

Ser Gly Phe Thr Phe Ser Ser Tyr Ile Met Met
1               5                   10

<210> SEQ ID NO 71
<211> LENGTH: 17
<212> TYPE: PRT
<213> ORGANISM: Artificial Sequence
<220> FEATURE:
<223> OTHER INFORMATION: CDRH2 of Avelumab

<400> SEQUENCE: 71

Ser Ile Tyr Pro Ser Gly Gly Ile Thr Phe Tyr Ala Asp Thr Val Lys
1               5                   10                  15

Gly

<210> SEQ ID NO 72
<211> LENGTH: 11
<212> TYPE: PRT
<213> ORGANISM: Artificial Sequence
<220> FEATURE:
<223> OTHER INFORMATION: CDRH3 of Avelumab

<400> SEQUENCE: 72

Ile Lys Leu Gly Thr Val Thr Thr Val Asp Tyr
1               5                   10

<210> SEQ ID NO 73
<211> LENGTH: 107
<212> TYPE: PRT
<213> ORGANISM: Artificial Sequence
<220> FEATURE:
<223> OTHER INFORMATION: variable light chain of Atezolizumab

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
85 90 95

Thr Phe Gly Gln Gly Thr Lys Val Glu Ile Lys
100 105

<210> SEQ ID NO 74
<211> LENGTH: 118
<212> TYPE: PRT
<213> ORGANISM: Artificial Sequence
<220> FEATURE:
<223> OTHER INFORMATION: variable heavy chain of Atezolizumab

<400> SEQUENCE: 74

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Ser
20 25 30

Trp Ile His Trp Val Arg Gln Ala Pro Gly Lys Gly Leu Glu Trp Val
35 40 45

Ala Trp Ile Ser Pro Tyr Gly Gly Ser Thr Tyr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Arg His Trp Pro Gly Gly Phe Asp Tyr Trp Gly Gln Gly Thr
100 105 110

Leu Val Thr Val Ser Ser
115

<210> SEQ ID NO 75
<211> LENGTH: 11
<212> TYPE: PRT
<213> ORGANISM: Artificial Sequence
<220> FEATURE:
<223> OTHER INFORMATION: CDRL1 of Atezolizumab

<400> SEQUENCE: 75

Arg Ala Ser Gln Asp Val Ser Thr Ala Val Ala
1 5 10

<210> SEQ ID NO 76
<211> LENGTH: 7
<212> TYPE: PRT
<213> ORGANISM: Artificial Sequence
<220> FEATURE:
<223> OTHER INFORMATION: CDRL2 of Atezolizumab

<400> SEQUENCE: 76

Ser Ala Ser Phe Leu Tyr Ser
1 5

<210> SEQ ID NO 77
<211> LENGTH: 9
<212> TYPE: PRT
<213> ORGANISM: Artificial Sequence
<220> FEATURE:
<223> OTHER INFORMATION: CDRL3 of Atezolizumab

<400> SEQUENCE: 77

Gln Gln Tyr Leu Tyr His Pro Ala Thr
1 5

<210> SEQ ID NO 78
<211> LENGTH: 11
<212> TYPE: PRT
<213> ORGANISM: Artificial Sequence
<220> FEATURE:
<223> OTHER INFORMATION: CDRH1 of Atezolizumab

<400> SEQUENCE: 78

Ser Gly Phe Thr Phe Ser Asp Ser Trp Ile His
1 5 10

<210> SEQ ID NO 79
<211> LENGTH: 17
<212> TYPE: PRT
<213> ORGANISM: Artificial Sequence
<220> FEATURE:
<223> OTHER INFORMATION: CDRH2 of Atezolizumab

<400> SEQUENCE: 79

Trp Ile Ser Pro Tyr Gly Gly Ser Thr Tyr Tyr Ala Asp Ser Val Lys
1 5 10 15

Gly

<210> SEQ ID NO 80
<211> LENGTH: 9
<212> TYPE: PRT
<213> ORGANISM: Artificial Sequence
<220> FEATURE:
<223> OTHER INFORMATION: CDRH3 of Atezolizumab

<400> SEQUENCE: 80

Arg His Trp Pro Gly Gly Phe Asp Tyr
1 5

<210> SEQ ID NO 81
<211> LENGTH: 11
<212> TYPE: PRT
<213> ORGANISM: Artificial Sequence
<220> FEATURE:
<223> OTHER INFORMATION: anti-PSMA CDRL1

<400> SEQUENCE: 81

Lys Ala Ser Gln Asp Val Gly Thr Ala Val Asp
1 5 10

<210> SEQ ID NO 82
<211> LENGTH: 7
<212> TYPE: PRT
<213> ORGANISM: Artificial Sequence
<220> FEATURE:
<223> OTHER INFORMATION: anti-PSMA CDRL2

<400> SEQUENCE: 82

Trp Ala Ser Thr Arg His Thr
1 5

<210> SEQ ID NO 83
<211> LENGTH: 9
<212> TYPE: PRT
<213> ORGANISM: Artificial Sequence
<220> FEATURE:
<223> OTHER INFORMATION: anti-PSMA CDRL3

<400> SEQUENCE: 83

Gln Gln Tyr Asn Ser Tyr Pro Leu Thr 1 5

<210> SEQ ID NO 84
<211> LENGTH: 10
<212> TYPE: PRT
<213> ORGANISM: Artificial Sequence
<220> FEATURE:
<223> OTHER INFORMATION: anti-PSMA CDRH1

<400> SEQUENCE: 84

Gly Tyr Thr Phe Thr Glu Tyr Thr Ile His
1 5 10

<210> SEQ ID NO 85
<211> LENGTH: 17
<212> TYPE: PRT
<213> ORGANISM: Artificial Sequence
<220> FEATURE:
<223> OTHER INFORMATION: anti-PSMA CDRH2

<400> SEQUENCE: 85

Asn Ile Asn Pro Asn Asn Gly Gly Thr Thr Tyr Asn Gln Lys Phe Glu
1 5 10 15

Asp

<210> SEQ ID NO 86
<211> LENGTH: 6
<212> TYPE: PRT
<213> ORGANISM: Artificial Sequence
<220> FEATURE:
<223> OTHER INFORMATION: anti-PSMA CDRH3

<400> SEQUENCE: 86

Gly Trp Asn Phe Asp Tyr
1 5

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98
<211> LENGTH: 106
<212> TYPE: PRT
<213> ORGANISM: Artificial Sequence
<220> FEATURE:
<223> OTHER INFORMATION: variable light chain of Amatuximab

<400> SEQUENCE: 98

```
Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Ser Gly Thr Lys Val Glu Ile Lys
            100                 105
```

<210> SEQ ID NO 99
<211> LENGTH: 119
<212> TYPE: PRT
<213> ORGANISM: Artificial Sequence
<220> FEATURE:
<223> OTHER INFORMATION: variable heavy chain of Amatuximab

<400> SEQUENCE: 99

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Ser Gly
            100                 105                 110

Thr Pro Val Thr Val Ser Ser
        115

<210> SEQ ID NO 100
<211> LENGTH: 10
<212> TYPE: PRT
<213> ORGANISM: Artificial Sequence
<220> FEATURE:
<223> OTHER INFORMATION: CDRL1 of Amatuximab

<400> SEQUENCE: 100

Ser Ala Ser Ser Ser Val Ser Tyr Met His
1               5                   10

<210> SEQ ID NO 101
<211> LENGTH: 7
<212> TYPE: PRT
<213> ORGANISM: Artificial Sequence
<220> FEATURE:
<223> OTHER INFORMATION: CDRL2 of Amatuximab

<400> SEQUENCE: 101

Asp Thr Ser Lys Leu Ala Ser
1               5

<210> SEQ ID NO 102
<211> LENGTH: 9
<212> TYPE: PRT
<213> ORGANISM: Artificial Sequence
<220> FEATURE:
<223> OTHER INFORMATION: CDRL3 of Amatuximab

<400> SEQUENCE: 102

Gln Gln Trp Ser Lys His Pro Leu Thr
1               5

<210> SEQ ID NO 103
<211> LENGTH: 10
<212> TYPE: PRT
<213> ORGANISM: Artificial Sequence
<220> FEATURE:
<223> OTHER INFORMATION: CDRH1 of Amatuximab

<400> SEQUENCE: 103

Gly Tyr Ser Phe Thr Gly Tyr Thr Met Asn
1               5                   10

<210> SEQ ID NO 104
<211> LENGTH: 13
<212> TYPE: PRT
<213> ORGANISM: Artificial Sequence
<220> FEATURE:
<223> OTHER INFORMATION: CDRH2 of Amatuximab

<400> SEQUENCE: 104

Leu Ile Thr Pro Tyr Asn Gly Ala Ser Ser Tyr Asn Gln
1 5 10

<210> SEQ ID NO 105
<211> LENGTH: 10
<212> TYPE: PRT
<213> ORGANISM: Artificial Sequence
<220> FEATURE:
<223> OTHER INFORMATION: CDRH3 of Amatuximab

<400> SEQUENCE: 105

Gly Gly Tyr Asp Gly Arg Gly Phe Asp Tyr
1 5 10

<210> SEQ ID NO 106
<211> LENGTH: 10
<212> TYPE: PRT
<213> ORGANISM: Artificial Sequence
<220> FEATURE:
<223> OTHER INFORMATION: GlySer linker

<400> SEQUENCE: 106

Gly Gly Gly Gly Ser Gly Gly Gly Gly Ser
1 5 10

<210> SEQ ID NO 107
<211> LENGTH: 8
<212> TYPE: PRT
<213> ORGANISM: Artificial Sequence
<220> FEATURE:
<223> OTHER INFORMATION: GlySer linker

<400> SEQUENCE: 107

Gly Gly Gly Ser Gly Gly Gly Ser
1 5

<210> SEQ ID NO 108
<211> LENGTH: 6
<212> TYPE: PRT
<213> ORGANISM: Artificial Sequence
<220> FEATURE:
<223> OTHER INFORMATION: GlySer linker

<400> SEQUENCE: 108

Gly Gly Ser Gly Gly Ser
1 5

<210> SEQ ID NO 109
<211> LENGTH: 11
<212> TYPE: PRT
<213> ORGANISM: Artificial Sequence
<220> FEATURE:
<223> OTHER INFORMATION: GlySer linker

<400> SEQUENCE: 109

Gly Gly Ser Gly Gly Gly Ser Gly Gly Ser Gly
1 5 10

```
<210> SEQ ID NO 110
<211> LENGTH: 10
<212> TYPE: PRT
<213> ORGANISM: Artificial Sequence
<220> FEATURE:
<223> OTHER INFORMATION: GlySer linker

<400> SEQUENCE: 110

Gly Gly Ser Gly Gly Gly Ser Gly Ser Gly
1               5                   10


<210> SEQ ID NO 111
<211> LENGTH: 8
<212> TYPE: PRT
<213> ORGANISM: Artificial Sequence
<220> FEATURE:
<223> OTHER INFORMATION: GlySer linker

<400> SEQUENCE: 111

Gly Gly Ser Gly Gly Gly Ser Gly
1               5


<210> SEQ ID NO 112
<211> LENGTH: 5
<212> TYPE: PRT
<213> ORGANISM: Artificial Sequence
<220> FEATURE:
<223> OTHER INFORMATION: Spacer
<220> FEATURE:
<221> NAME/KEY: MISC_FEATURE
<222> LOCATION: (1)..(5)
<223> OTHER INFORMATION: (GluAlaAlaAlaLys) can be repeated n times,
      wherein n is an integer including 1, 2, 3, 4, 5, 6, 7, 8, 9, or
      more.

<400> SEQUENCE: 112

Glu Ala Ala Ala Lys
1               5


<210> SEQ ID NO 113
<211> LENGTH: 6
<212> TYPE: PRT
<213> ORGANISM: Artificial Sequence
<220> FEATURE:
<223> OTHER INFORMATION: His tag

<400> SEQUENCE: 113

His His His His His His
1               5


<210> SEQ ID NO 114
<211> LENGTH: 8
<212> TYPE: PRT
<213> ORGANISM: Artificial Sequence
<220> FEATURE:
<223> OTHER INFORMATION: Flag tag

<400> SEQUENCE: 114

Asp Tyr Lys Asp Asp Asp Asp Lys
1               5


<210> SEQ ID NO 115
<211> LENGTH: 8
<212> TYPE: PRT
<213> ORGANISM: Artificial Sequence
<220> FEATURE:
<223> OTHER INFORMATION: Xpress tag

<400> SEQUENCE: 115
```

```
Asp Leu Tyr Asp Asp Asp Asp Lys
1               5


<210> SEQ ID NO 116
<211> LENGTH: 15
<212> TYPE: PRT
<213> ORGANISM: Artificial Sequence
<220> FEATURE:
<223> OTHER INFORMATION: Avi tag

<400> SEQUENCE: 116

Gly Leu Asn Asp Ile Phe Glu Ala Gln Lys Ile Glu Trp His Glu
1               5                   10                  15


<210> SEQ ID NO 117
<211> LENGTH: 26
<212> TYPE: PRT
<213> ORGANISM: Artificial Sequence
<220> FEATURE:
<223> OTHER INFORMATION: Calmodulin tag

<400> SEQUENCE: 117

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25


<210> SEQ ID NO 118
<211> LENGTH: 9
<212> TYPE: PRT
<213> ORGANISM: Artificial Sequence
<220> FEATURE:
<223> OTHER INFORMATION: HA tag

<400> SEQUENCE: 118

Tyr Pro Tyr Asp Val Pro Asp Tyr Ala
1               5


<210> SEQ ID NO 119
<211> LENGTH: 10
<212> TYPE: PRT
<213> ORGANISM: Artificial Sequence
<220> FEATURE:
<223> OTHER INFORMATION: Myc tag

<400> SEQUENCE: 119

Glu Gln Lys Leu Ile Ser Glu Glu Asp Leu
1               5                   10


<210> SEQ ID NO 120
<211> LENGTH: 8
<212> TYPE: PRT
<213> ORGANISM: Artificial Sequence
<220> FEATURE:
<223> OTHER INFORMATION: Strep tag

<400> SEQUENCE: 120

Trp Arg His Pro Gln Phe Gly Gly
1               5


<210> SEQ ID NO 121
<211> LENGTH: 8
<212> TYPE: PRT
<213> ORGANISM: Artificial Sequence
<220> FEATURE:
<223> OTHER INFORMATION: STREP tag II
```

<400> SEQUENCE: 121

Trp Ser His Pro Gln Phe Glu Lys
1 5

<210> SEQ ID NO 122
<211> LENGTH: 13
<212> TYPE: PRT
<213> ORGANISM: Artificial Sequence
<220> FEATURE:
<223> OTHER INFORMATION: Softag 1

<400> SEQUENCE: 122

Ser Leu Ala Glu Leu Leu Asn Ala Gly Leu Gly Gly Ser
1 5 10

<210> SEQ ID NO 123
<211> LENGTH: 8
<212> TYPE: PRT
<213> ORGANISM: Artificial Sequence
<220> FEATURE:
<223> OTHER INFORMATION: Softag 3

<400> SEQUENCE: 123

Thr Gln Asp Pro Ser Arg Val Gly
1 5

<210> SEQ ID NO 124
<211> LENGTH: 14
<212> TYPE: PRT
<213> ORGANISM: Artificial Sequence
<220> FEATURE:
<223> OTHER INFORMATION: V5 tag

<400> SEQUENCE: 124

Gly Lys Pro Ile Pro Asn Pro Leu Leu Gly Leu Asp Ser Thr
1 5 10

<210> SEQ ID NO 125
<211> LENGTH: 230
<212> TYPE: PRT
<213> ORGANISM: Artificial Sequence
<220> FEATURE:
<223> OTHER INFORMATION: IgG4 Hinge

<400> SEQUENCE: 125

Glu Ser Lys Tyr Gly Pro Pro Cys Pro Pro Cys Pro Ala Pro Glu Phe
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

-continued

```
Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
225                 230


<210> SEQ ID NO 126
<211> LENGTH: 690
<212> TYPE: DNA
<213> ORGANISM: Artificial Sequence
<220> FEATURE:
<223> OTHER INFORMATION: IgG4 Hinge coding sequence

<400> SEQUENCE: 126

gagagcaagt acggccctcc ctgcccccct tgccctgccc ccgagttcct gggcggaccc      60

agcgtgttcc tgttcccccc caagcccaag gacaccctga tgatcagccg gacccccgag     120

gtgacctgtg tggtggtgga cgtgtcccag gaggaccccg aggtccagtt caactggtac     180

gtggacggcg tggaggtgca caacgccaag accaagcccc gggaggagca gttcaatagc     240

acctaccggg tggtgtccgt gctgaccgtg ctgcaccagg actggctgaa cggcaaggaa     300

tacaagtgta aggtgtccaa caagggcctg cccagcagca tcgagaaaac catcagcaag     360

gccaagggcc agcctcggga gccccaggtg tacaccctgc cccctagcca agaggagatg     420

accaagaacc aggtgtccct gacctgcctg gtgaagggct tctaccccag cgacatcgcc     480

gtggagtggg agagcaacgg ccagcccgag aacaactaca agaccacccc ccctgtgctg     540

gacagcgacg gcagcttctt cctgtacagc cggctgaccg tggacaagag ccggtggcag     600

gagggcaacg tctttagctg ctccgtgatg cacgaggccc tgcacaacca ctacacccag     660

aagagcctga gcctgtccct gggcaagatg                                      690


<210> SEQ ID NO 127
<211> LENGTH: 282
<212> TYPE: PRT
<213> ORGANISM: Artificial Sequence
<220> FEATURE:
<223> OTHER INFORMATION: IgD Hinge

<400> SEQUENCE: 127

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80
```

```
Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280
```

<210> SEQ ID NO 128
<211> LENGTH: 847
<212> TYPE: DNA
<213> ORGANISM: Artificial Sequence
<220> FEATURE:
<223> OTHER INFORMATION: IgD Hinge coding sequence

<400> SEQUENCE: 128

```
aggtggcccg aaagtcccaa ggcccaggca tctagtgttc ctactgcaca gccccaggca     60

gaaggcagcc tagccaaagc tactactgca cctgccacta cgcgcaatac tggccgtggc    120

ggggaggaga agaaaaagga gaaagagaaa gaagaacagg aagagaggga gaccaagacc    180

cctgaatgtc catcccatac ccagccgctg ggcgtctatc tcttgactcc cgcagtacag    240

gacttgtggc ttagagataa ggccaccttt acatgtttcg tcgtgggctc tgacctgaag    300

gatgcccatt tgacttggga ggttgccgga aaggtaccca caggggggt tgaggaaggg    360

ttgctggagc gccattccaa tggctctcag agccagcact caagactcac ccttccgaga    420

tccctgtgga acgccgggac ctctgtcaca tgtactctaa atcatcctag cctgccccca    480

cagcgtctga tggcccttag agagccagcc gcccaggcac cagttaagct tagcctgaat    540

ctgctcgcca gtagtgatcc cccagaggcc gccagctggc tcttatgcga agtgtccggc    600

tttagcccgc ccaacatctt gctcatgtgg ctggaggacc agcgagaagt gaacaccagc    660

ggcttcgctc cagcccggcc cccaccccag ccgggttcta ccacattctg ggcctggagt    720

gtcttaaggg tcccagcacc acctagcccc cagccagcca catacacctg tgttgtgtcc    780

catgaagata gcaggaccct gctaaatgct tctaggagtc tggaggtttc ctacgtgact    840

gaccatt                                                              847
```

<210> SEQ ID NO 129
<211> LENGTH: 12
<212> TYPE: PRT
<213> ORGANISM: Artificial Sequence
<220> FEATURE:
<223> OTHER INFORMATION: IgG4 linker

<400> SEQUENCE: 129

Glu Ser Lys Tyr Gly Pro Pro Cys Pro Pro Cys Pro
1 5 10

<210> SEQ ID NO 130
<211> LENGTH: 35
<212> TYPE: DNA
<213> ORGANISM: Artificial Sequence
<220> FEATURE:
<223> OTHER INFORMATION: Short spacer

<400> SEQUENCE: 130
aatctaagta cggaccgccc tgcccccctt gccct 35

<210> SEQ ID NO 131
<211> LENGTH: 119
<212> TYPE: PRT
<213> ORGANISM: Artificial Sequence
<220> FEATURE:
<223> OTHER INFORMATION: Intermediate spacer

<400> SEQUENCE: 131

Glu Ser Lys Tyr Gly Pro Pro Cys Pro Pro Cys Pro Gly Gln Pro Arg
1 5 10 15

Glu Pro Gln Val Tyr Thr Leu Pro Pro Ser Gln Glu Glu Met Thr Lys
20 25 30

Asn Gln Val Ser Leu Thr Cys Leu Val Lys Gly Phe Tyr Pro Ser Asp
35 40 45

Ile Ala Val Glu Trp Glu Ser Asn Gly Gln Pro Glu Asn Asn Tyr Lys
50 55 60

Thr Thr Pro Pro Val Leu Asp Ser Asp Gly Ser Phe Phe Leu Tyr Ser
65 70 75 80

Arg Leu Thr Val Asp Lys Ser Arg Trp Gln Glu Gly Asn Val Phe Ser
85 90 95

Cys Ser Val Met His Glu Ala Leu His Asn His Tyr Thr Gln Lys Ser
100 105 110

Leu Ser Leu Ser Leu Gly Lys
115

<210> SEQ ID NO 132
<211> LENGTH: 229
<212> TYPE: PRT
<213> ORGANISM: Artificial Sequence
<220> FEATURE:
<223> OTHER INFORMATION: IgG4 hinge region, CH2 region, and CH3 region

<400> SEQUENCE: 132

Glu Ser Lys Tyr Gly Pro Pro Cys Pro Pro Cys Pro Ala Pro Glu Phe
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

```
Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 133
<211> LENGTH: 81
<212> TYPE: DNA
<213> ORGANISM: Artificial Sequence
<220> FEATURE:
<223> OTHER INFORMATION: CD28 transmembrane domain encoding sequence

<400> SEQUENCE: 133

atgttctggg tgctggtggt ggtgggcggg gtgctggcct gctacagcct gctggtgaca     60

gtggccttca tcatcttttg g                                               81


<210> SEQ ID NO 134
<211> LENGTH: 81
<212> TYPE: DNA
<213> ORGANISM: Artificial Sequence
<220> FEATURE:
<223> OTHER INFORMATION: CD28 transmembrane domain encoding sequence

<400> SEQUENCE: 134

atgttctggg tgctggtggt ggtcggaggc gtgctggcct gctacagcct gctggtcacc     60

gtggccttca tcatcttttg g                                               81


<210> SEQ ID NO 135
<211> LENGTH: 81
<212> TYPE: DNA
<213> ORGANISM: Artificial Sequence
<220> FEATURE:
<223> OTHER INFORMATION: CD28 transmembrane domain encoding sequence

<400> SEQUENCE: 135

atgttttggg tgctggtggt ggtgggcggc gtgctggcgt gctatagcct gctggtgacc     60

gtggcgttta ttattttttg g                                               81
```

<210> SEQ ID NO 136
<211> LENGTH: 75
<212> TYPE: DNA
<213> ORGANISM: Artificial Sequence
<220> FEATURE:
<223> OTHER INFORMATION: CD28 transmembrane domain encoding sequence

<400> SEQUENCE: 136
ttttgggtgc tggtggtggt gggcggcgtg ctggcgtgct atagcctgct ggtgaccgtg 60
gcgtttatta ttttt 75

<210> SEQ ID NO 137
<211> LENGTH: 27
<212> TYPE: PRT
<213> ORGANISM: Artificial Sequence
<220> FEATURE:
<223> OTHER INFORMATION: CD28 transmembrane domain

<400> SEQUENCE: 137

Met Phe Trp Val Leu Val Val Val Gly Gly Val Leu Ala Cys Tyr Ser
1 5 10 15

Leu Leu Val Thr Val Ala Phe Ile Ile Phe Trp
20 25

<210> SEQ ID NO 138
<211> LENGTH: 26
<212> TYPE: PRT
<213> ORGANISM: Artificial Sequence
<220> FEATURE:
<223> OTHER INFORMATION: CD28 transmembrane domain

<400> SEQUENCE: 138

Phe Trp Val Leu Val Val Val Gly Gly Val Leu Ala Cys Tyr Ser Leu
1 5 10 15

Leu Val Thr Val Ala Phe Ile Ile Phe Trp
20 25

<210> SEQ ID NO 139
<211> LENGTH: 336
<212> TYPE: DNA
<213> ORGANISM: Artificial Sequence
<220> FEATURE:
<223> OTHER INFORMATION: CD3z encoding sequence

<400> SEQUENCE: 139
cgggtgaagt tcagcagaag cgccgacgcc cctgcctacc agcagggcca gaatcagctg 60
tacaacgagc tgaacctggg cagaagggaa gagtacgacg tcctggataa gcggagaggc 120
cgggaccctg agatgggcgg caagcctcgg cggaagaacc cccaggaagg cctgtataac 180
gaactgcaga aagacaagat ggccgaggcc tacagcgaga tcggcatgaa gggcgagcgg 240
aggcggggca agggccacga cggcctgtat cagggcctgt ccaccgccac caaggatacc 300
tacgacgccc tgcacatgca ggccctgccc ccaagg 336

<210> SEQ ID NO 140
<211> LENGTH: 336
<212> TYPE: DNA
<213> ORGANISM: Artificial Sequence
<220> FEATURE:
<223> OTHER INFORMATION: CD3z encoding sequence

<400> SEQUENCE: 140
cgcgtgaaat ttagccgcag cgcggatgcg ccggcgtatc agcagggcca gaaccagctg 60
tataacgaac tgaacctggg ccgccgcgaa gaatatgatg tgctggataa acgccgcggc 120
cgcgatccgg aaatgggcgg caaaccgcgc cgcaaaaacc cgcaggaagg cctgtataac 180
gaactgcaga aagataaaat ggcggaagcg tatagcgaaa ttggcatgaa aggcgaacgc 240
cgccgcggca aaggccatga tggcctgtat cagggcctga gcaccgcgac caaagatacc 300
tatgatgcgc tgcatatgca ggcgctgccg ccgcgc 336

<210> SEQ ID NO 141
<211> LENGTH: 342
<212> TYPE: DNA
<213> ORGANISM: Artificial Sequence
<220> FEATURE:
<223> OTHER INFORMATION: CD3z encoding sequence

<400> SEQUENCE: 141
gaactgcgcg tgaaatttag ccgcagcgcg gatgcgccgg cgtatcagca gggccagaac 60
cagctgtata acgaactgaa cctgggccgc cgcgaagaat atgatgtgct ggataaacgc 120
cgcggccgcg atccggaaat gggcggcaaa ccgcgccgca aaaacccgca ggaaggcctg 180
tataacgaac tgcagaaaga taaaatggcg gaagcgtata gcgaaattgg catgaaaggc 240
gaacgccgcc gcggcaaagg ccatgatggc ctgtatcagg gcctgagcac cgcgaccaaa 300
gatacctatg atgcgctgca tatgcaggcg ctgccgccgc gc 342

<210> SEQ ID NO 142
<211> LENGTH: 112
<212> TYPE: PRT
<213> ORGANISM: Artificial Sequence
<220> FEATURE:
<223> OTHER INFORMATION: CD3z

<400> SEQUENCE: 142

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 143
<211> LENGTH: 114
<212> TYPE: PRT
<213> ORGANISM: Artificial Sequence
<220> FEATURE:
<223> OTHER INFORMATION: CD3z

<400> SEQUENCE: 143

Glu Leu Arg Val Lys Phe Ser Arg Ser Ala Asp Ala Pro Ala Tyr Gln
1 5 10 15

Gln Gly Gln Asn Gln Leu Tyr Asn Glu Leu Asn Leu Gly Arg Arg Glu
20 25 30

```
Glu Tyr Asp Val Leu Asp Lys Arg Arg Gly Arg Asp Pro Glu Met Gly
        35                  40                  45

Gly Lys Pro Arg Arg Lys Asn Pro Gln Glu Gly Leu Tyr Asn Glu Leu
    50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Tyr Gln Gly Leu Ser
                85                  90                  95

Thr Ala Thr Lys Asp Thr Tyr Asp Ala Leu His Met Gln Ala Leu Pro
            100                 105                 110

Pro Arg


<210> SEQ ID NO 144
<211> LENGTH: 129
<212> TYPE: DNA
<213> ORGANISM: Artificial Sequence
<220> FEATURE:
<223> OTHER INFORMATION: 4-1BB encoding sequence

<400> SEQUENCE: 144

gtgaaacggg gcagaaagaa actcctgtat atattcaaac aaccatttat gagaccagta     60

caaactactc aagaggaaga tggctgtagc tgccgatttc cagaagaaga agaaggagga    120

tgtgaactg                                                            129


<210> SEQ ID NO 145
<211> LENGTH: 129
<212> TYPE: DNA
<213> ORGANISM: Artificial Sequence
<220> FEATURE:
<223> OTHER INFORMATION: 4-1BB encoding sequence

<400> SEQUENCE: 145

gtgaaacgcg gccgcaaaaa actgctgtat atttttaaac agccgtttat gcgcccggtg     60

cagaccaccc aggaagaaga tggctgcagc tgccgctttc cggaagaaga agaaggcggc    120

tgcgaactg                                                            129


<210> SEQ ID NO 146
<211> LENGTH: 123
<212> TYPE: DNA
<213> ORGANISM: Artificial Sequence
<220> FEATURE:
<223> OTHER INFORMATION: 4-1BB encoding sequence

<400> SEQUENCE: 146

gtgaaacgcg gccgcaaaaa actgctgtat atttttaaac agccgtttat gcgcccggtg     60

cagaccaccc aggaagaaga tggctgcagc tgccgctttc cggaagaaga agaaggcggc    120

tgc                                                                  123


<210> SEQ ID NO 147
<211> LENGTH: 43
<212> TYPE: PRT
<213> ORGANISM: Artificial Sequence
<220> FEATURE:
<223> OTHER INFORMATION: 4-1BB

<400> SEQUENCE: 147

Val Lys Arg Gly Arg Lys Lys Leu Leu Tyr Ile Phe Lys Gln Pro Phe
1               5                   10                  15

Met Arg Pro Val Gln Thr Thr Gln Glu Glu Asp Gly Cys Ser Cys Arg
```

```
            20                  25                  30

Phe Pro Glu Glu Glu Glu Gly Gly Cys Glu Leu
        35                  40


<210> SEQ ID NO 148
<211> LENGTH: 41
<212> TYPE: PRT
<213> ORGANISM: Artificial Sequence
<220> FEATURE:
<223> OTHER INFORMATION: 4-1BB_CPD

<400> SEQUENCE: 148

Val Lys Arg Gly Arg Lys Lys Leu Leu Tyr Ile Phe Lys Gln Pro Phe
1               5                   10                  15

Met Arg Pro Val Gln Thr Thr Gln Glu Glu Asp Gly Cys Ser Cys Arg
            20                  25                  30

Phe Pro Glu Glu Glu Glu Gly Gly Cys
        35                  40


<210> SEQ ID NO 149
<211> LENGTH: 21
<212> TYPE: PRT
<213> ORGANISM: Artificial Sequence
<220> FEATURE:
<223> OTHER INFORMATION: Thosea asigna virus 2A (T2A) peptide
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 149

Gly Ser Gly Glu Gly Arg Gly Ser Leu Leu Thr Cys Gly Asp Val Glu
1               5                   10                  15

Glu Asn Pro Gly Pro
            20


<210> SEQ ID NO 150
<211> LENGTH: 22
<212> TYPE: PRT
<213> ORGANISM: Artificial Sequence
<220> FEATURE:
<223> OTHER INFORMATION: Porcine teschovirus-1 2A (P2A) peptide
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 150

Gly Ser Gly Ala Thr Asn Phe Ser Leu Leu Lys Gln Ala Gly Asp Val
1               5                   10                  15

Glu Glu Asn Pro Gly Pro
            20


<210> SEQ ID NO 151
<211> LENGTH: 23
<212> TYPE: PRT
<213> ORGANISM: Artificial Sequence
<220> FEATURE:
<223> OTHER INFORMATION: Equine rhinitis A virus (ERAV) 2A (E2A) peptide
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency
```

<400> SEQUENCE: 151

Gly Ser Gly Gln Cys Thr Asn Tyr Ala Leu Leu Lys Leu Ala Gly Asp
1 5 10 15

Val Glu Ser Asn Pro Gly Pro
20

<210> SEQ ID NO 152
<211> LENGTH: 25
<212> TYPE: PRT
<213> ORGANISM: Artificial Sequence
<220> FEATURE:
<223> OTHER INFORMATION: Foot-and-mouth disease virus 2A (F2A) peptide
<220> FEATURE:
<221> NAME/KEY: MISC_FEATURE
<222> LOCATION: (1)..(3)
<223> OTHER INFORMATION: (GlySerGly) residues can be added to the 5' end of the peptide to improve cleavage efficiency

<400> SEQUENCE: 152

Gly Ser Gly Val Lys Gln Thr Leu Asn Phe Asp Leu Leu Lys Leu Ala
1 5 10 15

Gly Asp Val Glu Ser Asn Pro Gly Pro
20 25

<210> SEQ ID NO 153
<211> LENGTH: 19
<212> TYPE: PRT
<213> ORGANISM: Artificial Sequence
<220> FEATURE:
<223> OTHER INFORMATION: Variant of T2A

<400> SEQUENCE: 153

Gly Glu Gly Arg Gly Ser Leu Leu Thr Cys Gly Asp Val Glu Glu Asn
1 5 10 15

Pro Gly Pro

<210> SEQ ID NO 154
<211> LENGTH: 21
<212> TYPE: PRT
<213> ORGANISM: Artificial Sequence
<220> FEATURE:
<223> OTHER INFORMATION: Variant of T2A

<400> SEQUENCE: 154

Gly Gly Gly Glu Gly Arg Gly Ser Leu Leu Thr Cys Gly Asp Val Glu
1 5 10 15

Glu Asn Pro Gly Pro
20

<210> SEQ ID NO 155
<211> LENGTH: 335
<212> TYPE: PRT
<213> ORGANISM: Artificial Sequence
<220> FEATURE:
<223> OTHER INFORMATION: EGFRt

<400> SEQUENCE: 155

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

-continued

```
Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335


<210> SEQ ID NO 156
<211> LENGTH: 312
<212> TYPE: PRT
<213> ORGANISM: Artificial Sequence
<220> FEATURE:
<223> OTHER INFORMATION: EGFR

<400> SEQUENCE: 156

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80
```

```
Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser
305                 310
```

<210> SEQ ID NO 157
<211> LENGTH: 23
<212> TYPE: PRT
<213> ORGANISM: Artificial Sequence
<220> FEATURE:
<223> OTHER INFORMATION: TM_EGFR

<400> SEQUENCE: 157

```
Ile Ala Thr Gly Met Val Gly Ala Leu Leu Leu Leu Leu Val Val Ala
1               5                   10                  15

Leu Gly Ile Gly Leu Phe Met
            20
```

<210> SEQ ID NO 158
<211> LENGTH: 783
<212> TYPE: DNA
<213> ORGANISM: Artificial Sequence
<220> FEATURE:
<223> OTHER INFORMATION: 1H7 scFv coding sequence

<400> SEQUENCE: 158

```
atgctgctgc tcgtgaccag cctgctgctg tgcgaactgc cccaccctgc ctttctgctg      60

atcccccaag tacaacttca acaaagtgga gccgaactgg taaaacccgg agcgtctgtg     120

aagattagtt gcaaggcatc cggttacgcc ttctcaaatt attggatgaa ctgggtaaag     180

cagcggcccg gaaagggtct cgagtggatt gggcaaatca acccagggga cggggatacg     240
```

-continued

```
aactacaacg gtaagttcaa aggcaaggct acgttgacgg ctgataagag ctcaagcacc    300

gcttacatgc agttgtcttc tttgacaagt gaggatagtg ccgtttactt ctgcgcccga    360

gaggaccgag attattttga ttattggggc cagggaacaa ctctcaccgt cagctccgga    420

ggcggaggat ctggcggagg gggctctgga ggaggaggat ctgatattca gatgacccaa    480

actacgagtt ccctgtctgc cagccttggc gaccgggtca caattagttg cagggcttct    540

caggatatca actactattt gaactggtac cagcagaaac ctgatgggac ggtcaaactt    600

ctcatctact attcatccag actgcacagt ggcgtaccgt ctagattctc aggaagcggc    660

agtggtacgg attttagtct taccattagt aatctggaac aggaggacat cgccacgtat    720

ttttgccagc aggatgacgc actgccctat accttcggcg gaggcactaa gttggagata    780

aaa                                                                  783
```

<210> SEQ ID NO 159
<211> LENGTH: 735
<212> TYPE: DNA
<213> ORGANISM: Artificial Sequence
<220> FEATURE:
<223> OTHER INFORMATION: anti-CD19 scFv coding sequence

<400> SEQUENCE: 159

```
gacatccaga tgacccagac cacctccagc ctgagcgcca gcctgggcga ccgggtgacc     60

atcagctgcc gggccagcca ggacatcagc aagtacctga actggtatca gcagaagccc    120

gacggcaccg tcaagctgct gatctaccac accagccggc tgcacagcgg cgtgcccagc    180

cggtttagcg gcagcggctc cggcaccgac tacagcctga ccatctccaa cctggaacag    240

gaagatatcg ccacctactt ttgccagcag ggcaacacac tgccctacac ctttggcggc    300

ggaacaaagc tggaaatcac cggcagcacc tccggcagcg gcaagcctgg cagcggcgag    360

ggcagcacca agggcgaggt gaagctgcag gaaagcggcc ctggcctggt ggcccccagc    420

cagagcctga gcgtgacctg caccgtgagc ggcgtgagcc tgcccgacta cggcgtgagc    480

tggatccggc agcccccag gaagggcctg gaatggctgg gcgtgatctg gggcagcgag    540

accacctact acaacagcgc cctgaagagc cggctgacca tcatcaagga caacagcaag    600

agccaggtgt tcctgaagat gaacagcctg cagaccgacg acaccgccat ctactactgc    660

gccaagcact actactacgg cggcagctac gccatggact actggggcca gggcaccagc    720

gtgaccgtga gcagc                                                     735
```

<210> SEQ ID NO 160
<211> LENGTH: 249
<212> TYPE: PRT
<213> ORGANISM: Homo sapiens

<400> SEQUENCE: 160

```
Met Ala Ala Arg Arg Ser Gln Arg Arg Arg Gly Arg Arg Gly Glu Pro
1               5                   10                  15

Gly Thr Ala Leu Leu Val Pro Leu Ala Leu Gly Leu Gly Leu Ala Leu
            20                  25                  30

Ala Cys Leu Gly Leu Leu Leu Ala Val Val Ser Leu Gly Ser Arg Ala
        35                  40                  45

Ser Leu Ser Ala Gln Glu Pro Ala Gln Glu Glu Leu Val Ala Glu Glu
    50                  55                  60

Asp Gln Asp Pro Ser Glu Leu Asn Pro Gln Thr Glu Glu Ser Gln Asp
65                  70                  75                  80
```

-continued

```
Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
            100                 105                 110

Val His Pro Arg Pro Gly Gln Asp Gly Ala Gln Ala Gly Val Asp Gly
        115                 120                 125

Thr Val Ser Gly Trp Glu Glu Ala Arg Ile Asn Ser Ser Ser Pro Leu
    130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
            180                 185                 190

Glu Glu Phe Ser Ala Thr Ala Ala Ser Ser Leu Gly Pro Gln Leu Arg
        195                 200                 205

Leu Cys Gln Val Ser Gly Leu Leu Ala Leu Arg Pro Gly Ser Ser Leu
    210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245


<210> SEQ ID NO 161
<211> LENGTH: 416
<212> TYPE: PRT
<213> ORGANISM: Homo sapiens

<400> SEQUENCE: 161

Met Pro Arg Gln Leu Ser Ala Ala Ala Ala Leu Phe Ala Ser Leu Ala
1               5                   10                  15

Val Ile Leu His Asp Gly Ser Gln Met Arg Ala Lys Ala Phe Pro Glu
            20                  25                  30

Thr Arg Asp Tyr Ser Gln Pro Thr Ala Ala Ala Thr Val Gln Asp Ile
        35                  40                  45

Lys Lys Pro Val Gln Gln Pro Ala Lys Gln Ala Pro His Gln Thr Leu
    50                  55                  60

Ala Ala Arg Phe Met Asp Gly His Ile Thr Phe Gln Thr Ala Ala Thr
65                  70                  75                  80

Val Lys Ile Pro Thr Thr Thr Pro Ala Thr Thr Lys Asn Thr Ala Thr
                85                  90                  95

Thr Ser Pro Ile Thr Tyr Thr Leu Val Thr Thr Gln Ala Thr Pro Asn
            100                 105                 110

Asn Ser His Thr Ala Pro Pro Val Thr Glu Val Thr Val Gly Pro Ser
        115                 120                 125

Leu Ala Pro Tyr Ser Leu Pro Pro Thr Ile Thr Pro Pro Ala His Thr
    130                 135                 140

Thr Gly Thr Ser Ser Ser Thr Val Ser His Thr Thr Gly Asn Thr Thr
145                 150                 155                 160

Gln Pro Ser Asn Gln Thr Thr Leu Pro Ala Thr Leu Ser Ile Ala Leu
                165                 170                 175

His Lys Ser Thr Thr Gly Gln Lys Pro Val Gln Pro Thr His Ala Pro
            180                 185                 190

Gly Thr Thr Ala Ala Ala His Asn Thr Thr Arg Thr Ala Ala Pro Ala
        195                 200                 205
```

```
Ser Thr Val Pro Gly Pro Thr Leu Ala Pro Gln Pro Ser Ser Val Lys
    210                 215                 220

Thr Gly Ile Tyr Gln Val Leu Asn Gly Ser Arg Leu Cys Ile Lys Ala
225                 230                 235                 240

Glu Met Gly Ile Gln Leu Ile Val Gln Asp Lys Glu Ser Val Phe Ser
                245                 250                 255

Pro Arg Arg Tyr Phe Asn Ile Asp Pro Asn Ala Thr Gln Ala Ser Gly
            260                 265                 270

Asn Cys Gly Thr Arg Lys Ser Asn Leu Leu Leu Asn Phe Gln Gly Gly
        275                 280                 285

Phe Val Asn Leu Thr Phe Thr Lys Asp Glu Glu Ser Tyr Tyr Ile Ser
    290                 295                 300

Glu Val Gly Ala Tyr Leu Thr Val Ser Asp Pro Glu Thr Ile Tyr Gln
305                 310                 315                 320

Gly Ile Lys His Ala Val Val Met Phe Gln Thr Ala Val Gly His Ser
                325                 330                 335

Phe Lys Cys Val Ser Glu Gln Ser Leu Gln Leu Ser Ala His Leu Gln
            340                 345                 350

Val Lys Thr Thr Asp Val Gln Leu Gln Ala Phe Asp Phe Glu Asp Asp
        355                 360                 365

His Phe Gly Asn Val Asp Glu Cys Ser Ser Asp Tyr Thr Ile Val Leu
    370                 375                 380

Pro Val Ile Gly Ala Ile Val Val Gly Leu Cys Leu Met Gly Met Gly
385                 390                 395                 400

Val Tyr Lys Ile Arg Leu Arg Cys Gln Ser Ser Gly Tyr Gln Arg Ile
                405                 410                 415


<210> SEQ ID NO 162
<211> LENGTH: 281
<212> TYPE: PRT
<213> ORGANISM: Homo sapiens

<400> SEQUENCE: 162

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
```

```
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280


<210> SEQ ID NO 163
<211> LENGTH: 6
<212> TYPE: PRT
<213> ORGANISM: Artificial Sequence
<220> FEATURE:
<223> OTHER INFORMATION: CDRL1 of 1H7 (IMGT)

<400> SEQUENCE: 163

Gln Asp Ile Asn Tyr Tyr
1               5


<210> SEQ ID NO 164
<211> LENGTH: 8
<212> TYPE: PRT
<213> ORGANISM: Artificial Sequence
<220> FEATURE:
<223> OTHER INFORMATION: CDRH1 of 1H7 (IMGT)

<400> SEQUENCE: 164

Gly Tyr Ala Phe Ser Asn Tyr Trp
1               5


<210> SEQ ID NO 165
<211> LENGTH: 8
<212> TYPE: PRT
<213> ORGANISM: Artificial Sequence
<220> FEATURE:
<223> OTHER INFORMATION: CDRH2 of 1H7 (IMGT)

<400> SEQUENCE: 165

Ile Asn Pro Gly Asp Gly Asp Thr
1               5


<210> SEQ ID NO 166
<211> LENGTH: 7
<212> TYPE: PRT
<213> ORGANISM: Artificial Sequence
<220> FEATURE:
<223> OTHER INFORMATION: CDRL2 of 1H7 (Kabat and Chothia)

<400> SEQUENCE: 166

Tyr Ser Ser Arg Leu His Ser
1               5


<210> SEQ ID NO 167
<211> LENGTH: 5
<212> TYPE: PRT
```

-continued

<213> ORGANISM: Artificial Sequence
<220> FEATURE:
<223> OTHER INFORMATION: CDRH1 of 1H7 (Kabat)

<400> SEQUENCE: 167

Asn Tyr Trp Met Asn
1 5

<210> SEQ ID NO 168
<211> LENGTH: 17
<212> TYPE: PRT
<213> ORGANISM: Artificial Sequence
<220> FEATURE:
<223> OTHER INFORMATION: CDRH2 of 1H7 (Kabat)

<400> SEQUENCE: 168

Gln Ile Asn Pro Gly Asp Gly Asp Thr Asn Tyr Asn Gly Lys Phe Lys
1 5 10 15

Gly

<210> SEQ ID NO 169
<211> LENGTH: 8
<212> TYPE: PRT
<213> ORGANISM: Artificial Sequence
<220> FEATURE:
<223> OTHER INFORMATION: CDRH3 of 1H7 (Kabat and Chothia)

<400> SEQUENCE: 169

Glu Asp Arg Asp Tyr Phe Asp Tyr
1 5

<210> SEQ ID NO 170
<211> LENGTH: 7
<212> TYPE: PRT
<213> ORGANISM: Artificial Sequence
<220> FEATURE:
<223> OTHER INFORMATION: CDRH1 of 1H7 (Chothia)

<400> SEQUENCE: 170

Gly Tyr Ala Phe Ser Asn Tyr
1 5

<210> SEQ ID NO 171
<211> LENGTH: 6
<212> TYPE: PRT
<213> ORGANISM: Artificial Sequence
<220> FEATURE:
<223> OTHER INFORMATION: CDRH2 of 1H7 (Chothia)

<400> SEQUENCE: 171

Asn Pro Gly Asp Gly Asp
1 5

<210> SEQ ID NO 172
<211> LENGTH: 109
<212> TYPE: PRT
<213> ORGANISM: Artificial Sequence
<220> FEATURE:
<223> OTHER INFORMATION: C-type lectin

<400> SEQUENCE: 172

His Lys Asp Ser Cys Tyr Phe Leu Ser Asp Asp Val Gln Thr Trp Gln
1 5 10 15

Glu Ser Lys Met Ala Cys Ala Ala Gln Asn Ala Ser Leu Leu Lys Ile
20 25 30

Asn Asn Lys Asn Ala Leu Glu Phe Ile Lys Ser Gln Ser Arg Ser Tyr
35 40 45

Asp Tyr Trp Leu Gly Leu Ser Pro Glu Glu Asp Ser Thr Arg Gly Met
50 55 60

Arg Val Asp Asn Ile Ile Asn Ser Ser Ala Trp Val Ile Arg Asn Ala
65 70 75 80

Pro Asp Leu Asn Asn Met Tyr Cys Gly Tyr Ile Asn Arg Leu Tyr Val
85 90 95

Gln Tyr Tyr His Cys Thr Tyr Lys Lys Arg Met Ile Cys
100 105

<210> SEQ ID NO 173
<211> LENGTH: 60
<212> TYPE: DNA
<213> ORGANISM: Artificial Sequence
<220> FEATURE:
<223> OTHER INFORMATION: linker coding sequence

<400> SEQUENCE: 173
ggaggaggag gcagcggcgg aggaggctcc ggaggcggcg gctctggcgg cggcggcagc 60

<210> SEQ ID NO 174
<211> LENGTH: 245
<212> TYPE: PRT
<213> ORGANISM: Artificial Sequence
<220> FEATURE:
<223> OTHER INFORMATION: anti-CD19 scFv

<400> SEQUENCE: 174

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Ser Thr Ser Gly
100 105 110

Ser Gly Lys Pro Gly Ser Gly Glu Gly Ser Thr Lys Gly Glu Val Lys
115 120 125

Leu Gln Glu Ser Gly Pro Gly Leu Val Ala Pro Ser Gln Ser Leu Ser
130 135 140

Val Thr Cys Thr Val Ser Gly Val Ser Leu Pro Asp Tyr Gly Val Ser
145 150 155 160

Trp Ile Arg Gln Pro Pro Arg Lys Gly Leu Glu Trp Leu Gly Val Ile
165 170 175

Trp Gly Ser Glu Thr Thr Tyr Tyr Asn Ser Ala Leu Lys Ser Arg Leu
180 185 190

Thr Ile Ile Lys Asp Asn Ser Lys Ser Gln Val Phe Leu Lys Met Asn
195 200 205

Ser Leu Gln Thr Asp Asp Thr Ala Ile Tyr Tyr Cys Ala Lys His Tyr
210 215 220

```
Tyr Tyr Gly Gly Ser Tyr Ala Met Asp Tyr Trp Gly Gln Gly Thr Ser
225                 230                 235                 240

Val Thr Val Ser Ser
                245


<210> SEQ ID NO 175
<211> LENGTH: 240
<212> TYPE: PRT
<213> ORGANISM: Homo sapiens

<400> SEQUENCE: 175

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240


<210> SEQ ID NO 176
<211> LENGTH: 3612
<212> TYPE: DNA
<213> ORGANISM: Artificial Sequence
<220> FEATURE:
<223> OTHER INFORMATION: 1H7-long-41bb-3z-T-CD19t Top Strand

<400> SEQUENCE: 176

ggatctgcga tcgctccggt gcccgtcagt gggcagagcg cacatcgccc acagtccccg      60

agaagttggg gggaggggtc ggcaattgaa ccggtgccta gagaaggtgg cgcggggtaa     120

actgggaaag tgatgtcgtg tactggctcc gcctttttcc cgagggtggg ggagaaccgt     180

atataagtgc agtagtcgcc gtgaacgttc tttttcgcaa cgggtttgcc gccagaacac     240

agctgaagct tcgaggggct cgcatctctc cttcacgcgc ccgccgccct acctgaggcc     300
```

-continued

```
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacggctag ccaccatgct gctgctcgtg accagcctgc tgctgtgcga actgccccac    600
cctgcctttc tgctgatccc ccaagtacaa cttcaacaaa gtggagccga actggtaaaa    660
cccggagcgt ctgtgaagat tagttgcaag gcatccggtt acgccttctc aaattattgg    720
atgaactggg taaagcagcg gcccggaaag ggtctcgagt ggattgggca aatcaaccca    780
ggggacgggg atacgaacta caacggtaag ttcaaaggca aggctacgtt gacggctgat    840
aagagctcaa gcaccgctta catgcagttg tcttctttga caagtgagga tagtgccgtt    900
tacttctgcg cccgagagga ccgagattat tttgattatt ggggccaggg aacaactctc    960
accgtcagct ccggaggcgg aggatctggc ggagggggct ctggaggagg aggatctgat   1020
attcagatga cccaaactac gagttccctg tctgccagcc ttggcgaccg ggtcacaatt   1080
agttgcaggg cttctcagga tatcaactac tatttgaact ggtaccagca gaaacctgat   1140
gggacggtca aacttctcat ctactattca tccagactgc acagtggcgt accgtctaga   1200
ttctcaggaa gcggcagtgg tacggatttt agtcttacca ttagtaatct ggaacaggag   1260
gacatcgcca cgtatttttg ccagcaggat gacgcactgc cctatacctt cggcggaggc   1320
actaagttgg agataaaaga gtctaagtac ggaccgcctt gcccaccgtg cccagcacca   1380
cctgtggcag gaccgtcagt cttcctcttc cccccaaaac ccaaggacac cctgatgatc   1440
agccggaccc ccgaggtgac ctgcgtggtg gtggacgtga gccaggaaga tcccgaggtc   1500
cagttcaatt ggtacgtgga cggcgtggaa gtgcacaacg ccaagaccaa gcccagagag   1560
gaacagttcc aaagcaccta ccgggtggtg tctgtgctga ccgtgctgca ccaggactgg   1620
ctgaacggca aagaatacaa gtgcaaggtg tccaacaagg gcctgcccag cagcatcgaa   1680
aagaccatca gcaaggccaa gggccagcct cgcgagcccc aggtgtacac cctgcctccc   1740
tcccaggaag agatgaccaa gaaccaggtg tccctgacct gcctggtgaa gggcttctac   1800
cccagcgaca tcgccgtgga gtgggagagc aacggccagc ctgagaacaa ctacaagacc   1860
acccctcccg tgctggacag cgacggcagc ttcttcctgt acagccggct gaccgtggac   1920
aagagccggt ggcaggaagg caacgtcttt agctgcagcg tgatgcacga ggccctgcac   1980
aaccactaca cccagaagag cctgagcctg tccctgggca agatgttctg ggtgctggtg   2040
gtggtgggcg gggtgctggc ctgctacagc ctgctggtga cagtggcctt catcatcttt   2100
tgggtgaaac ggggcagaaa gaaactcctg tatatattca aacaaccatt tatgagacca   2160
gtacaaacta ctcaagagga agatggctgt agctgccgat ttccagaaga agaagaagga   2220
ggatgtgaac tgcgggtgaa gttcagcaga agcgccgacg cccctgccta ccagcagggc   2280
cagaatcagc tgtacaacga gctgaacctg ggcagaaggg aagagtacga cgtcctggat   2340
aagcggagag gccgggaccc tgagatgggc ggcaagcctc ggcggaagaa cccccaggaa   2400
ggcctgtata acgaactgca gaaagacaag atggccgagg cctacagcga gatcggcatg   2460
aagggcgagc ggaggcgggg caagggccac gacggcctgt atcagggcct gtccaccgcc   2520
accaaggata cctacgacgc cctgcacatg caggccctgc cccccaaggct cgagggcggc   2580
ggagagggca gaggaagtct tctaacatgc ggtgacgtgg aggagaatcc aggccctagg   2640
atgccacctc caagactcct cttcttcctc ctcttcctga caccaatgga agtcaggcct   2700
```

gaggaacctc tagtggtgaa ggtggaagag ggagataacg ctgtgttaca gtgcctcaag 2760
ggaacctcag atggacccac tcagcagctg acctggtctc gggagtctcc gcttaaaccc 2820
ttcctgaaac tcagccttgg actgccaggt ctgggaatcc acatgaggcc actggctatc 2880
tggctgttca tcttcaacgt ctctcaacag atgggaggct tctacctgtg tcagcctgga 2940
ccaccttctg agaaggcatg gcagcctggt tggacagtca atgtggaggg ttctggtgag 3000
ctgttccggt ggaatgtttc ggacctaggt ggactgggat gtggtctgaa gaacaggtcc 3060
tcagagggac ctagctctcc ttccgggaag ctcatgagcc ccaagctgta tgtgtgggcc 3120
aaagaccgcc ctgagatctg ggagggagag cctccgtgtg tcccaccgag ggacagcctg 3180
aaccagagcc tcagccagga cctcaccatg gcccctggct ccacactctg gctgtcctgt 3240
ggggtacccc ctgactctgt gtccaggggc cccctctcct ggacccatgt gcaccccaag 3300
gggcctaagt cattgctgag cctagagctg aaggacgatc gccctgccag agatatgtgg 3360
gtaatggaga cgggtctgtt gttgccccgg gccacagctc aagacgctgg aaagtattat 3420
tgtcaccgtg gcaacctgac catgtcattc cacctggaga tcactgctcg gccagtacta 3480
tggcactggc tgctgaggac tggtggctgg aaggtctcag ctgtgacttt ggcttatctg 3540
atcttctgcc tgtgttccct tgtgggcatt cttcatcttc aaagagccct ggtcctgagg 3600
aggaaaagat ga 3612

<210> SEQ ID NO 177
<211> LENGTH: 2964
<212> TYPE: DNA
<213> ORGANISM: Artificial Sequence
<220> FEATURE:
<223> OTHER INFORMATION: 1H7-sh-41bb-3z-T-CD19t Top Strand

<400> SEQUENCE: 177
ggatctgcga tcgctccggt gcccgtcagt gggcagagcg cacatcgccc acagtccccg 60
agaagttggg gggaggggtc ggcaattgaa ccggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacggctag ccaccatgct gctgctcgtg accagcctgc tgctgtgcga actgccccac 600
cctgcctttc tgctgatccc ccaagtacaa cttcaacaaa gtggagccga actggtaaaa 660
cccggagcgt ctgtgaagat tagttgcaag gcatccggtt acgccttctc aaattattgg 720
atgaactggg taaagcagcg gcccggaaag ggtctcgagt ggattgggca aatcaaccca 780
ggggacgggg atacgaacta caacggtaag ttcaaaggca aggctacgtt gacggctgat 840
aagagctcaa gcaccgctta catgcagttg tcttctttga caagtgagga tagtgccgtt 900
tacttctgcg cccgagagga ccgagattat tttgattatt ggggccaggg aacaactctc 960
accgtcagct ccggaggcgg aggatctggc ggagggggct ctggaggagg aggatctgat 1020
attcagatga cccaaactac gagttccctg tctgccagcc ttggcgaccg ggtcacaatt 1080

```
agttgcaggg cttctcagga tatcaactac tatttgaact ggtaccagca gaaacctgat   1140

gggacggtca aacttctcat ctactattca tccagactgc acagtggcgt accgtctaga   1200

ttctcaggaa gcggcagtgg tacggatttt agtcttacca ttagtaatct ggaacaggag   1260

gacatcgcca cgtatttttg ccagcaggat gacgcactgc cctatacctt cggcggaggc   1320

actaagttgg agataaaaga gtctaagtac ggaccgccct gccccccttg ccctatgttc   1380

tgggtgctgg tggtggtcgg aggcgtgctg gcctgctaca gcctgctggt caccgtggcc   1440

ttcatcatct tttgggtgaa acggggcaga aagaaactcc tgtatatatt caaacaacca   1500

tttatgagac cagtacaaac tactcaagag gaagatggct gtagctgccg atttccagaa   1560

gaagaagaag gaggatgtga actgcgggtg aagttcagca gaagcgccga cgcccctgcc   1620

taccagcagg gccagaatca gctgtacaac gagctgaacc tgggcagaag ggaagagtac   1680

gacgtcctgg ataagcggag aggccgggac cctgagatgg gcggcaagcc tcggcggaag   1740

aacccccagg aaggcctgta taacgaactg cagaaagaca agatggccga ggcctacagc   1800

gagatcggca tgaagggcga gcggaggcgg ggcaagggcc acgacggcct gtatcagggc   1860

ctgtccaccg ccaccaagga tacctacgac gccctgcaca tgcaggccct gcccccaagg   1920

ctcgagggcg gcggagaggg cagaggaagt cttctaacat gcggtgacgt ggaggagaat   1980

ccaggcccta ggatgccacc tccaagactc ctcttcttcc tcctcttcct gacaccaatg   2040

gaagtcaggc ctgaggaacc tctagtggtg aaggtggaag agggagataa cgctgtgtta   2100

cagtgcctca agggaacctc agatggaccc actcagcagc tgacctggtc tcgggagtct   2160

ccgcttaaac ccttcctgaa actcagcctt ggactgccag gtctgggaat ccacatgagg   2220

ccactggcta tctggctgtt catcttcaac gtctctcaac agatgggagg cttctacctg   2280

tgtcagcctg gaccaccttc tgagaaggca tggcagcctg gttggacagt caatgtggag   2340

ggttctggtg agctgttccg gtggaatgtt tcggacctag gtggactggg atgtggtctg   2400

aagaacaggt cctcagaggg acctagctct ccttccggga agctcatgag ccccaagctg   2460

tatgtgtggg ccaaagaccg ccctgagatc tgggagggag agcctccgtg tgtcccaccg   2520

agggacagcc tgaaccagag cctcagccag gacctcacca tggcccctgg ctccacactc   2580

tggctgtcct gtggggtacc ccctgactct gtgtccaggg gccccctctc ctggacccat   2640

gtgcacccca aggggcctaa gtcattgctg agcctagagc tgaaggacga tcgccctgcc   2700

agagatatgt gggtaatgga gacgggtctg ttgttgcccc gggccacagc tcaagacgct   2760

ggaaagtatt attgtcaccg tggcaacctg accatgtcat tccacctgga gatcactgct   2820

cggccagtac tatggcactg gctgctgagg actggtggct ggaaggtctc agctgtgact   2880

ttggcttatc tgatcttctg cctgtgttcc cttgtgggca ttcttcatct tcaaagagcc   2940

ctggtcctga ggaggaaaag atga                                           2964
```

<210> SEQ ID NO 178
<211> LENGTH: 186
<212> TYPE: PRT
<213> ORGANISM: Homo sapiens

<400> SEQUENCE: 178

```
Ser Glu Glu Thr Ile Ser Thr Val Gln Glu Lys Gln Gln Asn Ile Ser
1               5                   10                  15

Pro Leu Val Arg Glu Arg Gly Pro Gln Arg Val Ala Ala His Ile Thr
            20                  25                  30

Gly Thr Arg Gly Arg Ser Asn Thr Leu Ser Ser Pro Asn Ser Lys Asn
```

-continued

```
        35                  40                  45

Glu Lys Ala Leu Gly Arg Lys Ile Asn Ser Trp Glu Ser Ser Arg Ser
    50                  55                  60

Gly His Ser Phe Leu Ser Asn Leu His Leu Arg Asn Gly Glu Leu Val
65                  70                  75                  80

Ile His Glu Lys Gly Phe Tyr Tyr Ile Tyr Ser Gln Thr Tyr Phe Arg
                85                  90                  95

Phe Gln Glu Glu Ile Lys Glu Asn Thr Lys Asn Asp Lys Gln Met Val
            100                 105                 110

Gln Tyr Ile Tyr Lys Tyr Thr Ser Tyr Pro Asp Pro Ile Leu Leu Met
        115                 120                 125

Lys Ser Ala Arg Asn Ser Cys Trp Ser Lys Asp Ala Glu Tyr Gly Leu
    130                 135                 140

Tyr Ser Ile Tyr Gln Gly Gly Ile Phe Glu Leu Lys Glu Asn Asp Arg
145                 150                 155                 160

Ile Phe Val Ser Val Thr Asn Glu His Leu Ile Asp Met Asp His Glu
                165                 170                 175

Ala Ser Phe Phe Gly Ala Phe Leu Val Gly
            180                 185
```